United States Patent [19]
Klar et al.

[11] Patent Number: 5,965,609
[45] Date of Patent: Oct. 12, 1999

[54] BORNEOL ESTERS, PROCESS FOR THEIR PRODUCTION, AND THEIR PHARMACEUTICAL USE

[75] Inventors: Ulrich Klar; Hermann Graf; Günter Neef; Siegfried Blechert, all of Berlin, Germany

[73] Assignee: Schering AG, Berlin, Germany

[21] Appl. No.: 08/930,009

[22] PCT Filed: Mar. 29, 1996

[86] PCT No.: PCT/EP96/01404

§ 371 Date: Mar. 13, 1998

§ 102(e) Date: Mar. 13, 1998

[87] PCT Pub. No.: WO96/32376

PCT Pub. Date: Oct. 17, 1996

[30] Foreign Application Priority Data

Mar. 29, 1995 [DE] Germany .......................... 195 13 040

[51] Int. Cl.$^6$ ..................... A61K 31/335; C07D 303/10
[52] U.S. Cl. ................. 514/475; 514/532; 514/539; 549/510; 549/553; 560/39; 424/450; 424/455
[58] Field of Search .................... 514/475, 532, 514/539; 549/510, 553; 560/39; 424/450, 455

[56] References Cited

U.S. PATENT DOCUMENTS 5,248,796  9/1993  Chen et al. ............................. 549/510
5,792,792  8/1998  Klar et al. .............................. 514/475

*Primary Examiner*—Gary Geist
*Assistant Examiner*—Brian J. Davis
*Attorney, Agent, or Firm*—Millen, White, Zelano & Branigan

[57] ABSTRACT

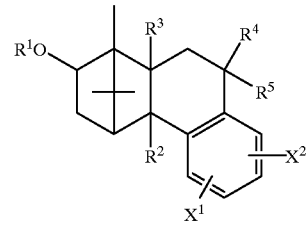

The invention concernes borneol esters of general formula (I), in which $R^1$ means T—C(O)—CH(OR$^6$)—(NR$^{7a}$R$^{7b}$)—R$^8$, C(O)—CH(OR$^{6a}$)—CH[NR$^7$(C(O)—CH(OR$^{6b}$)—CH(NR$^{7a}$R$^{7b}$)—R$^{8a}$)]—R$^{8b}$; R$^{7a}$ R$^{7b}$ are identical or different and means R$^7$; R$^7$ means hydrogen, A, —C(O)R$^{12}$, —C(O)OR$^{12}$, —C(O)SR$^{12}$, —C(O)NHR$^{9d}$, —C(O)NR$^{9d}$R$^{9e}$, —SO$_2$R$^{12}$, C$_1$–C$_{10}$ alkyl; R$^{8a}$, R$^{8b}$ are identical or different and mean R$^8$; R$^8$ means (i), heteroaryl substituted by X$^3$, C$_7$–C$_{16}$ aralkyl, alkyl; A is B—[O—(CH$_2$)$_r$—C(O)]$_{0\ or\ 1}$, farnesyl—P(O)(OR$^{9d}$)—O—(CH$_2$)$_r$—C(O)—; B means protein kinase-inhibitors or farnesyl protein transferase-inhibitors such as for example farnesyl (ii); and T is a bond, Z$^i$ or a group (iii). The borneol esters can influence tubulin polymerisation and tubulin depolymerisation.

17 Claims, No Drawings

BORNEOL ESTERS, PROCESS FOR THEIR PRODUCTION, AND THEIR PHARMACEUTICAL USE

The invention relates to new pharmacologically active compounds, which have the power to influence tubulin polymerization or tubulin depolymerization.

A number of natural mitotic poisons are used an antitumor agents or are undergoing clinical trials. Various classes of these mitotic poisons exist that exert their cytotoxic action either by inhibiting the polymerization of microtubuli in a spindle device (e.g., vinca alkaloids, colchicine) or accomplish this by GTP-independent increase of the polymerization of the tubulin and prevention of the depolymerization of microtubuli (e.g., taxol, taxotere). Owing to previously little-understood physicochemical properties and the characteristics of neoplastic cells, mitotic poisons have a certain selectivity for tumor cells, but there is also significant cytotoxicity with regard to nontransformed cells.

Up until now, vinca alkaloids have had great importance in the combined chemotherapy of myeloid tumors. Taxanes have very recently opened up important applications that were not accessible by previously available cytostatic agents, e.g., ovarian cancers, malignant melanomas. The side effects of taxanes are comparable to those of other cytostatic agents, however (e.g., loss of hair, sensory neuropathy). Multi-drug-resistant tumor cells, which overexpress the P-glycoprotein, are resistant to taxanes. The limited availability of the natural substance taxol also inhibits broader clinical trials.

Natural substances and synthetic pharmaceutical agents that have a spectrum of action unlike that of the previous mitotic poisons were therefore tested. An in vitro experimental arrangement makes it possible to search for substances that do not influence the GTP-dependent polymerization of tubulin, but prevent the depolymerization of the microtubuli formed. Substances with such a profile of action should influence the versatile functions of microtubuli in extranuclear cell compartments less strongly than the dynamic of the spindle device during mitosis (metaphase/anaphase). Logically, such compounds should have fewer side effects in vivo than taxanes or vinca alkaloids.

Tubulin is an essential component of the mitotic spindle. It is used, i.a., to preserve the cell shape, to transport organelles inside the cell, and to influence cell mobility.

Up until now, taxanes have represented the only known structural class that is able to accelerate the polymerization of tubulin (mainly in the G2 phase), as well as to stabilize the microtubuli polymers formed. This mechanism is clearly distinguishable from those that have other structural classes which also influence the phase-specific cell division. Thus, for example, substances from the group of vinca alkaloids (e.g., vincristines and vinblastines) but also colchicine inhibit the polymerization of the tubulin dimers in the M phase.

It has now been found that compounds of formula I that are comparatively simple to produce are able to inhibit the depolymerization of microtubuli with out increasing the formation of microtubuli in a GTP-independent manner. Moreover, compounds with a completely new profile of action that are able to accelerate the depolymerization of microtubuli were identified. On the basis of these properties, the compounds of formula I represent valuable pharmaceutical agents that are basically able to supplement or replace taxanes, which are difficult to synthesize and which are still not available in sufficient quantities, such as, e.g., taxol and Taxotere®, in the treatment of malignant tumors (EP-A 253739).

The new borneol derivatives are characterized by general formula I

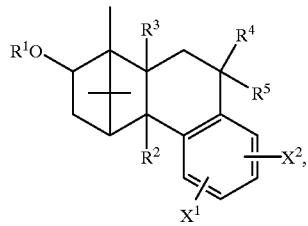

in which $R^1$ means $C(O)-CH(OR^6)-CH(NR^{7a}R^{7b})-R^8$, $C(O)-CH(OR^{6a})-CH[NH(C(O)-CH(OR^{6b})-CH(NR^{7a}R^{7b})-R^{8a})]-R^{8b}$, $R^2$ means hydrogen, $-OH$, $C_1-C_{10}$ alkyl, $C_1-C_{10}$ alkoxy, $-OC(O)R^{9a}$, $-OSO_2R^{9a}$, $NHR^{9a}$, $NR^{9a}R^{9b}$, $R^3$ means hydrogen, $-OH$, $C_1-C_{10}$ alkoxy, $-OC(O)R^{9b}$, $-OSO_2R^{9b}$, or $R^2$, $R^3$ together means oxygen atom, $R^4$ means hydrogen, $C_1-C_{10}$ alkyl, $-(CH_2)_n-OR^{11a}$, $R^5$ means hydrogen, $C_1-C_{10}$ alkyl, $-(CH_2)_p-OR^{11b}$, or $R^4$, $R^5$ together means an oxygen atom, a $=CHR^{10}$ group, $R^{6a}$, $R^{6b}$ are the same or different and mean $R^6$, $R^4$, $R^5$ together mean an oxygen atom, a $=CHR^{10}$ group, a $-CH_2-CH_2$ group, a $CH_2-O$ group, $R^{6a}$, $R^{6b}$ are the same or different and mean $R^6$, $R^6$ means hydrogen, $C_1-C_{10}$ alkyl, aryl, $C_1-C_{20}$ acyl, $C_7-C_{20}$ aralkyl, $-SO_2R^{9c}$, $R^{15}$, $R^{7a}$, $R^{7b}$ are the same or different and mean $R^7$, $R^7$ means hydrogen, A, $-C(O)R^{12}$, $-C(O)OR^{12}$, $-C(O)SR^{12}$, $-C(O)NHR^{9d}$, $-C(O)NR^{9d}R^{9e}$, $-SO_2R^{12}$, $C_1-C_{10}$ alkyl, $R^{8a}$, $R^{8b}$ are the same or different and means $R^8$, $R^8$ means

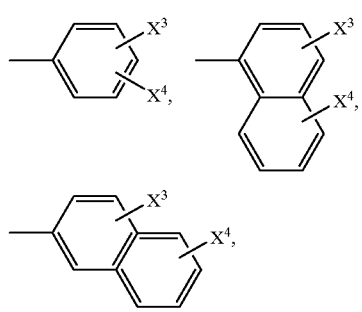

heteroaryl substituted by $X^3$, $C_7-C_{16}$ aralkyl, $C_1-C_{10}$ alkyl, $R^{9a-g}$, $R^{12}$ are the same or different and mean $C_1-C_{20}$ alkyl, $C_4-C_8$ cycloalkyl, aryl, $C_7-C_{20}$ aralkyl, $R^{10}$ means hydrogen, $C_1-C_{10}$ alkyl, $-(CH_2)_s-OR^{13}$, $R^{11a,b}$, $R^{13}$ are the same or different and mean hydrogen, $C_1-C_{10}$ alkyl, aryl, $C_1-C_{20}$ acyl, $C_7-C_{20}$ aralkyl, $-SO_2R^{9c}$, $R^{14a,b}$ are the same or different and mean hydrogen, A, $C_1-C_{10}$ alkyl, aryl, $C_7-C_{16}$ aralkyl, $R^{15}$ means $(Y^i_1-Y^i_2-Y^i_3-\ldots-Y^i_r)-H$, A means $B-[O-(CH_2)_t-C(O)_0 \text{ or } _{1}-$, farnesyl$-P(O)(OR^{9d})-O-(CH_2)_t-C(O)-$, B means inhibitors of protein kinases or inhibitors of farnesyl protein transferase, such as, e.g., farnesyl, T means a bond, $Z^i$ or a group

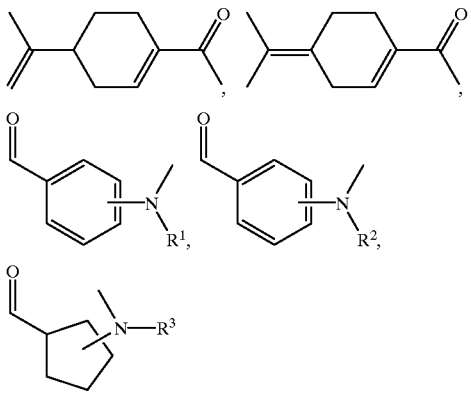

$X^1 \ldots X^4$ are the same or different and mean X, whereby $X^3$ and $X^4$ in the case of $R^8$ and $R^{8b}$ cannot be used at the same time, however, in the meaning of hydrogen, X can be hydrogen, halogen, $-NO_2$, $-N_3$, $-CN$, $-NR^{14a}R^{14b}$, $-NHSO_2R^{9g}$, $C_1$-$C_{10}$ alkyl, $C_1$-$C_{20}$ acyl, $C_1$-$C_{20}$ acyloxy, $OR^6$, $-OP(O)R^{9g}(OR^{12})-CO_2R^{14}$, $-O-A$, $Y^i_{1 \ldots r}$ are the same or different and mean $-[C(O)-W^i-NH]-=Z^i$, whereby $Z^i$ as $HO-Z^i-H$ represents an α-, β- or γ-amino acid "i" that is linked on its terminal end, n means 0 to 8 p means 1 to 8 r means 1 to 5 s means 1 to 8 t means 1 to 6, and free hydroxyl groups in $R^1$, $R^2$, $R^3$, $R^4$, $R^5$, $R^{10}$, Z and X can be further modified functionally by etherification or esterification and free amino groups in $R^1$, $R^{15}$ or X or free acid groups in X can be converted into their salts with physiologically compatible acids or bases, as well as their α-, β- or γ-cyclodextrin clathrates, as well as the compounds of general formula I that are encapsulated with liposomes.

The invention relates to the diastereomers and/or enantiomers of these borneol derivatives and also their mixtures.

As alkyl groups $R^2$, $R^4$, $R^5$, $R^6$, $R^7$, $R^8$, $R^9$, $R^{10}$, $R^{11}$, $R^{12}$, $R^{13}$, $R^{14}$ and X, straight-chain or branched-chain alkyl groups with 1–20 carbon atoms can be considered, such as, for example, methyl, ethyl, propyl, isopropyl, butyl, isobutyl, tert-butyl, pentyl, isopentyl, neopentyl, heptyl, hexyl, decyl.

Alkyl groups $R^2$, $R^4$, $R^5$, $R^6$, $R^7$, $R^8$, $R^9$, $R^{10}$, $R^{11}$, $R^{12}$, $R^{13}$, $R^{14}$ and X can be substituted by 1–3 halogen atoms, hydroxy groups, $C_1$-$C_4$ alkoxy groups, $C_6$-$C_{12}$ aryl groups, which can be substituted by 1–3 halogen atoms, di-($C_1$-$C_4$)-alkylamines and tri-($C_1$-$C_4$) alkylammonium.

As cycloalkyl groups $R^9$, $R^{12}$, substituted and unsubstituted radicals with 4 to 8 carbon atoms are suitable.

As aryl radicals $R^6$, $R^9$, $R^{11}$, $R^{12}$, $R^{13}$ and $R^{14}$, substituted and unsubstituted carbocyclic or heterocyclic ($R^8$) radicals, such as, e.g., phenyl, naphthyl, furyl, thienyl, pyridyl, pyrazolyl, pyrimidinyl, oxazolyl, pyridazinyl, pyrazinyl, quinolyl, which can be substituted several times by the groups that are defined in X, are suitable.

The alkoxy, acyl and acyloxy groups that are contained in $R^2$, $R^3$, $R^6$, $R^{11}$, $R^{13}$ and X of general formula I are to contain 1 to 20 carbon atoms in each case, whereby methoxy, ethoxy, propoxy, isopropoxy, t-butyloxy, formyl, acetyl, propionyl and isopropionyl groups are preferred.

The aralkyl groups $R^6$, $R^8$, $R^9$, $R^{12}$, $R^{13}$ and $R^{14}$ can contain up to 14 C atoms, preferably 6 to 10 C atoms, in the ring and 1 to 6 atoms, preferably 1 to 4 atoms, in the alkyl chain. Preferred aralkyl radicals are, e.g., benzyl, phenylethyl, naphthylmethyl or naphthylethyl. The rings can be substituted several times by the groups that are defined in X.

The amino acid $HO-Z-H$ can represent a natural or unnatural α, β or γ-amino acid that is modified, i.e., relative to its configuration or substitution. Preferred are, e.g., glycine, alanine, valine, leucine, isoleucine, and proline.

Free amino groups in $R^1$, $R^{15}$, X or $HO-Z-H$ can be modified functionally by alkylation and/or acylation or equipped with the protective groups that are familiar to one skilled in the art, such as, e.g., tert-butyloxycarbonyl, benzyloxycaronyl, allyloxycarbonyl, 9-fluorenylmethoxycarbonyl.

Tertiary amino groups in $R^1$, $R^2$, $R^{15}$ and X can be modified functionally, for example, by oxidation to the corresponding N-oxides, by salt formation with alkyl halides or with physiologically compatible acids.

Free hydroxyl groups $R^1$, $R^2$, $R^3$, $R^4$, $R^5$, $R^{10}$, Z and X can be modified functionally, for example, by etherification or esterification. In addition to free hydroxyl groups $-OH$, those derivatives are preferred that are able to improve the water-solubility of the compounds. For example, there can be mentioned here the esterification with amino acids and their derivatives, pyridinium slats with physiologically compatible acids, such as, e.g.,

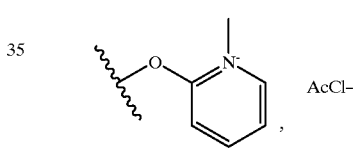

phosphates or their salts with physiologically compatible bases and their esters such as, e.g., $-O-P(O)$ $(OH)_2$, $-O-P(O)$ $(OR^{9f})_2$, $-O-P(O)$ $(OR^{9f})$ $(OH)$, sulfate or their salts with physiologically compatible bases and their esters, such as e.g., $-O-SO_3H$, $-O-SO_3R^{9f}$, esters and ethers with water-soluble polymers, such as, e.g., polyethyleneglycol (PEG), which are linked via suitable groups with the free hydroxyl groups, such as, e.g., $-O-C(O)-CH_2-O-PEG$, $-O-C(O)-CH_2-CH_2-C(O)-NH-PEG$, $-O-C(O)-CH_2-NH-C(O)-O-PEG$.

Also preferred are ethers, esters and amides with compounds that in turn are able to exert tumor-inhibiting action. Radicals $R^7$ and $R^{14}$ represent the preferred linkage position of such compounds. For example, compounds which inhibit the intracellular isoprenylation of proteins, such as., e.g., perillic acid dihydroperillic acid, farnesyl, etc., can be mentioned.

As ether and acyl radicals, the radicals that are known to one skilled in the art are suitable. Preferred are easily cleavable ether radicals, such as, for example, the tetrahydropyranyl, tetrahydrofuranyl, tert-butyldimethylsilyl, tert-butyldimethylsilyl, tribenzylsilyl radical. As acyl radicals, e.g., acetyl, propionyl, butyryl, benzoyl and alkanoyl that is substituted by, e.g., amino and/or hydroxy groups are suitable.

Halogen in the definitions of X means fluorine, chlorine, bromine and iodine.

For salt formation with the free acids of bases, inorganic and organic bases or acids are suitable, as they are known to one skilled in the art for the formation of physiologically compatible salts. For example, there can be mentioned: alkali hydroxides, such as sodium or potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, or acetic acid, citric acid, tartaric acid, hydrochloric acid, etc.

The invention also relates to a process for the production of borneol derivatives of formula I, which is characterized in that an alcohol of general formula II

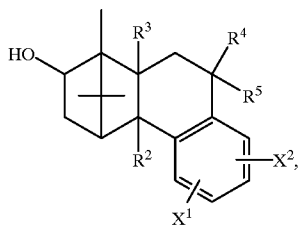

II in which $R^2$, $R^3$, $R^4$, $R^5$, $X^1$ and $X^2$ have the above-mentioned meanings and hydroxyl groups that are contained in $R^2$, $R^3$, $R^4$, $R^5$, $X^1$ or $X^2$ are optionally protected, is reacted with a compound of general formula IIIa, IIIb or IIIc,

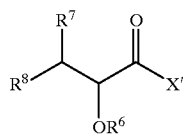

IIIa

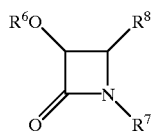

IIIb

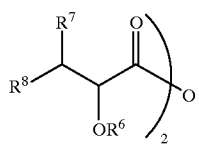

IIIc in which $R^6$, $R^7$ and $R^8$ in each case have the above-mentioned meanings and X' can be hydroxyl, $OR^9$, halogen and $NR^{14a}R^{14b}$, to compounds of general formula I, in which free hydroxyl groups can be further modified functionally by etherification or esterification.

The conversion of compounds of formula II into a compound of formula I can be carried out in various sequences;
1) Esterification of the alcohol function ($R^1$=hydrogen) →modification of $R^4$ and/or $R^5$→optionally epoxide opening, if $R^2$ and $R^3$ together represent an oxygen atom, optionally with subsequent modification of $R^2$ and $R^3$.
2) Esterification of alcohol function ($R^1$=hydrogen) →optionally epoxide opening, if $R^2$ and $R^3$ together represent an oxygen atom, optionally with subsequent modification of $R^2$, $R^3$, $R^4$ and/or $R^5$.
3) Protection of alcohol function ($R^1$=hydrogen) →optionally epoxide opening, if $R^2$ and $R^3$ together represent an oxygen atom, optionally with subsequent modification of $R^2$ and $R^3$→modification of $R^4$ and/or $R^5$→release and subsequent esterification of alcohol function ($R^1$=hydrogen).
4) Protection of alcohol function ($R^1$=hydrogen) →modification of $R^4$ and/or $R^5$→release and subsequent esterification of the alcohol function ($R^1$=hydrogen)→optionally epoxide opening, if $R^2$ and $R^3$ together represent an oxygen atom, optionally with subsequent modification of $R^2$ and $R^3$.

For esterification of the alcohol function ($R^1$=hydrogen), 1,4-diazabicyclo[2.2.2]octane (DABCO) is deprotonated with a base, such as, e.g., metal hydrides (e.g., sodium hydride), alkali alcoholates (e.g., sodium methanolate, potassium-tert-butanolate), alkali hexamethyl disilazane (e.g., sodium hexamethyl disilazane), 1,5-diazabicyclo [4.3.0]non-5-ene (DBN), 1,8-diazabicyclo[5.4.0]undec-7-ene (DBU), triethylamine, 4-(dimethylamino)pyridine (DMAP), and reacted with carboxylic acid derivatives of general formula III in an inert solvent such as, e.g., dichloromethane, diethyl ether, tetrahydrofuran at −70° C. to +50° C. Preferred is the reaction with sodium hexamethyl disilazane as a base, a cyclic acid amide as a carboxylic acid derivative, tetrahydrofuran as a solvent at temperatures of −40° C. to +25° C.

If $R^4$ and $R^5$ together represent a $=CHR^{10}$ group, the functionalization of the olefinic double bond can be carried out according to the methods that are known to one skilled in the art. For example, hydrogen can be stored by e.g., catalyzed hydrogenation; hydroxyl groups can be introduced by water addition (hydroboration, oxymercurization) or by 1,2-bis-hydroxylation with, e.g., osmium tetroxide or potassium permanganate. The introduction of a carbonyl group ($R^4$, $R^5$ together represent an oxygen atom) is possible after cleavage of the double bond, e.g., by ozonolysis or by oxidative cleavage of a 1,2-diol. A carbonyl group that is produced in such a way can be used, for example, reduced, alkylated or as a carbonyl component in a Wittig reaction in building modified $=CHR^{10}$ groups.

If $R^2$ and $R^3$ together represent an oxygen atom, the epoxide can be reacted by nucleophiles, such as, for example, water, carboxylic acid derivatives (carboxylic acids, carboxylic acid halides, carboxylic anhydrides), sulfonic acid derivatives (sulfonic acids, sulfonic acid halides, sulfonic anhydrides), amines, in the presence of mineral or organic acids, such as, for example, hydrochloric acid, para-toluenesulfonic acid or Lewis acids, such as, for example, boron trifluoride etherate, titanium tetraisopropoxide, cerium ammonium nitrate either in inert solvents or as solvents that act as nucleophiles at −70° C. up to +50° C.

Free hydroxyl groups in I can be further modified functionally according to the methods that are known to one skilled in the art, for example by etherification or esterification. For example, free hydroxyl groups in pyridinium salts can be converted with physiologically compatible acids into phosphates or their salts with physiologically compatible bases or into their esters, into sulfates or their salts with physiologically compatible bases or into their esters or into esters and ethers with water-soluble polymers. Ethers and esters of compounds that in turn are able to exert tumor-inhibiting action can also be produced.

Biological Effects and Applications of New Borneol Derivatives

The new compounds of formula I are valuable pharmaceutical agents. They interact with tubulin by stabilizing the microtubuli formed and are thus able to influence cell division in a phase-specific manner. This relates mainly to quick-growing, neoplastic cells, whose growth is largely unaffected by intercellular regulating mechanisms. Active ingredients of this type are mainly suitable for treating diseases in which the influence of cell division can be therapeutically indicated.

By way of example, there can be mentioned here the treatment of malignant tumors, malaria, treatment of diseases that are caused by gram-negative bacteria, as well as the treatment of diseases of the central and peripheral nervous system, which are based on excitotoxic symptoms, such as, e.g., the treatment of acute neurodegenerative phenomena, as they develop, for example, by stroke or traumatic brain injuries, the treatment of chronic neurodegenerative symptoms including Alzheimer's disease as well as the treatment of amyotropic lateral schlerosis.

As applications for malignant tumors, for example, the treatment of ovarian, stomach, colon, adeno-, breast, lung, head and neck carcinomas, malignant melanoma, acute lymphocytic and myelocytic leukemia can be mentioned.

The compounds according to the invention can be used generally by themselves or to achieve additive or synergistic actions in combination with other principles and classes of substances that can be used in the respective therapy fields.

In the example of tumor therapy, there can be mentioned the combination with

Platinum complexes such as, e.g., cis-platinum, carboplatinum, intercalating substances, e.g., from the class of anthracyclins, such as, e.g., doxorubicin or from the class of anthrapyrazoles, such as, e.g., CI-941, substances that interact with tubulin, e.g., from the class of vinca alkaloids, such as, e.g., vincristine, vinblastine or from the class of taxanes, such as, e.g., taxol, taxotere or from the class of macrolides, such as, e.g., rhizoxin or other compounds, such as, e.g., colchicine, combretastatin A-4, DNA topoisomerase inhibitors, such as, e.g., camptothecin, etoposide, topotecan, teniposide, folate- or pyrimidine-antimetabolites, such as, e.g., lometrexol, gemcitubin, compounds that alkylate DNA, such as, e.g., adozelesin, dystamycin A, inhibitors of growth factors (e.g., of PDGF, EGF, TGFβ, EGF), such as, e.g., somatostatin, suramin, bombesin antagonists, inhibitors of protein tyrosine kinase or protein kinases A or C, such as e.g., erbstatin, genisteine, staurosporine, ilmodosine, 8-Cl-cAMP, antihormones form the class of antigestagens, such as, e.g., mifepristone, onapristone, or from the class of antiestrogens, such as, e.g., tamoxifen, or from the class of antiandrogens, such as, e.g., cyproterone acetate, compounds that inhibit metastases, e.g., from the class of eicosanoids, such as, e.g., $PGI_2$, $PGE_1$, 6-oxo-$PGE_1$ as well as their more stable derivatives (e.g., iloprost, cicaprost, beraprost), inhibitors of the transmembrane $Ca^{2+}$ influx, such as, e.g., verapamil, galopamil, flunarizine, diltiazem, nifedipine, nimodipine, neuroleptic agents, such as, e.g., chlorpromazine, trifluoperazine, thioridazine, perphenazine, local anesthetics, such as, e.g., carbanilat-Ca7, cinchocaine, carbanilat-Ca3, articaine, carbanilat, lidocaine, substances that inhibit angiogenesis, such as, e.g., anti-VEGF-antibodies, endostatin B, interferon α, AGM 1470, inhibitors of cell proliferation in psoriasis, Kaposi's sarcoma, neuroblastoma.

The invention also relates to pharmaceutical agents that are based on pharmaceutically compatible compounds, i.e., compounds of general formula I that are not toxic in the doses used, optionally together with the adjuvants and vehicles that are commonly used.

The compounds according to the invention can be worked into pharmaceutical preparations for enteral, percutaneous, parenteral or local administration according to methods of galenicals that are known in the art. They can be administered in the form of tablets, coated tablets, gel capsules, granulates, suppositories, implants, injectable sterile aqueous or oily solutions, suspensions or emulsions, ointments, creams and gels.

In this case, the active ingredient or ingredients can be mixed with the adjuvants that are commonly used in galenicals, such as, e.g., gum arabic, talc, starch, mannitol, methyl cellulose, lactose, surfactants such as Tween or Myrj, magnesium stearate, aqueous or non-aqueous vehicles, paraffin derivatives, wetting agents, dispersing agents, emulsifiers, preservatives and flavoring substances for taste correction (e.g., ethereal oils).

The invention thus also relates to pharmaceutical compositions, which as active ingredient contain at least one compound according to the invention. A dosage unit contains about 0.1–100 mg of active ingredient(s). In humans, the dosage of the compounds according to the invention is approximately 0.1–1000 mg per day.

The embodiments below are used to explain the process according to the invention in more detail.

EXAMPLE 1

[1R-[1α,2β(2R*,3S*), 4α,4aβ,10aβ]]-3-(Ethoxycarbonyl)amino-2-hydroxy-3-(4-methoxyphenyl)-propanoic acid-9-methylene-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,10aβ]]-3-(ethoxycarbonyl)amino-2-hydroxy-3-(4-methoxyphenyl)-propanoic acid-9-methylene-1,2,3,4,4a,9,10,10a-octahydro-1,12,12-trimethyl-4a,10a-epoxy-1,4-methanophenanthren-2-ylester (B)

18 mg (26 μmol) of the compounds that are presented according to Example 1a is dissolved under an atmosphere of dry argon in 0.3 ml of anhydrous tetrahydrofuran, mixed with 39 μl of a 1.1 M solution of tetrabutylammonium fluoride in tetrahydrofuran and stirred for 0.5 hour at 23° C. It is concentrated by evaporation, and the residue is purified by chromatography on an analytical thin-layer plate. A mixture of n-hexane and ethyl acetate is used as a mobile solvent; a mixture of diethyl ether in 2-propanol is used as an eluant. 3 mg (5.5 μmol, 21%) of title compound A as well as 4 mg (7.3 μmol, 28%) of title compound B are isolated, in each case as a colorless oil.

$^1$H-NMR (CDCl$_3$) of A: δ=0.87 (3H), 0.93 (3H), 1.09 (3H), 1.23 (3H), 1.76 (1H), 2.31 (1H), 2.71 (1H), 2.79 (1H), 3.10 (1H), 3.14 (1H), 3.76 (3H), 4.12 (2H), 4.51 (1H), 4.93 (1H), 5.05 (1H), 5.20 (1H), 5.52 (1H), 6.33 (1H), 6.81 (2H), 7.28–7.43 (4H), 7.51 (1H), 7.56 (1H) ppm.

$^1$H-NMR (CDCl$_3$) of B: δ=0.85 (3H), 0.95 (3H), 1.08 (3H), 1.21 (3H), 1.82 (1H), 2.39 (1H), 2.70 (1H), 2.72 (1H), 3.17 (1H), 3.20 (1H), 3.80 (3H), 4.10 (2H), 4.54 (1H), 5.03 (1H), 5.10 (1H), 5.26 (1H), 5.50 (1H), 5.65 (1H), 6.88 (2H), 7.22–7.39 (4H), 7.45 (1H), 7.51 (1H) ppm.

EXAMPLE 1a

[1R-[1α,2β(2R*,3S*),4α,4aβ,10aβ]]-3-(Ethoxycarbonyl) amino-2-(triisopropylsilyloxy)-3-(4-methoxyphenyl)-propanoic acid-9-methylene-1,2,3,4,4a,10,10a-octahydro-1, 12,12-trimethyl-4a,10a-epoxy-1,4-methanophenanthren-2-ylester and [1S-[1α,2β(2R*,3S*),4α,4aβ,10aβ]]-3-(ethoxycarbonyl)amino-2-(triisopropylsilyloxy)-3-(4-methoxyphenyl)-propanoic acid-9-methylene-1,2,3,4,4a,9, 10,10a-octahydro-1,12,12-trimethyl-4a,10a, epoxy-1,4-methanophenanthren-2-ylester 30 mg (106 μmol) of an approximately 6:4 mixture of [1R-(1α,2β4α,4aβ,10aβ)]-9-methylene-1,2,3,4,4a,9,10, 10a-octahydro-1,12,12-trimethyl-4a,10a-epoxy-1,4-methanophenanthren-2-ol and [1S-1α,2β,4α,4aβ,10aβ)]-9-methylene-1,2,3,4,4a,9,10,10a-octahydro-1,12,12-trimethyl-4a,10a-epoxy-1,4-methanophenanthren-2-ol, which has been produces analogously to the process that is described in J. Am. Chem. Soc. 1992, on page 5879 ff, as well as 70 mg of (3R,4S)-1-(ethoxycarboxyl)-3-triisopropylsilyloxy-4-(4-methoxyphenyl)-2-azetidinone, which has been produced analogously to the process that is described in Tetrahedron 1992 on page 6985 ff, are dissolved under an atmosphere of dry argon in 1.1 ml of anhydrous tetrahydrofuran, mixed at 0° C. with 0.14 ml of a 1 M solution of sodium hexamethyl disilazane in tetrahydrofuran, allowed to heat to 23° C. and stirred for 2 more hours. It is poured into saturated ammonium chloride solution, extracted several times with ethyl acetate, the combined organic extracts are washed with water and saturated sodium chloride solution and dried on sodium sulfate. The residue that is obtained after filtration and removal of solvent is separated by chromatography on an analytical thin-layer plate. A mixture of n-hexane and ethyl acetate is used as a mobile solvent; a mixture of diethyl ether in 2-propanol is used as an eluant. 25 mg (36 μmol, 34%) of the title compounds, which are further reacted without separation, is isolated as a colorless oil.

EXAMPLE 2

[1R-[1α,2β(2R*,3S*),4α,4aβ,10aβ]]-3-(Ethoxycarbonyl) amino-2-hydroxy-3-(4-fluorophenyl)-propanoic acid-9-methylene-1,2,3,4,4a,9,10,10a-octahydro-1,12,12,-trimethyl-4a,10a-epoxy-1,4-methanophenanthren-2-ylester (A) and [1S-[1α,2β(2R*,3S*),4α,4aβ,10aβ]]-3-(ethoxycarbonyl)amino-2-hydroxy-3-(4-fluorophenyl)-propanoic acid-9-methylene-1,2,3,4,4a,9,10,10a-octahydro-1,12,12-trimethyl-4a,10a-epoxy-1,4-methanophenanthren-2-ylester (B)

10 mg (14 μmol) of the compounds that are presented according to Example 2a is reacted analogously to Example 1. After working-up and purification, 2.4 mg (4.5 μmol, 32%) of title compound A as well as 2.2 mg (4.1 μmol, 29%) of title compound B are isolated, in each case as a colorless oil.

$^1$H-NMR (CDCl$_3$) of A: δ=0.86 (3H), 0.93 (3H), 1.08 (3H), 1.21 (3H), 1.69 (1H), 2.31 (1H), 2.72 (1H), 2.79 (1H), 3.11 (1H), 3.16 (1H), 4.10 (2H), 4.51 (1H), 4.92 (1H), 5.06 (1H), 5.24 (1H), 5.53 (1H), 6.39 (1H), 6.97 (2H), 7.32 (2H), 7.40–7.60 (4H) ppm.

$^1$H-NMR (CDCl$_3$) of B: δ=0.85 (3H), 0.97 (3H), 1.07 (3H), 1.22 (1H), 1.81 (1H), 2.38 (1H), 2.70 (1H), 2.27 (1H), 3.17 (1H), 3.22 (1H), 4.10 (2H), 4.53 (1H), 5.04 (1H), 5.09 (1H), 5.28 (1H), 5.49 (1H), 5.68 (1H), 7.03 (2H), 7.23–7.43 (4H), 7.45 (1H), 7.51 (1H) ppm.

EXAMPLE 2a

[1R-[1α,2β(2R*,3S*),4α,4aβ,10aβ]]-3-(Ethoxycarbonyl) amino-2-(triisopropylsilyloxy)3-(4-fluorophenyl)-propanoic acid-9-methylene-1,2,3,4,4a,9,10,10a-octahydro-1,12,12-trimethyl-4a,10a-epoxy-1,4-methanophenanthren-2-ylester and [1S-[1α,2β(2R*,3S*),4α,4β,10aβ]]-3-(ethoxycarbonyl) amino-2-(triisopropylsilyloxy)-3-(4-fluorophenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 20 mg (70 μmol) of an approximately 7:3 mixture of [1R-(1α,2β,4α,4aβ,10aβ)]-9-methylene-1,2,3,4,4a,9,10,10a-octahydro-1,12,12-trimethyl-4a-10a-epoxy-1,4-methanophenanthren-2-ol and [1S-(α,2β,4α,10aβ)]-9-methylene-1,2,3,4,4a,10,10a-octahydro-1,12,12-trimethyl-4a,10a-epoxy-1,4-methanophenanthren-2-ol are reacted using (3R,4S)-1-(ethoxycarbonyl)-3-triisopropylsilyloxy-4-(4-fluorophenyl)-2-azetidinone, which has been produced analogously to the process that is described in Tetrahedron 1992 on page 6985 ff. After working-up and purification, 31 mg (45 μmol, 64%) of the title compounds is isolated as a colorless oil.

EXAMPLE 3

[1R-[1α,2β(2R*,3S*),4α,4aβ,10aβ]]-3-(Ethoxycarbonyl) amino-2-hydroxy-3-(4-hydroxyphenyl)-propanoic acid-9-methylene-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,10aβ]]-3-(ethoxycarbonyl)amino-2-hydroxy-3-(4-hydroxyphenyl)-propanoic acid-9-methylene-1,2,3,4,4a,9,10,10a-octahydro-1,12,12-trimethyl-4a,10a-epoxy-1,4-methanophenanthren-2-ylester (B)

16 mg (20 μmol) of the compounds that are presented according to Example 3a is reacted analogously to Example 1. After working-up and purification, 2.6 mg (4.9 μmol, 24%) of title compound A as well as 2.9 mg (5.4 μmol, 27%) of title compound B are isolated, in each case as a colorless oil.

$^1$H-NMR (CDCl$_3$) of A: δ=0.85 (3H), 0.93 (3H), 1.07 (3H), 1.21 (3H), 1.73 (1H), 2.30 (1H), 2.71 (1H), 2.78 (1H), 3.13 (2H), 4.10 (2H), 4.49 (1H), 4.92 (1H), 5.04 (1H), 5.18 (1H), 5.52 (1H), 6.33 (1H), 6.69 (2H), 8.22–7.39 (4H), 7.50 (1H), 7.55 (1H) ppm.

$^1$H-NMR (CDCl$_3$) of B: δ=0.84 (3H), 0.95 (3H), 1.07 (3H), 1.22 (3H), 1.81 (1H), 2.38 (1H), 2.70 (1H), 2.72 (1H), 3.18 (1H), 3.21 (1H), 4.09 (2H), 4.51 (1H), 5.03 (1H), 5.10 (1H), 5.22 (1H), 5.40 (1H), 5.50 (1H), 5.67 (1H), 6.72 (2H), 7.16–7.33 (4H), 7.46 (1H), 7.52 (1H) ppm.

EXAMPLE 3a

[1R-1α,2β(2R*,3S*),4α,4aβ,10aβ]]-3-(Ethoxycarbonyl) amino-2-(triisopropylsilyloxy)-3-(4-hydroxyphenyl)-propanoic acid-9-methylene-1,2,3,4,4a,9,10,10a-octahydro-1,12,12-trimethyl-4a,10a-epoxy-1,4-methanophenanthren-2-ylester and [1S-[1α,2β(2R*,3S*),4α,4aβ,10aβ]]-3-(ethoxycarbonyl)amino-2-(triisopropylsilyloxy)-3-(4-hydroxyphenyl)-propanoic acid-9-methylene-1,2,3,4,4a,9, 10,10a-octahydro-1,12,12-trimethyl-4a,10a-epoxy-1,4-methanophenanthren-2-ylester By analogy with Example 1a, 121 mg (428 μmol) of an approximately 7:3 mixture of [1R-(1α,2β,4α4aβ,10aβ)]-9-methylene-1,2,3,4,4a,9,10,10a-octahydro-1,12,12-trimethyl-4a,10a-epoxy-1,4-methanophenanthren-2-ol and [1S-(1α,2β,4α,4aβ,10aβ)]-9-methylene-1,2,3,4,4a,9,10, 10a-octahydro-1,12,12-trimethyl-4a,10a-epoxy-1,4-methanophenanthren-2-ol are reacted using (3R,4S)-1-(ethoxycarbonyl-3-triisopropylsilyloxy-4-[4-(tert-butyldimethylsilyloxy)phenyl]-2-azetidinone, which has been produced analogously to the process that is described in Tetrahedron 1992 on page 6985 ff. After working-up and purification, 180 mg (224 μmol, 52%) of the title compounds is isolated as a colorless oil.

EXAMPLE 4
[1R-[1α,2B(2R*,3S*),4α,4aβ,10aβ]]-3-(Ethoxycarbonyl) amino-2-hydroxy-3-(3-methylphenyl)-propanoic acid-9-methylene-1,2,3,4,4a,9,10,10a-octahydro-1,12,12-trimethyl-4a,10a-epoxy-1,4-methanophenanthren-2-ylester 14 mg (20 μmol) of the compound that is presented according to Example 4a is reacted analogously to Example 1. After working-up and purification, 7 mg (13 μmol, 66%) of the title compound is isolated as a colorless oil.

$^1$H-NMR (CDCl$_3$): δ=0.86 (3H), 0.93 (3H), 1.08 (3H), 1.23 (3H), 1.78 (1H), 2.27 (3H), 2.32 (1H), 2.72 (1H), 2.79 (1H), 3.08 (1H), 3.14 (1H), 4.11 (2H), 4.52 (1H), 4.93 (1H), 5.06 (1H), 5.21 (1H), 5.53 (1H), 6.36 (1H), 7.04 (1H), 7.16 (1H), 7.21–7.36 (4H), 7.49 (1H), 7.55 (1H) ppm.

EXAMPLE 4a
[1R-[1α,2B(2R*,3S*),4α,4aβ,10aβ]]-3-(Ethoxycarbonyl) amino-2-(triisopropylsilyloxy)-3-(3-methylphenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 30 mg (106 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(3-methylphenyl)-2-azetidinone, which has been produced analogously to the process that is described in Tetrahedron 1992 on page 6985 ff. After working-up and purification, 17 mg (25 μmol, 23%) of the title compound is isolated as a colorless oil.

$^1$H-NMR (CDCl$_3$): δ=0.82 (3H), 0.91 (3H), 0.86–1.19 (24H), 1.23 (3H), 1.60 (1H), 2.23 (1H), 2.27 (3H), 2.64 (1H), 2.74 (1H), 3.10 (1H), 4.11 (2H), 4.63 (1H), 4.89 (1H), 5.03 (1H), 5.20 (1H), 5.51 (1H), 6.35 (1H), 7.01 (1H), 7.13 (1H), 7.19–7.35 (4H), 7.5 (1H), 7.53 (1H) ppm.

EXAMPLE 5
[1R-[1α,2B(2R*,3S*),4α,4aβ,10aβ]]-3-(Ethoxycarbonyl) amino-2-hydroxy-3-(2-naphthyl)-propanoic acid-9-methylene-1,2,3,4,4a,9,10,10a-octahydro-1,12,12-trimethyl-4a,10a-epoxy-1,4-methanophenanthren-2-ylester Analogously to Example 1, 8 mg (11 μmol) of the compound that is presented according to Example 5 a is reacted. After working-up and purification, 3 mg (5.3 μmol, 48%) of the title compound is isolated as a colorless oil.

$^1$H-NMR (CDCl$_3$): δ=0.86 (3H), 1.07 (3H), 1.23 (3H), 1.74 (1H), 2.23 (1H), 2.71 (1H), 2.80 (1H), 3.31 (1H), 3.18 (1H), 4.12 (2H), 4.61 (1H), 4.91 (1H), 5.07 (1H), 5.43 (1H), 5.56 (1H), 6.53 (1H), 7.34 (2H), 7.42 (2H), 7.50–7.65 (3H), 7.65–7.87 (3H), 7.97 (1H) ppm.

EXAMPLE 5a
[1R-[1α,2B(2R*,3S*),4α,4aβ,10aβ]]-3-(Ethoxycarbonyl) amino-2-(triisopropylsilyloxy)-3-(2-naphthyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 5 mg (18 μmol) of [1R-(1α,2β,4α,4aβ,10aβ)]-9-methylene-1,2,3,4,4a, 9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(2-naphthyl)-2-azetidinone, which has been produced analogously to the process that is described in Tetrahedron 1992 on page 6985 ff. After working-up and purification, 8 mg (11 μmol, 61%) of the title compound is isolated as a colorless oil.

$^1$H-NMR (CDCl$_3$): δ=0.71–1.35 (34H), 1.51 (1H), 2.11 (1H), 2.61 (1H), 2.75 (1H), 3.12 (1H), 4.14 (1H), 4.73 (1H), 4.83 (1H), 5.04 (1H), 5.40 (1H), 5.53 (1H), 6.55 (1H), 7.22–7.86 (10H), 7.93 (1H) ppm.

EXAMPLE 6
[1R-[1α,2B(2R*,3S*),4α,4aβ,10aβ]]-3-(Ethoxycarbonyl) amino-2-hydroxy-3-(4-chlorophenyl)-propanoic acid-9-methylene-1,2,3,4,4a,9,10,10a-octahydro-1,12,12-trimethyl-4a,10a-epoxy-1,4-methanophenanthren-2-ylester 14 mg (20 μmol) of the compound that is presented according to Example 6a is reacted analogously to Example 1. After working-up and purification, 8.7 mg (16 μmol, 79%) of the title compound is isolated as a colorless oil.

$^1$H-NMR (CDCl$_3$): δ=0.84 (3H), 0.92 (3H), 1.06 (3H), 1.21 (3H), 1.68 (1H), 2.30 (1H), 2.71 (1H), 2.79 (1H), 3.12 (1H), 3.16 (1H), 4.10 (2H), 4.51 (1H), 4.92 (1H), 5.05 (1H), 5.23 (1H), 5.53 (1H), 6.40 (1H), 7.20–7.38 (4H), 7.42 (2H), 7.50 (1H), 7.56 (1H) ppm.

EXAMPLE 6a
[1R-[1α,βB(2R*,3S*),4α,4aβ,10aβ]]-3-(Ethoxycarbonyl) amino-2-(triisopropylsilyloxy)-3-(4-chlorophenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 10 mg (35 μmol) of [1R-(1α,2β,4α,4aβ,10aβ)]-9-methylene-1,2,3,4,4a, 9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(4-chlorophenyl)-2-azetidinone, which has been produced analogously to the process that is described in Tetrahedron 1992 on page 6985 ff. After working-up and purification, 14 mg (20 μmol, 56%) of the title compound is isolated as a colorless oil.

$^1$H-NMR (CDCl$_3$): δ=0.82 (3H), 0.90 (3H), 0.86–1.32 (27H), 1.45 (1H), 2.20 (1H), 2.63 (1H), 2.75 (1H), 3.11 (1H), 4.11 (2H), 4.64 (1H), 4.87 (1H), 5.03 (1H), 5.21 (1H), 5.51 (1H), 6.45 (1H), 7.18–7.60 (8H) ppm.

EXAMPLE 7
[1R-[1α,2B(2R*,3S*),4α,4aβ,10aβ]]-3-(Ethoxycarbonyl) amino-2-hydroxy-3-(4-trifluoromethylphenyl)-propanoic acid-9-methylene-1,2,3,4,4a,9,10,10a-octahydro-1,12,12-trimethyl-4a,10a-epoxy-1,4-methanophenanthren-2-ylester 13 mg (18 μmol) of the compound that is presented according to Example 7a is reacted analogously to Example 1. After working-up and purification, 8.2 mg (14 μmol, 78%) of the title compound is isolated as a colorless oil.

$^1$H-NMR (CDCl$_3$): δ=0.85 (3H), 0.93 (3H), 1.07 (3H), 1.22 (3H), 1.68 (1H), 2.31 (1H), 2.73 (1H), 2.79 (1H), 3.13 (1H), 3.20 (1H), 4.12 (2H), 4.56 (1H), 4.92 (1H), 5.06 (1H), 5.32 (1H), 5.53 (1H), 6.44 (1H), 7.32 (2H), 7.43–7.68 (6H) ppm.

EXAMPLE 7a
[1R-[1α,2B(2R*,3S*),4α,4aβ,10aβ]]-3-(Ethoxycarbonyl) amino-2-(triisopropylsilyloxy)-3-(4-trifluoromethylphenyl)-propanoic acid-9-methylene-1,2,3,4, 4a,9,10,10a-octahydro-1,12,12-trimethyl-4a,10a-epoxy-1,4-methanophenanthren-2-ylester By analogy with Example 1a, 7 mg (25 μmol) of [1R-(1α, 2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-

(ethoxycarbonyl)-3-triisopropylsilyloxy-4-(4-trifluoromethylphenyl)-2-azetidinone, which has been produced analogously to the process that is described in Tetrahedron 1992 on page 6985 ff. After working-up and purification, 9 mg (12 μmol, 49%) of the title compound is isolated as a colorless oil.

$^1$H-NMR (CDCl$_3$): δ=0.82 (3H), 0.89 (3H), 0.85–1.30 (30H), 1.42 (1H), 2.19 (1H), 2.64 (1H), 2.76 (1H), 3.10 (1H), 4.12 (2H), 4.68 (1H), 4.86 (1H), 5.03 (1H), 5.29 (1H), 5.52 (1H), 6.48 (1H), 7.30 (2H), 7.41–7.68 (6H) ppm.

EXAMPLE 8

[1R-[1α,2B(2R*,3S*),4α,4aβ,10aβ]]-3-(Ethoxycarbonyl)amino-2-hydroxy-3-(4-benzyloxyphenyl)-propanoic acid-9-methylene-1,2,3,4,4a9,10,10a-octahydro-1,12,12,-trimethyl-4a,10a-epoxy-1,4-methanophenanthren-2-ylester 6 mg (7.7 μmol) of the compound that is presented according to Example 8a is reacted analogously to Example 1. After working-up and purification, 3.7 mg (5.9 μmol, 77%) of the title compound is isolated as a colorless oil.

$^1$H-NMR (CDCl$_3$): δ=0.84 (3H), 0.92 (3H), 1.06 (3H), 1.22 (3H), 1.74 (1H), 2.30 (1H), 2.71 (1H), 2.78 (1H), 3.11 (1H), 3.15 (1H), 4.10 (2H), 4.52 (1H), 4.92 (1H), 5.01 (2H), 5.06 (1H), 5.21 (1H), 5.53 (1H), 6.34 (1H), 6.89 (2H), 7.27–7.44 (9H), 7.49 (1H), 7.55 (1H) ppm.

EXAMPLE 8a

[1R-[1α,2B(2R*,3S*),4α,4aβ,10aβ]]-3-(Ethoxycarbonyl)amino-2-(triisopropylsilyloxy)-3-(4-benzyloxyphenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 11 mg (40 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(4-benzyloxyphenyl)-2-azetidinone, which has been produced analogously to the process that is described in Tetrahedron 1992 on page 6985 ff. After working-up and purification, 29 mg (37 μmol, 93%) of the title compound is isolated as a colorless oil.

$^1$H-NMR (CDCl$_3$): δ=0.82 (3H), 0.85–1.29 (30H), 1.50 (1H), 2.18 (1H), 2.62 (1H, 2.74 (1H), 3.11 (1H), 4.11 (2H), 4.63 (1H), 4.88 (1H), 5.02 (3H), 5.19 (1H), 5.51 (1H), 6.40 (1H), 6.85 (2H), 7.22–7.49 (10H), 7.53 (1H) ppm.

EXAMPLE 9

[1R-[1α,2B(2R*,3S*),4α,4aβ,9β,10aβ]]-3-(Ethoxycarbonyl)amino-2-hydroxy-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester 30 mg (37 μmol) of the compound that is presented according to Example 9a is reacted analogously to Example 1. After working-up and purification, 11 mg (21 μmol, 56%) of the title compound is isolated as a colorless oil.

$^1$H-NMR (CDCl$_3$): δ=0.78 (3H), 0.89 (3H), 1.01 (3H), 1.71 (3H), 1.40 (3H), 1.72 (1H), 2.08 (1H), 2.20 (1H), 2.29 (1H), 2.68 (1H), 3.06 (1H), 3.21 (1H), 4.06 (2H), 4.50 (1H), 4.92 (1H), 5.18 (1H), 5.51 (1H), 6.29 (1H), 6.68 (2H), 7.11–7.39 (5H), 7.48 (1H) ppm.

EXAMPLE 9a

[1R-[1α,2β(2R*,3S*),4α,4aβ,9β,10aβ]]-3-(Ethoxycarbonyl)amino-2-(triisopropylsilyloxy)-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester 120 mg (149 μmol) of compound A that is presented according to Example 3a is dissolved in 6 ml or ethanol, mixed with 12 mg of palladium on carbon (10%) and hydrogenated at 1 atm below an atmosphere that consists of hydrogen. After the theoretically calculated amount is taken up, catalyst is filtered out, the filtrate is concentrated by evaporation, and the residue that is obtained is purified by chromatography on about 40 ml of fine silica gel. A mixture of n-hexane and ethyl acetate is used as a mobile solvent. 89 mg (110 μmol, 74%) of the title compound is isolated as a colorless oil.

$^1$H-NMR (CDCl$_3$): δ=0.14 (6H), 0.73 (3H), 0.79–1.29 (40H), 1.40 (3H), 1.44 (1H), 2.03 (1H), 2.17 (1H), 2.58 (1H), 3.04 (1H), 4.10 (2H), 4.62 (1H), 4.87 (1H), 5.21 (1H), 6.23 (1H), 6.72 (2H), 7.10–7.37 (5H), 7.43 (1H) ppm.

EXAMPLE 10

[1R-[1α,2β(2R*,3S*),4α,4aβ,10aβ]]-3-(Ethoxycarbonyl)amino-2-hydroxy-3-(3-methylphenyl)-propanoic acid-9-methyl-1,2,3,4,4a,9,10,10a-octahydro-1,12,12-trimethyl-4a,10a-epoxy-1,4-methanophenanthren-2-ylester 6 mg (11 μmol) of the compound that is presented according to Example 4 is reacted analogously to Example 9a. After working-up and purification, 3 mg (5.6 μmol, 51%) of the title compound is isolated as a colorless oil.

$^1$H-NMR (CDCl$_3$): δ=0.79 (3H), 0.90 (3H), 1.03 (3H), 1.20 (3H), 1.40 (3H), 1.55 (1H), 1.73 (1H), 2.08 (1H), 2.21 (1H), 2.27 (3H), 2.68 (1H), 3.09 (1H), 3.12 (1H), 4.08 (2H), 4.51 (1H), 4.91 (1H), 5.23 (1H), 6.27 (1H), 7.05 (1H), 7.13–7.40 (6H), 7.49 (1H) ppm.

EXAMPLE 11

[1R-[1α,2β(2R*,3S*),4α,4aβ,9β,10aβ]]-3-(Ethoxycarbonyl)amino-2-hydroxy-3-(4-chlorophenyl)-propanoic acid-9-methyl-1,2,3,4,4a,9,10,10a-octahydro-1,12,12-trimethyl-4a,10a-epoxy-1,4-methanophenanthren-2-ylester 2.8 mg (3.9 μmol) of the compound that is presented according to Example 11a is reacted analogously to Example 1. After working-up and purification, 2.0 mg (3.6 μmol, 93%) of the title compound is isolated as a colorless oil.

$^1$H-NMR (CDCl$_3$): δ=0.78 (3H), 0.90 (3H), 1.02 (3H), 1.19 (3H), 1.40 (3H), 1.67 (1H), 2.09 (1H), 2.20 (1H), 2.29 (1H), 2.68 (1H), 3.07 (1H), 3.19 (1H), 4.09 (2H), 4.52 (1H), 4.91 (1H), 5.23 (1H), 6.30 (1H), 7.12–7.33 (5H), 7.40–7.55 (3H) ppm.

EXAMPLE 11a

[1R-[1α,2β(2R*,3S*),4α,4aβ,9β,10aβ]]-3-(Ethoxycarbonyl)amino-2-(triisopropylsilyloxy)-3-(4-chlorophenyl)-propanoic acid-9-methyl-1,2,3,4,4a,9,10,10a-octahydro-1,12,12-trimethyl-4a,10a-epoxy-1,4-methanophenanthren-2-ylester 8 mg (11 μmol) of the compound that is presented according to Example 6a is reacted analogously to Example 9a. After working-up and purification, 2.8 mg (3.9 μmol, 36%) of the title compound is isolated as a colorless oil.

$^1$H-NMR (CDCl$_3$): δ=0.74 (3H), 0.79–1.31 (30H), 1.40 (3H), 1.50 (1H), 2.06 (1H), 2.15 (1H), 2.19 (1H), 2.60 (1H), 3.05 (1H), 4.09 (2H), 4.63 (1H), 4.85 (1H), 5.23 (1H), 6.34 (1H), 7.10–7.50 (8H) ppm.

EXAMPLE 12

[1R-[1α,2β(2R*,3S*),4α,4aβ,9β,10aβ]]-3-(Ethoxycarbonyl)amino-2-hydroxy-3-(4-trifluoromethylphenyl)-propanoic acid-9-methyl-1,2,3,4,4a,9,10,10a-octahydro-1,12,12-trimethyl-4a,10a-epoxy-1,4-methanophenanthren-2-ylester 4.5 mg (6 μmol) of the compound that is presented according to Example 12a is reacted analogously to Example 1. After working-up and purification, 3.2 mg (5.4 μmol, 91%) of the title compound is isolated as a colorless oil.

$^1$H-NMR (CDCl$_3$): δ=0.78 (3H), 0.89 (3H), 1.02 (3H), 1.19 (3H), 1.40 (3H), 1.65 (1H), 2.10 (1H), 2.21 (1H), 2.29 (1H), 2.68 (1H), 3.07 (1H), 3.22 (1H), 4.10 (2H), 4.54 (1H), 4.91 (1H), 5.32 (1H), 6.35 (1H), 7.12–7.34 (3H), 7.44–7.69 (5H) ppm.

EXAMPLE 12a

[1R-[1α,2β(2R*,3S*),4α,4aβ,9β,10aβ]]-3-(Ethoxycarbonyl)amino-2-(triisopropylsilyloxy)-3-(4-trifluoromethylphenyl)-propanoic acid-9-methyl-1,2,3,4,4a,9,10,10a-octahydro-1,12,12-trimethyl-4a,10a-epoxy-1,4-methanophenanthren-2-ylester 9 mg (12 μmol) of the compound that is presented according to Example 7a is reacted analogously to Example 9a. After working-up and purification, 4.5 mg (6.0 μmol, 50%) of the title compound is isolated as a colorless oil.

$^1$H-NMR (CDCl$_3$): δ=0.73 (3H), 0.82–1.30 (31H), 1.41 (4H), 2.06 (1H), 2.18 (1H), 2.60 (1H), 3.06 (1H), 4.10 (2H), 4.67 (1H), 4.85 (1H), 5.31 (1H), 6.37 (1H), 7.10–7.32 (3H), 7.49–7.67 (5H) ppm.

EXAMPLE 13

[1R-[1α,2β(2R*,3S*),4α,4aβ,9β,10aβ]]-3-(Ethoxycarbonyl)amino-2-hydroxy-3-(4-benzyloxyphenyl)-propanoic acid-9-methyl-1,2,3,4,4a,9,10,10a-octahydro-1,12,12-trimethyl-4a,10a-epoxy-1,4-methanophenanthren-2-ylester 7 mg (9 μmol) of the compound that is presented according to Example 13a is reacted analogously to Example 1. After working-up and purification, 4.5 mg (7.2 μmol, 80%) of the title compound is isolated as a colorless oil.

$^1$H-NMR (CDCl$_3$): δ=0.79 (3H), 0.89 (3H), 1.02 (3H), 1.20 (3H), 1.40 (3H), 1.71 (1H), 2.08 (1H), 2.21 (1H), 2.28 (1H), 2.67 (1H), 3.07 (1H), 3.16 (1H), 4.09 (2H), 4.51 (1H), 4.90 (1H), 5.02 (2H), 5.21 (1H), 6.26 (1H), 6.90 (2H), 7.12–7.55 (11H) ppm.

EXAMPLE 13a

[1R-[1α,2β(2R*,3S*),4α,4aβ,9β,10aβ]]-3-(Ethoxycarbonyl)amino-2-(triisopropylsilyloxy)-3-(4-benzyloxyphenyl)-propanoic acid-9-methyl-1,2,3,4,4a,9,10,10a-octahydro-1,12,12-trimethyl-4a,10a-epoxy-1,4-methanophenanthren-2-ylester 23 mg (30 μmol) of the compound that is presented according to Example 8a is reacted analogously to Example 9a. After working-up and purification, 7 mg (9.0 μmol, 30%) of the title compound is isolated as a colorless oil.

$^1$H-NMR (CDCl$_3$): δ=0.73 (3H), 0.87 (3H), 0.90–1.30 (28H), 1.41 (3H), 1.50 (1H), 2.04 (1H), 2.18 (1H), 2.58 (1H), 3.05 (1H), 4.09 (2H), 4.62 (1H), 4.85 (1H), 5.02 (2H), 5.21 (1H), 6.28 (1H), 6.87 (2H), 7.08–7.52 (11H) ppm.

EXAMPLE 14

[1R-[1α,2β[2R*,3S*(4S*)],4α,4aβ,9β,10aβ]]-3-(Ethoxycarbonyl)amino-2-triisopropylsilyloxy-3-[4-(4-(1-methylethylene)cyclohex-1-ene-carbonyloxy)phenyl]-propanoic acid-9-methyl-1,2,3,4,4a,9,10,10a-octahydro-1,12,12-trimethyl-4a,10a-epoxy-1,4-methanophenanthren-2-ylester 10 mg (19 μmol) of the compound that is presented according to Example 9 is dissolved in 0.3 ml of anhydrous dichloromethane, mixed at 0° C. under an atmosphere of dry argon with 2.6 μl of triethylamine, with a molar equivalent of a solution of L-(–)-perillic acid chloride in dichloromethane and allowed to stir for 3 hours. It is poured into a saturated sodium bicarbonate solution, extracted with dichloromethane, and the organic phase is dried on sodium sulfate. The residue that is obtained after filtration and removal of the solvent is purified by chromatography on an analytical thin-layer plate. A mixture of n-hexane and ethyl acetate is used as a mobile solvent; a mixture of diethyl ether in 2-propanol is used as an eluant. 3 mg (4.4 μmol, 23%) of the title compound is isolated as a colorless oil.

$^1$H-NMR (CDCl$_3$): δ=0.78 (3H), 0.89 (3H), 1.02 (3H), 1.19 (3H), 1.40 (3H), 1.53 (1H), 1.71 (1H), 1.77 (3H), 1.94 (1H), 2.08 (1H), 2.13–2.49 (6H), 2.57 (1H), 2.67 (1H), 3.07 (1H), 3.22 (1H), 4.10 (2H), 4.52 (1H), 4.77 (2H), 4.91 (1H), 5.28 (1H), 6.26 (1H), 7.03 (2H), 7.12–7.31 (4H), 7.41–7.59 (3H) ppm.

EXAMPLE 15

[1R-[1α,2β[2R*,3S*(4S*)],4α,4aβ,9β,10aβ]]-3-(Ethoxycarbonyl)amino-2-hydroxy-3-[4-(diethoxyphosphinyloxy)phenyl]-propanoic acid-9-methyl-1,2,3,4,4a,9,10,10a-octahydro-1,12,12-trimethyl-4a,10a-epoxy-1,4-methanophenanthren-2-ylester 1.6 mg (1.9 μmol) of the compound that is presented according to Example 15a is reacted analogously to Example 1. After working-up and purification, 0.9 mg (1.3 μmol, 71%) of the title compound is isolated as a colorless oil.

$^1$H-NMR (CDCl$_3$): δ=0.78 (3H), 0.89 (3H), 1.01 (3H), 1.19 (3H), 1.32 (6H), 1.40 (3H), 1.69 (1H), 2.08 (1H), 2.20 (1H), 2.27 (1H), 2.67 (1H), 3.07 (1H), 3.15 (1H), 4.09 (2H), 4.18 (4H), 4.51 (1H), 4.91 (1H), 5.25 (1H), 6.26 (1H), 7.10–7.32 (5H), 7.43–7.53 (3H) ppm.

EXAMPLE 15a

[1R-[1α,2β[2R*,3S*(4S*)],4α,4aβ,9β,10aβ]]-3-(Ethoxycarbonyl)amino-2-(triisopropylsilyloxy)-3-[4-(diethoxyphosphinyloxy)phenyl]-propanoic acid-9-methyl-1,2,3,4,4a,9,10,10a-octahydro-1,12,12-trimethyl-4a,10a-epoxy-1,4-methanophenanthren-2-ylester The solution of 4.4 mg (6.4 μmol) of the compound, presented according to Example 9a, in 0.2 ml of anhydrous dimethylformamide is mixed at 0° C. under an atmosphere of dry argon with 0.3 mg of a 55% sodium hydride dispersion and, after 30 minutes, with 1.1 μl of phosphoric acid diethyl ester chloride. It is stirred for 5 hours at 23° C., equal quantities of sodium hydride and phosphoric acid diethyl ester chloride are added again and stirred for another hour. It is poured into saturated sodium chloride solution, extracted with diethyl ether and dried on magnesium sulfate. The residue that is obtained after filtration and removal of the solvent is separated by chromatography on an analytical thin-layer plate. A mixture of n-hexane and ethyl acetate is used as a mobile solvent; a mixture of diethyl ether in 2-propanol is used as an eluant. 1.6 mg (1.9 μmol, 30%) of the title compound is obtained as a colorless oil.

$^1$H-NMR (CDCl$_3$): δ=0.73 (3H), 0.78–1.37 (37H), 1.40 (3H), 1.51 (1H), 2.05 (1H), 2.18 (1H), 2.59 (1H), 3.04 (1H), 4.09 (2H), 4.17 (4H), 4.63 (1H), 4.85 (1H), 5.25 (1H), 6.30 (1H), 7.06–7.30 (5H), 7.38–7.52 (3H) ppm.

EXAMPLE 16

[1R-[1α,2β(2R*,3S*),4α,4aβ,9β,10aβ]]-3-
(Ethoxycarbonyl)amino-2-hydroxy-3-(4-
fluorophenyl)-propanoic acid-9-methyl-1,2,3,4,4a,9,
10,10a-octahydro-1,12,12-trimethyl-4a,10a-epoxy-1,
4-methanophenanthren-2-ylester (A) and

[1S-[1α,2β(2R*,3S*),4α,4aβ,10aβ]]-3-
(ethoxycarbonyl)amino-2-hydroxy-3-(4-
fluorophenyl)-propanoic acid-9-methylene-1,2,3,4,
4a,9,10,10a-octahydro-1,12,12-trimethyl-4a,10a-
epoxy-1,4-methanophenanthren-2-ylester (B)

13 mg (18.7 μmol) of the compounds that are presented according to Example 15a is reacted analogously to Example 1. After working-up and purification, 4.5 mg (8.4 μmol, 45%) of title compound A as well as 3.0 mg (5.6 μmol, 30%) of title compound B are isolated, in each case as a colorless oil.

$^1$H-NMR (CDCl$_3$) of A: δ=0.77 (3H), 0.89 (3H), 1.02 (3H), 1.20 (3H), 1.40 (3H), 1.66 (1H), 2.08 (1H), 2.21 (1H), 2.28 (1H), 2.68 (1H), 3.07 (1H), 3.18 (1H), 4.09 (2H), 4.51 (1H), 4.90 (1H), 5.25 (1H), 6.29 (1H), 6.98 (2H), 7.13–7.33 (3H), 7.41–7.56 (3H) ppm.

$^1$H-NMR (CDCl$_3$) of B: δ=0.78 (3H), 0.91 (3H), 0.95 (3H), 1.20 (3H), 1.38 (3H), 1.82 (1H), 2.02 (1H), 2.23 (1H), 2.33 (1H), 2.68 (1H), 3.05 (1H), 3.23 (1H), 4.09 (2H), 4.51 (1H), 5.15 (1H), 5.30 (1H), 5.88 (1H), 7.03 (2H), 7.12–7.31 (3H), 7.36–7.50 (3H) ppm.

EXAMPLE 16a

[1R-[1α,2β(2R*,3S*),4α,4aβ,9β,10aβ]]-3-
(Ethoxycarbonyl)amino-2-(triisopropylsilyloxy)-3-
(4-fluorophenyl)-propanoic acid-9-methyl-1,2,3,4,
4a,9,10,10a-octahydro-1,12,12-trimethyl-4a,10a-
epoxy-1,4-methanophenanthren-2-ylester and

[1S-[1α,2β(2R*,3S*),4α,4aβ,10aβ]]-3-
(ethoxycarbonyl)amino-2-(triisopropylsilyloxy)-3-
(4-fluorophenyl)-propanoic acid-9-methylene-1,2,3,
4,4a,9,10,10a-octahydro-1,12,12-trimethyl-4a,10a-
epoxy-1,4-methanophenanthren-2-ylester 21 mg (30 μmol) of the compounds that are presented according to Example 2a is reacted analogously to Example 9a. After working-up and purification, 13 mg (18.7 μmol, 62%) of the title compounds, which are further reacted without separation, is isolated as a colorless oil.

EXAMPLE 17

[1R-[1α,2β(2R*,3S*),4α,4aβ,9β,10aβ]]-3-
(Ethoxycarbonyl)amino-2-hydroxy-3-(4-
methoxyphenyl)-propanoic acid-9-methyl-1,2,3,4,
4a,9,10,10a-octahydro-1,12,12-trimethyl-4a,10a-
epoxy-1,4-methanophenanthren-2-ylester 43 mg (61 μmol) of the compound that is presented according to Example 17a is reacted analogously to Example 1. After working-up and purification, 25 mg (45 μmol, 75%) of the title compound is isolated as a colorless oil.

$^1$H-NMR (CDCl$_3$): δ=0.78 (3H), 0.88 (3H), 1.02 (3H), 1.18 (3H), 1.40 (3H), 1.73 (1H), 2.08 (1H), 2.22 (1H), 2.29 (1H), 2.67 (1H), 3.07 (1H), 3.15 (1H), 3.75 (3H), 4.09 (2H), 4.50 (1H), 4.91 (1H), 5.21 (1H), 6.26 (1H), 6.82 (2H), 7.14–7.23 (3H), 7.42 (2H), 7.50 (1H) ppm.

EXAMPLE 17a

[1R-[1α,2β(2R*,3S*),4α,4aβ,9β,10aβ]]-3-
(Ethoxycarbonyl)amino-2-(triisopropylsilyloxy)-3-
(4-methoxyphenyl)-propanoic acid-9-methyl-1,2,3,4,
4a,9,10,10a-octahydro-1,12,12-trimethyl-4a,10a-
epoxy-1,4-methanophenanthren-2-ylester 66 mg (94 μmol) of the compound that is presented according to Example 1a is reacted analogously to Example 9a. After working-up and purification, 43 mg (61 μmol, 65%) of the title compound is isolated as a colorless oil.

$^1$H-NMR (CDCl$_3$): δ=0.75 (3H), 0.86 (3H), 0.90–1.25 (27H), 1.41 (3H), 1.51 (1H), 2.05 (1H), 2.18 (2H), 2.58 (1H), 3.04 (1H), 3.75 (3H), 4.09 (2H), 4.62 (1H), 4.86 (1H), 5.21 (1H), 6.28 (1H), 6.80 (2H), 7.11–7.50 (6H) ppm.

EXAMPLE 18

[1R-[1α,2β(2R*,3S*),4α,4aβ,10aβ]]-3-
(Ethoxycarbonyl)amino-2-hydroxy-3-(3-thienyl)-
propanoic acid-9-methylene-1,2,3,4,4a,9,10,10a-
octahydro-1,12,12trimethyl-4a,10a-epoxy-1,4-
methanophenanthren-2-ylester 20 mg (29 μmol) of the compound that is presented according to Example 18a is reacted analogously to Example 1. After working-up and purification, 8.5 mg (16 μmol, 56%) of the title compound is isolated as a colorless oil.

$^1$H-NMR (CDCl$_3$): δ=0.83 (3H), 0.91 (3H), 1.08 (3H), 1.26 (3H), 1.53 (1H), 2.26 (1H), 2.68 (1H), 2.78 (1H), 3.15 (1H), 3.24 (1H), 4.15 (2H), 4.50 (1H), 4.89 (1H), 5.05 (1H), 5.34 (1H), 5.53 (1H), 6.40 (1H), 7.21 (2H), 7.28–7.40 (3H), 7.50 (1H), 7.56 (1H), ppm.

EXAMPLE 18a

[1R-[1α,2β(2R*,3S*),4α,4aβ,10aβ]]-3-
(Ethoxycarbonyl)amino-2-(triisopropylsilyloxy)-3-
(3-thienyl)-propanoic acid-9-methylene-1,2,3,4,4a,9,
10,10a-octahydro-1,12,12-trimethyl-4a,10a-epoxy-1,
4-methanophenanthren-2-ylester By analogy with Example 1a, 30 mg (106 μmol) of [1R-(1α,2β,4α,4aβ,10aβ)]-9-methylene-1,2,3,4,4a,9,10, 10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(3-thienyl)-2-azetidinone, which has been produced analogously to the process that is described in Tetrahedron 1992 on page 6985 ff. After working-up and purification, 66 mg (97 μmol, 92%) of the title compound is isolated as a colorless oil.

$^1$H-NMR (CDCl$_3$): δ=0.78 (3H), 0.85 (3H), 0.96–1.30 (28H), 2.11 (1H), 2.58 (1H), 2.74 (1H), 3.12 (1H), 4.17 (2H), 4.62 (1H), 4.82 (1H), 5.03 (1H), 5.28 (1H), 5.53 (1H), 6.66 (1H), 7.18 (1H), 7.22–7.36 (4H), 7.44 (1H), 7.55 (1H) ppm.

EXAMPLE 19

[1R-[1α,2β(2R*,3S*),4α,4aβ,9β,10aβ]]-3-
(Ethoxycarbonyl)amino-2-hydroxy-3-(3-thienyl)-
propanoic acid-9-methyl-1,2,3,4,4a,9,10,10a-
octahydro-1,12,12-trimethyl-4a,10a-epoxy-1,4-
methanophenanthren-2-ylester 15 mg (22 μmol) of the compound that is presented according to Example 19a is reacted analogously to Example 1. After working-up and purification, 8.9 mg (17 μmol), 77%) of the title compound is isolated as a colorless oil.

$^1$H-NMR (CDCl$_3$): δ=0.77 (3H), 0.88 (3H), 1.02 (3H), 1.23 (3H), 1.41 (3H), 1.50 (1H), 2.08 (1H), 2.23 (2H), 2.64 (1H), 3.08 (1H), 3.28 (1H), 4.13 (2H), 4.50 (1H), 4.86 (1H), 5.35 (1H), 6.28 (1H), 7.13–7.33 (5H), 7.42 (1H), 7.49 (1H) ppm.

EXAMPLE 19a

[1R-[1α,2β(2R*,3S*),4α,4aβ,9β,10aβ]]-3-(Ethoxycarbonyl)amino-2-(triisopropylsilyloxy)-3-(3-thienyl)-propanoic acid-9-methyl-1,2,3,4,4a,9,10,10a-octahydro-1,12,12-trimethyl-4a,10a-epoxy-1,4-methanophenanthren-2-ylester 40 mg (59 μmol) of the compound that is presented according to Example 18a is reacted analogously to Example 9a. After working-up and purification, 15 mg (22 μmol, 37%) of the title compound is isolated as a colorless oil.

$^1$H-NMR (CDCl$_3$): δ=0.72 (3H), 0.79–1.30 (31H), 1.42 (3H), 2.05 (2H), 2.21 (1H), 2.53 (1H), 3.05 (1H), 4.15 (2H), 4.62 (1H), 4.82 (1H), 5.30 (1H), 6.48 (1H), 7.10–7.31 (5H), 7.34 (1H), 7.45 (1H) ppm.

EXAMPLE 20

[1R-[1α,2β[2R*,3S*(4R*)],4α,4aβ,9β,10aβ]]-3-(Ethoxycarbonyl)amino-2hydroxy-3-[4-(4-(1-methylethylene)cyclohex-1-ene-carbonyloxy) phenyl]-propanoic acid-9-methyl-1,2,3,4,4a,9,10,10a-octahydro-1,12,12-trimethyl-4a,10a-epoxy-1,4-methanophenanthren-2-ylester 4.2 mg (5.0 μmol) of compound A, presented according to Example 20a, is reacted analogously to Example 1. After working-up and purification, 1.9 mg (2.8 μmol, 56%) of the title compound is isolated as a colorless oil.

$^1$H-NMR (CDCl$_3$): δ=0.78 (3H), 0.89 (3H), 1.03 (3H), 1.20 (3H), 1.40 (3H), 1.71 (1H), 1.78 (3H), 1.95 (1H), 2.09 (1H), 2.14–2.48 (7H), 2.58 (1H), 2.68 (1H), 3.08 (1H), 3.22 (1H), 4.10 (2H), 4.53 (1H), 4.78 (1H), 4.92 (1H), 5.29 (1H), 6.28 (1H), 7.05 (2H), 7.13–7.35 (5H), 7.41–7.60 (3H) ppm.

EXAMPLE 20a

[1R-[1α,2β[2R*,3S*(4R*)],4α,4aβ,9β,10aβ]]-3-(Ethoxycarbonyl)amino-2-triisopropylsilyloxy-3-[4-(4-(1-methylethylene)cyclohex-1-ene-carbonyloxy) phenyl]-propanoic acid-9-methyl-1,2,3,4,4a,9,10,10a-octahydro-1,12,12-trimethyl-4a,10a-epoxy-1,4-methanophenanthren-2-ylester (A) and [1R-[1α,2β[2R*,3S*],4α,4aβ,9β,10aβ]]-3-(ethoxycarbonyl)amino-2-triisopropylsilyloxy-3-[4-(4-(1-methylethylidene)cyclohex-1-ene-carbonyloxy) phenyl]-propanoic acid-9-methyl-1,2,3,4,4a,9,10,10a-octahydro-1,12,12-trimethyl-4a,10a-epoxy-1,4-methanophenanthren-2-ylester (B)

By analogy with Example 14, 10 mg (14.5 μmol) of the compound that is presented according to Example 20b is reacted using a mixture of R-(+)-perillic acid chloride and 4-(1-methylethylidene)cyclohex-1-ene-carboxylic acid chloride. After working-up and purification, 4.2 mg (5.0 μmol, 33%) of title compound A as well as 3.9 mg (4.6 μmol, 31%) of title compound B are isolated, in each case as a colorless oil.

EXAMPLE 20b

[1R-[1α,2β(2R*,3S*),4α,4aβ,9β,10aβ]]-3-(Ethoxycarbonyl)amino-2-triisopropylsilyloxy-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester 520 mg (750 μmol) of the compound that is presented according to Example 20c is hydrogenated analogously to Example 9a. After working-up and purification, 260 mg (376 μmol, 50%) of the title compound is isolated as a colorless oil.

$^1$H-NMR (CDCl$_3$): δ=0.74 (3H), 0.81–1.31 (30H), 1.40 (3H), 1.52 (1H), 1.99–2.30 (3H), 2.59 (1H), 3.04 (1H), 4.09 (2H), 4.62 (1H), 4.87 (1H), 5.14 (1H), 5.19 (1H), 6.28 (1H), 6.67 (2H), 7.09–7.40 (5H), 7.45 (1H) ppm.

EXAMPLE 20c

[1R-[1α,2β(2R*,3S*),4α,4aβ,10aβ]]-3-(Ethoxycarbonyl)amino-2-triisopropylsilyloxy-3-(4-hydroxyphenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 480 mg (1.7 mmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-hydroxy-4-[4-(tert-butyldimethylsilyloxy)phenyl]-2-azetidinone, which has been produced analogously to the process that is described in Tetrahedron 1992 on page 6985 ff. After working-up and purification, 531 mg (0.77 mmol, 45%) of the title compound is isolated as a colorless oil.

$^1$H-NMR (CDCl$_3$): δ=0.82 (3H), 0.85–1.40 (30H), 1.54 (1H), 2.20 (1H), 2.63 (1H), 2.73 (1H), 3.10 (1H), 4.09 (2H), 4.63 (1H), 4.90 (1H), 5.02 (1H), 5.14 (1H), 5.49 (1H), 5.76 (1H), 6.37 (1H), 6.57 (2H), 7.16–7.35 (4H), 7.46 (1H), 7.52 (1H) ppm.

EXAMPLE 21

[1R-[1α,2β[2R*,3S*],4α,4aβ,9β,10aβ]]-3-(Ethoxycarbonyl)amino-2-hydroxy-3-[4-(4-(1-methylethylidene)cyclohex-1-ene-carbonyloxy) phenyl]-propanoic acid-9-methyl-1,2,3,4,4a,9,10,10a-octahydro-1,12,12-trimethyl-4a,10a-epoxy-1,4-methanophenanthren-2-ylester 3.9 mg (4.6 μmol) of compound B, presented according to Example 21a, is reacted analogously to Example 1. After working-up and purification, 1.9 mg (2.8 μmol, 59%) of the title compound is isolated as a colorless oil.

$^1$H-NMR (CDCl$_3$): δ=0.78 (3H), 0.90 (3H), 1.03 (3H), 1.20 (3H), 1.40 (3H), 1.60 (3H), 1.63 (3H), 1.71 (1H), 1.82 (1H), 2.00–2.40 (6H), 2.52 (1H), 2.65 (1H), 2.68 (1H), 3.08 (1H), 3.20 (1H), 4.11 (2H), 4.53 (1H), 4.92 (1H), 5.28 (1H), 6.26 (1H), 7.04 (2H), 7.12–7.33 (4H), 7.43–7.59 (3H) ppm.

EXAMPLE 22

[1R-[1α,2β(2R*,3S*),4α,4aβ,9β,10aβ]]-3-(Ethoxycarbonyl)amino-2-hydroxy-3-(3-fluorophenyl)-propanoic acid-9-methyl-1,2,3,4,4a,9,10,10a-octahydro-1,12,12-trimethyl-4a,10a-epoxy-1,4-methanophenanthren-2-ylester 7.8 mg (11 μmol) of the compound that is presented according to Example 22a is reacted analogously to Example 1. After working-up and purification, 4.4 mg (8.2 μmol, 74%) of the title compound is isolated as a colorless oil.

$^1$H-NMR (CDCl$_3$): δ=0.79 (3H), 0.90 (3H), 1.02 (3H), 1.19 (3H), 1.40 (3H), 1.71 (1H), 2.08 (1H), 2.20 (1H), 2.29 (1H), 2.68 (1H), 3.07 (1H), 3.20 (1H), 4.09 (2H), 4.52 (1H), 4.94 (1H), 5.28 (1H), 6.29 (1H), 6.94 (1H), 7.12–7.35 (6H), 7.49 (1H) ppm.

EXAMPLE 22a

[1R-[1α,2β(2R*,3S*),4α,4aβ,9β,10aβ]]-3-(Ethoxycarbonyl)amino-2-triisopropylsilyloxy-3-(3-fluorophenyl)-propanoic acid-9-methyl-1,2,3,4,4a,9,10,10a-octahydro-1,12,12-trimethyl-4a,10a-epoxy-1,4-methanophenanthren-2-ylester 14 mg (20 μmol) of the compound that is presented according to Example 25a is hydrogenated analogously to Example 9a. After working-up and purification, 7.8 mg (11.2 μmol, 56%) of the title compound is isolated as a colorless oil.

EXAMPLE 23

[1R-[1α,2β(2R*,3S*),4α,4aβ,9β,10aβ]]-3-(Ethoxycarbonyl)amino-2-hydroxy-3-(3-chlorophenyl)-propanoic acid-9-methyl-1,2,3,4,4a,9,10,10a-octahydro-1,12,12-trimethyl-4a,10a-epoxy-1,4-methanophenanthren-2-ylester 24 mg (34 μmol) of the compound that is presented according to Example 23a is reacted analogously to Example 1. After working-up and purification, 12.2 mg (22 μmol, 65%) of the title compound is isolated as a colorless oil.

$^1$H-NMR (CDCl$_3$): δ=0.78 (3H), 0.90 (3H), 1.03 (3H), 1.20 (3H), 1.41 (3H), 1.71 (2H), 2.09 (1H), 2.20 (1H), 2.29 (1H), 2.68 (1H), 3.07 (1H), 3.20 (1H), 4.09 (2H), 4.52 (1H), 4.92 (1H), 5.25 (1H), 6.32 (1H), 7.12–7.31 (5H), 7.38 (1H), 7.49 (1H), 7.57 (1H) ppm.

EXAMPLE 23a

[1R-[1α,2β(2R*,3S*),4α,4aβ,9β,10aβ]]-3-(Ethoxycarbonyl)amino-2-triisopropylsilyloxy-3-(3-chlorophenyl)-propanoic acid-9-methyl-1,2,3,4,4a,9,10,10a-octahydro-1,12,12-trimethyl-4a,10a-epoxy-1,4-methanophenanthren-2-ylester 38 mg (54 μmol) of the compound that is presented according to Example 26a is hydrogenated analogously to Example 9a. After working-up and purification, 24 mg (34 μmol, 63%) of the title compound is isolated as a colorless oil.

EXAMPLE 24

[1R-[1α,2β(2R*,3S*),4α,4aβ,9β,10aβ]]-3-(Ethoxycarbonyl)amino-2-hydroxy-3-(4-methylphenyl)-propanoic acid-9-methyl-1,2,3,4,4a,9,10,10a-octahydro-1,12,12-trimethyl-4a,10a-epoxy-1,4-methanophenanthren-2-ylester 4 mg (5.8 μmol) of the compound that is presented according to Example 24a is reacted analogously to Example 1. After working-up and purification, 1.7 mg (3.2 μmol, 55%) of the title compound is isolated as a colorless oil.

$^1$H-NMR (CDCl$_3$): δ=0.79 (3H), 0.89 (3H), 1.02 (3H), 1.19 (3H), 1.40 (3H), 1.78 (1H), 2.09 (1H), 2.22 (1H), 2.31 (4H), 2.68 (1H), 3.06 (1H), 3.12 (1H), 4.08 (2H), 4.52 (1H), 4.91 (1H), 5.22 (1H), 6.26 (1H), 7.05–7.32 (5H), 7.38 (2H), 7.51 (1H) ppm.

EXAMPLE 24a

[1R-[1α,2β(2R*,3S*),4α,4aβ,9β,10aβ]]-3-(Ethoxycarbonyl)amino-2-triisopropylsilyloxy-3-(4-methylphenyl)-propanoic acid-9-methyl-1,2,3,4,4a,9,10,10a-octahydro-1,12,12-trimethyl-4a,10a-epoxy-1,4-methanophenanthren-2-ylester 42 mg (61 μmol) of the compound that is presented according to Example 27a is hydrogenated analogously to Example 9a. After working-up and purification, 4 mg (5.8 μmol, 10%) of the title compound is isolated as a colorless oil.

EXAMPLE 25

[1R-[1α,2β(2R*,3S*),4α,4aβ,10aβ]]-3-(Ethoxycarbonyl)amino-2-hydroxy-3-(3-fluorophenyl)-propanoic acid-9-methylene-1,2,3,4,4a,9,10,10a-octahydro-1,12,12-trimethyl-4a,10a-epoxy-1,4-methanophenanthren-2-ylester 7 mg (10 μmol) of the compound that is presented according to Example 25a is reacted analogously to Example 1. After working-up and purification, 3 mg (5.6 μmol, 56%) of the title compound is isolated as a colorless oil.

$^1$H-NMR (CDCl$_3$): δ=0.85 (3H), 0.93 (3H), 1.07 (3H), 1.22 (3H), 1.72 (1H), 2.31 (1H), 2.72 (1H), 2.79 (1H), 3.12 (1H), 3.16 (1H), 4.11 (2H), 4.52 (1H), 4.94 (1H), 5.06 (1H), 5.27 (1H), 5.52 (1H), 6.39 (1H), 6.92 (1H), 7.15–7.40 (5H), 7.50 (1H), 7.56 (1H) ppm.

EXAMPLE 25a

[1R-[1α,2β(2R*,3S*),4α,4aβ,10aβ]]-3-(Ethoxycarbonyl)amino-2-triisopropylsilyloxy-3-(3-fluorophenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 30 mg (106 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(3-fluorophenyl)-2-azetidinone, which has been produced analogously to the process that is described in Tetrahedron 1992 on page 6985 ff. After working-up and purification, 49 mg (73 μmol, 69%) of the title compound is isolated as a colorless oil.

EXAMPLE 26

[1R-[1α,2β(2R*,3S*),4α,4aβ,10aβ]]-3-(Ethoxycarbonyl)amino-2-hydroxy-3-(3-chlorophenyl)-propanoic acid-9-methylene-1,2,3,4,4a,9,10,10a-octahydro-1,12,12-trimethyl-4a,10a-epoxy-1,4-methanophenanthren-2-ylester 20 mg (28 μmol) of the compound that is presented according to Example 26a is reacted analogously to Example 1. After working-up and purification, 12.4 mg (22 μmol, 80%) of the title compound is isolated as a colorless oil.

¹H-NMR (CDCl₃): δ=0.87 (3H), 0.94 (3H), 1.09 (3H), 1.23 (3H), 1.74 (1H), 2.33 (1H), 2.73 (1H), 2.81 (1H), 3.13 (1H), 3.18 (1H), 4.12 (2H), 4.52 (1H), 4.93 (1H), 5.07 (1H), 5.26 (1H), 5.55 (1H), 6.44 (1H), 7.15–7.42 (5H), 7.45–7.64 (3H) ppm.

EXAMPLE 26a

[1R-[1α,2β(2R*,3S*),4α,4aβ,10aβ]]-3-(Ethoxycarbonyl)amino-2-triisopropylsilyloxy-3-(3-chlorophenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 38 mg (54 μmol) or [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(3-chlorophenyl)-2-azetidinone, which has been produced analogously to the process that is described in Tetrahedron 1992 on page 6985 ff. After working-up and purification, 24 mg (34 μmol, 63%) of the title compound is isolated as a colorless oil.

EXAMPLE 27

[1R-[1α,2β(2R*,3S*),4α,4aβ,10aβ]]-3-(Ethoxycarbonyl)amino-2-hydroxy-3-(4-methylphenyl)-propanoic acid-9-methylene-1,2,3,4,4a,9,10,10a-octahydro-1,12,12-trimethyl-4a,10a-epoxy-1,4-methanophenanthren-2-ylester 20 mg (29 μmol) of the compound that is presented according to Example 27a is reacted analogously to Example 1. After working-up and purification, 9 mg (17 μmol, 58%) of the title compound is isolated as a colorless oil.

¹H-NMR (CDCl₃): δ=0.84 (3H), 0.92 (3H), 1.07 (3H), 1.21 (3H), 1.79 (1H), 2.27 (3H), 2.30 (1H), 2.71 (1H), 2.78 (1H), 3.10 (1H), 3.12 (1H), 4.11 (2H), 4.51 (1H), 4.93 (1H), 5.05 (1H), 5.21 (1H), 5.52 (1H), 6.33 (1H), 7.08 (2H), 7.22–7.41 (4H), 7.45–7.60 (2H) ppm.

EXAMPLE 27a

[1R-[1α,2β(2R*,3S*),4α,4aβ,10aβ]]-3-(Ethoxycarbonyl)amino-2-triisopropylsilyloxy-3-(4-methylphenyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 30 mg (106 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(4-methylphenyl)-2-azetidinone, which has been produced analogously to the process that is described in Tetrahedron 1992 on page 6985 ff. After working-up and purification, 63 mg (92 μmol, 86%) of the title compound is isolated as a colorless oil.

EXAMPLE 28

[1R-[1α,2β(2R*,3S*),4α,4aβ,10aβ]]-3-(Ethoxycarbonyl)amino-2-hydroxy-3-(2-thienyl)-propanoic acid-9-methylene-1,2,3,4,4a,9,10,10a-octahydro-1,12,12-trimethyl-4a,10a-epoxy-1,4-methanophenanthren-2-ylester 5 mg (7.4 μmol) of the compound that is presented according to Example 28a is reacted analogously to Example 1. After working-up and purification, 2.7 mg (5.2 μmol, 69%) of the title compound is isolated as a colorless oil.

¹H-NMR (CDCl₃): δ=0.83 (3H), 0.92 (3H), 1.08 (3H), 1.23 (3H), 1.58 (1H), 2.25 (1H), 2.68 (1H), 2.77 (1H), 3.12 (1H), 3.41 (1H), 4.12 (2H), 4.52 (1H), 4.94 (1H), 5.04 (1H), 5.49 (1H), 5.51 (1H), 6.49 (1H), 6.90 (1H), 7.12 (1H), 7.19 (1H), 7.21–7.37 (2H), 7.48 (1H), 7.55 (1H) ppm.

EXAMPLE 28a

[1R-[1α,2β(2R*,3S*),4α,4aβ,10aβ]]-3-(Ethoxycarbonyl)amino-2-triisopropylsilyloxy-3-(2-thienyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 7.4 mg (26 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(2-thienyl)-2-azetidinone, which has been produced analogously to the process that is described in Tetrahedron 1992 on page 6985 ff. After working-up and purification, 16 mg (24 μmol, 90%) of the title compound is isolated as a colorless oil.

EXAMPLE 29

[1R-[1α,2β(2R*,3S*),4α,4aβ,9β,10aβ]]-3-(Ethoxycarbonyl)amino-2-hydroxy-3-(2-thienyl)-propanoic acid-9-methyl-1,2,3,4,4a,9,10,10a-octahydro-1,12,12-trimethyl-4a,10a-epoxy-1,4-methanophenanthren-2-ylester 5.5 mg (8.1 μmol) of the compound that is presented according to Example 29a is reacted analogously to Example 1. After working-up and purification, 3.4 mg (6.5 μmol, 81%) of the title compound is isolated as a colorless oil.

¹H-NMR (CDCl₃): δ=0.77 (3H), 0.89 (3H), 1.01 (3H), 1.20 (3H), 1.41 (3H), 1.56 (1H), 2.07 (1H), 2.20 (1H), 2.22 (1H), 2.63 (1H), 3.07 (1H), 3.44 (1H), 4.12 (2H), 4.52 (1H), 4.94 (1H), 5.50 (1H), 6.40 (1H), 6.92 (1H), 7.09–7.34 (5H), 7.48 (1H) ppm.

EXAMPLE 29a

[1R-[1α,2β(2R*,3S*),4α,4aβ,9β,10aβ]]-3-(Ethoxycarbonyl)amino-2-triisopropylsilyloxy-3-(2-thienyl)-propanoic acid-9-methyl-1,2,3,4,4a,9,10,10a-octahydro-1,12,12-trimethyl-4a,10a-epoxy-1,4-methanophenanthren-2-ylester 80 mg (118 μmol) of the compound that is presented according to Example 28a is hydrogenated analogously to Example 9a. After working-up and purification, 63 mg (92 μmol, 78%) of the title compound is isolated as a colorless oil.

EXAMPLE 30

[1R-[1α,2β(2R*,3S*),4α,4aβ,10aβ]]-3-(Ethoxycarbonyl)amino-2-hydroxy-3-(3-pyridyl)-propanoic acid-9-methylene-1,2,3,4,4a,9,10,10a-octahydro-1,12,12-trimethyl-4a,10a-epoxy-1,4-methanophenanthren-2-ylester 9 mg (13 μmol) of the compound that is presented according to Example 30a is reacted analogously to Example 1. After working-up and purification, 6.1 mg (12 μmol, 88%) of the title compound is isolated as a colorless oil.

$^1$H-NMR (CDCl$_3$): δ=0.85 (3H), 0.93 (1.08 (3H), 1.22 (3H), 1.68 (1H), 2.32 (1H), 2.72 (1H), 2.80 (1H), 3.13 (1H), 3.30 (1H), 4.12 (2H), 4.55 (1H), 4.92 (1H), 5.05 (1H), 5.31 (1H), 5.54 (1H), 6.50 (1H), 7.13–7.38 (3H), 7.51 (1H), 7.56 (1H), 7.83 (1H), 8.50 (1H), 8.72 (1H) ppm.

EXAMPLE 30a

[1R-[1α,2β(2R*,3S*),4α,4aβ,10aβ]]-3-(Ethoxycarbonyl)amino-2-triisopropylsilyloxy-3-(3-pyridyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 17 mg (60 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(3-pyridyl)-2-azetidinone, which has been produced analogously to the process that is described in Tetrahedron 1992 on page 6985 ff. After working-up and purification, 28 mg (41 μmol, 68%) of the title compound is isolated as a colorless oil.

EXAMPLE 31

[1R-[1α,2β(2R*,3S*),4α,4aβ,9β,10aβ]]-3-(Ethoxycarbonyl)amino-2-hydroxy-3-(3-pyridyl)-propanoic acid-9-methyl-1,2,3,4,4a,9,10,10a-octahydro-1,12,12-trimethyl-4a,10a-epoxy-1,4-methanophenanthren-2-ylester (A) and

[1R-[1α,2β(2R*,3S*),4α,4aβ,9β,10aβ]]-3-(ethoxycarbonyl)amino-2-hydroxy-3-(3-pyridyl)-propanoic acid-9-methyl-1,2,3,4,4a,9,10,10a-octahydro-1,12,12-trimethyl-4a,10a-epoxy-1,4-methanophenanthren-2-ylester (B)

9 mg (13 μmol) of the compound that is presented according to Example 31a is reacted analogously to Example 1. After working-up and purification, 3.5 mg (6.7 μmol, 51%) as a 6:4 mixture of title compounds A and B is isolated as a colorless oil.

$^1$H-NMR (CDCl$_3$): δ=0.78 (1.2H), 0.79 (1.8H), 0.90 (3H), 1.03 (1.8H), 1.08 (1.2H), 1.21 (3H), 1.43 (3H), 1.68 (1H), 2.10 (0.6H), 2.12 (1H), 2.31 (1H), 2.48 (0.4H), 2.7 (0.6H), 2.76 (0.4H), 3.09 (1H), 3.27 (1H), 4.12 (2H), 4.56 (1H), 4.84 (0.4H), 4.92 (0.6H), 5.32 (1H), 6.37 (0.6H), 6.95 (0.4H), 7.12–7.40 (4H), 7.50 (1H), 7.86 (1H), 8.51 (1H), 8.76 (1H) ppm.

EXAMPLE 31a

[1R-[1α,2β(2R*,3S*),4α,4aβ,9ξ,10aβ]]-3-(Ethoxycarbonyl)amino-2-triisopropylsilyloxy-3-(3-pyridyl)-propanoic acid-9-methyl-1,2,3,4,4a,9,10,10a-octahydro-1,12,12-trimethyl-4a,10a-epoxy-1,4-methanophenanthren-2-ylester 19 mg (28 μmol) of the compound that is presented according to Example 30a is hydrogenated analogously to Example 9a. After working-up and purification, 9 mg (13 μmol, 47%) of the title compound is isolated as a colorless oil.

EXAMPLE 32

[1R-[1α,2β(2R*,3S*),4α,4aβ,10aβ]]-3-(Ethoxycarbonyl)amino-2-hydroxy-3-(4-pyridyl)-propanoic acid-9-methylene-1,2,3,4,4a,9,10,10a-octahydro-1,12,12-trimethyl-4a,10a-epoxy-1,4-methanophenanthren-2-ylester 31 mg (46 μmol) of the compound that is presented according to Example 32a is reacted analogously to Example 1. After working-up and purification, 20 mg (39 μmol, 83%) of the title compound is isolated as a colorless oil.

$^1$H-NMR (CDCl$_3$): δ=0.84 (3H), 0.92 (3H), 1.08 (3H), 1.23 (3H), 1.58 (1H), 1.81 (1H), 2.29 (1H), 2.71 (1H), 2.80 (1H), 3.13 (1H), 4.12 (2H), 4.56 (1H), 4.93 (1H), 5.07 (1H), 5.29 (1H), 5.53 (1H), 6.43 (1H), 7.22–7.62 (6H), 8.50 (2H) ppm.

EXAMPLE 32a

[1R-[1α,2β(2R*,3S*),4α,4aβ,10aβ]]-3-(Ethoxycarbonyl)amino-2-triisopropylsilyloxy-3-(4-pyridyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 17 mg (60 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(4-pyridyl)-2-azetidinone, which has been produced analogously to the process that is described in Tetrahedron 1992 on page 6985 ff. After working-up and purification, 31 mg (46 μmol, 76%) of the title compound is isolated as a colorless oil.

EXAMPLE 33

[1R-[1α,2β(2R*,3S*),4α,4aβ,9β,10aβ]]-3-(Ethoxycarbonyl)amino-2-hydroxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 30 mg (44 μmol) of the compound that is presented according to Example 33a is reacted analogously to Example 1. After working-up and purification, 19.6 mg (38 μmol, 85%) of the title compound is isolated as a colorless oil.

$^1$H-NMR (CDCl$_3$): δ=0.78 (3H), 0.90 (3H), 1.02 (3H), 1.19 (3H), 1.41 (3H), 1.54 (1H), 2.02–2.52 (3H), 2.67 (1H), 3.08 (1H), 3.50 (broad, 1H), 4.10 (2H), 4.54 (1H), 4.92 (1H), 5.30 (1H), 6.32 (1H), 7.11–7.57 (6H), 8.52 (2H) ppm.

EXAMPLE 33a

[1R-[1α,2β(2R*,3S*),4α,4aβ,9β,10aβ]]-3-(Ethoxycarbonyl)amino-2-triisopropylsilyloxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 20 mg (70 μmol) of compound A, presented according to Example 33b, is reacted using (3R,4S)-1-(ethoxycarbonyl)-3-triisopropylsilyloxy-4-(4-pyridyl)-2-azetidinone, which has been produced analogously to the process that is described in Tetrahedron 1992 on page 6985 ff. After working-up and purification, 30 mg (44 μmol, 63%) of the title compound is isolated as a colorless oil.

EXAMPLE 33b

[1R-[1α,2β,4α,4aβ,9β,10aβ)]-9-Methyl-1,2,3,4,4a,9,10,10a-octahydro-1,12,12-trimethyl-4a,10a-epoxy-1,4-methanophenanthren-2-ol (A) and [1R-[1α,2β,4α,4aβ,9β,10aβ)]-9-methyl-1,2,3,4,4a,9,10,10a-octahydro-1,12,12-trimethyl-4a,10a-epoxy-1,4-methanophenanthren-2-ol (B)

Variant A

The solution of 622 mg (0.4 mol) of [1R-[1α,2β(2R*,3S*), 4α,4aβ,9β,10aβ]]-3-(methoxycarbonyl)amino-2-

(triisopropylsilyloxy)benzenepropanoic acid-9-methyl-1,2,3,4,4a,9,10,10a-octahydro-1,12,12-trimethyl-4a,10a-epoxy-1,4-methanophenanthren-2-ylester, which has been produced analogously to the process that is described in DE ... (EM 51113), in 9 ml of tetrahydrofuran is mixed at 23° C. with 1.4 ml of a 1M solution of tetrabutylammonium fluoride in tetrahydrofuran, 2.4 ml of a 5% aqueous solution of lithium hydroxide, and it is stirred for 1.5 hours. It is poured into a saturated sodium chloride solution, extracted several times with dichloromethane, the combined organic extracts are washed with saturated sodium chloride solution and dried on sodium sulfate. The residue that is obtained after filtration and removal of the solvent is purified by chromatography on about 70 ml of fine silica gel. A mixture of n-hexane and ethyl acetate is used as a mobile solvent. 230 mg (0.81 mmol), 86%) of title compound A is isolated as a colorless solid.

Variant B

The solution of 500 mg (1.77 mmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol, which has been produced analogously to the process that is described in J. Am. Chem. Soc. 1992, on page 5879 ff, in 8 ml of anhydrous tetrahydrofuran is mixed in portions with a total of 100 mg of tris-triphenylphosphine-rhodium(I) chloride, and it is hydrogenated under an atmosphere of anhydrous hydrogen while being shaken vigorously. After hydrogen absorption has been completed, it is concentrated by evaporation and chromatographed on about 250 ml of fine silica gel with a mixture of n-hexane and ethyl acetate. 226 mg (795 μmol, 45%) of title compound A and 31 mg (109 μmol, 6%) of title compound B are isolated in each case as a colorless solid as well as 205 mg (721 μmol, 41%) of a mixed fraction of A and B.

EXAMPLE 34

[1R-[1α,2β(2R*, 3S*),4α,4aβ,10aβ]]-3-(Ethoxycarbonyl)amino-2-hydroxy-3-(3-furanyl)-propanoic acid-9-methylene-1,2,3,4,4a,9,10,10a-octahydro-1,12,12-trimethyl-4a,10a-epoxy-1,4-methanophenanthren-2-ylester 37 mg (56 μmol) of the compound that is presented according to Example 34a is reacted analogously to Example 1. After working-up and purification, 19 mg (37 μmol, 67%) of the title compound is isolated as a colorless oil.

$^1$H-NMR (CDCl$_3$): δ=0.83 (3H), 0.92 (3H), 1.08 (3H), 1.24 (3H), 1.51 (1H), 2.28 (1H), 2.68 (1H), 2.77 (1H), 3.14 (1H), 3.28 (1H), 4.16 (2H), 4.45 (1H), 4.88 (1H), 5.03 (1H), 5.21 (1H), 5.52 (1H), 6.29 (1H), 6.52 (1H), 7.22–7.37 (3H), 7.47 (2H), 7.54 (1H) ppm.

EXAMPLE 34a

[1R-[1α,2β(2R*, 3S*),4α,4aβ,10aβ]]-3-(Ethoxycarbonyl)amino-2-triisopropylsilyloxy-3-(3-furanyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 17 mg (60 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(ethoxycarbonyl)-3-triisopropylsilyloxy-4-(3-furanyl)-2-azetidinone, which has been produced analogously to the process that is described in Tetrahedron 1992 on page 6985 ff. After working-up and purification, 37 mg (56 μmol, 93%) of the title compound is isolated as a colorless oil.

EXAMPLE 35

[1R-[1α,2β(2R*, 3S*),4α,4aβ,10aβ]]-3-(Ethoxycarbonyl)amino-2hydroxy-3-(3-furanyl)-propanoic acid-9-methyl-1,2,3,4,4a,9,10,10a-octahydro-1,12,12-trimethyl-4a,10a-epoxy-1,4-methanophenanthren-2-ylester 15 mg (30 μmol) of the compound that is presented according to Example 34 is hydrogenated analogously to Example 9a. After working-up and purification, 9 mg (18 μmol, 58%) of the title compound is isolated as a colorless oil.

$^1$H-NMR (CDCl$_3$): δ=0.77 (3H), 0.89 (3H), 1.03 (3H), 1.23 (3H), 1.39 (3H), 1.50 (1H), 2.08 (1H), 2.27 (2H), 2.64 (1H), 3.08 (1H), 3.30 (1H), 4.17 (2H), 4.46 (1H), 4.85 (1H), 5.21 (1H), 6.17 (1H), 6.57 (1H), 7.11–7.35 (4H), 7.48 (1H), 7.52 (1H) ppm.

EXAMPLE 36

[1R-[1α,2β(2R*, 3S*),4α,4aβ,10aβ]]-3-[(1-Oxobutyl)amino]-2-hydroxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 34 mg (50 μmol) of the compound that is presented according to Example 36a is reacted analogously to Example 1. After working-up and purification, 20 mg (38 μmol, 77%) of the title compound is isolated as a colorless oil.

$^1$H-NMR (CDCl$_3$); δ=0.79 (3H), 0.84 (3H), 0.91 (3H), 1.07 (3H), 1.44 (1H), 1.59 (2H), 2.19 (2H), 2.25 (1H), 2.71 (1H), 2.84 (1H), 3.08 (1H), 32.6 (1H), 4.43 (1H), 4.98 (1H), 5.02 (1H), 5.53 (1H), 5.67 (1H), 7.15 (1H), 7.23 (2H), 7.36 (2H), 7.47–7.64 (3H) ppm.

EXAMPLE 36a

[1R-[1α,2β(2R*, 3S*),4α,4aβ,10aβ]]-3-[(1-Oxobutyl)amino]-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 17 mg (60 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(1-oxobutyl)-3-triisopropylsilyloxy-4-(3-thienyl)-2-azetidinone, which has been produced analogously to the process that is described in Tetrahedron 1992 on page 6985 ff. After working-up and purification, 34 mg (50 μmol, 84%) of the title compound is isolated as a colorless oil.

EXAMPLE 37

[1R-[1α,2β(2R*,3S*),4α,4aβ,10aβ]]-3-[(3-Phenyl-1-oxopropyl)amino]-2-hydroxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 32 mg (43 μmol) of the compound that is presented according to Example 37a is reacted analogously to Example 1. After working-up and purification, 22 g (38 μmol, 88%) of the title compound is isolated as a colorless oil.

$^1$H-NMR (CDCl$_3$): δ=0.84 (3H), 0.89 (3H), 1.04 (3H), 1.24 (1H), 2.15 (1H), 2.60 (1H), 2.68 (1), 2.78 (1H), 2.83 (2H), 3.02 (1H), 3.22 (1H), 4.37 (1), 4.83 (1H), 4.94 (1H), 5.30 (1H), 5.59 (6.59 (1H), 6.84 (2H), 6.93 (1H), 6.98 (2H), 7.11 (2H), 7.38 (7.47–7.62 (3H) ppm.

EXAMPLE 37a

[1R-[1α,2β(2R*,3S*),4α,4aβ,10aβ]]-3-[(3-Phenyl-1-oxopropyl)amino]-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 17 mg (60 μmol) of [1R-(1α,2β,4α,4aβ,10aβ)]-9-methylene-1,2,3,4,4a,9,10,10a-octahydro-1,12,12-trimethyl-4a,10a-epoxy-1,4-methano-phenanthren-2-ol is reacted using (3R,4S))-1-(3-phenyl-1-oxopropyl)-3-triisopropylsilyloxy-4-(3-thienyl)-2-azetidinone, which has been produced analogously to the process that is described in Tetrehedron 1992 on page 6985 ff. After working-up and purification, 32 mg (43 μmol, 72%) of the title compound is isolated as a colorless oil.

EXAMPLE 38

[1R-[1α,2β(2R*,3S*),4α,4aβ,10aβ]]-3-[(3-Phenyl-1-oxopropyl)amino]-2-hydroxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 17 mg (29 μmol) of the compound that is presented according to Example 37 is hydrogenated analogously to Example 9a. After working-up and purification, 1.6 mg (3 μmol, 9%) of the title compound is isolated as a colorless oil.

$^1$H-NMR (CDCl$_3$): δ=0.78 (3H), 0.89 (3H), 0.98 (3H), 1.29 (3H), 1.53 (1H), 2.07 (2H), 2.21 (1H), 2.44–2.72 (3H), 2.91 (2H), 3.08 (1H), 3.36 (1H), 4.43 (1H), 5.06 (1H), 5.52 (1H), 6.89 (1H), 6.93–7.06 (3H), 7.10–7.37 (8H), 7.53 (1H) ppm.

EXAMPLE 39

[1R-[1α,2β(2R*,3S*),4α,4aβ,9β,10aβ] -3-[(1-Oxobutyl)amino]-2-hydroxy-3-(3-thienyl)-propanoic acid-9-methyl-1,2,3,4,4a,9,10,10a-octahydro-1,12,12-trimethyl-4a,10a-epoxy-1,4-methanophenanthren-2-ylester 17 mg (33 μmol) of the compound that is presented according to Example 36 is hydrogenated analogously to Example 9a. After working-up and purification, 1.4 mg (2.7 μmol, 8%) of the title compound is isolated as a colorless oil.

$^1$H-NMR (CDCl$_3$): δ=0.78 (3H), 0.90 (3H), 1.00 (3H), 1.25 (3H), 1.36 (1H), 1.51–1.72 (3H), 2.11 (2H), 2.23 (2H), 2.28 (1H), 2.66 (1H), 3.09 (1H), 3.51 (1H), 4.51 (1H), 5.02 (1H), 5.60 (1H), 6.99 (1H), 7.10–7.34 (6H), 7.49 (1H) ppm.

EXAMPLE 40

[1R-[1α,2β[2R*,3S*(2R*,3S*)],4α,4aβ,10aβ]]-3-[[3-(Ethoxycarbonyl)amino]-2-hydroxy-3-(3thienyl)-1-oxopropyl]amino-2-hydroxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 19 mg (19 μmol) or 14 mg (16 μmol) of the compounds that are presented according to Example 40a is reacted analogously to Example 1. After working-up and purification, 12.2 mg (17.6 μmol, 50%) of the title compound is isolated as a colorless oil.

$^1$H-NMR (CDCl$_3$): δ=0.83 (3H), 0.92 (3H), 1.05 (3H), 1.19 (3H), 1.61 (1H), 2.23 (1H), 2.71 (1H), 2.78 (1H), 3.12 (1H), 3.29 (1H), 3.50 (1H), 4.03 (2H), 4.32 (2H), 5.02 (1H), 5.14 (2H), 5.33 (1H), 5.61 (1H), 5.70 (1H), 6.71 (1H), 6.74 (1H), 6.98 (1H), 7.06 (2H), 7.22 (1H), 7.38 (2H), 7.52 (2h), 7.93 (1H) ppm.

EXAMPLE 40a

[1R-[1α,2β[2R*,3S*(2R*,3S*)],4α,4aβ,10aβ]]-3-[[3-(Ethoxycarbonyl)amino]-2-triisopropylsilyloxy-3-(3-thienyl)-1-oxopropyl]amino]-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester The solution of 25 mg (41 μmol) of the compound, presented according to Example 40b, in 0.5 ml of anhydrous dichloromethane is mixed under an atmosphere of dry argon with 51 mg of the acid that is presented according to Example 40d, 17 mg of 1-hydroxy-1H-benzotriazole, 56 μl of N-ethyldiisopropylamine, 39 mg of O-(benzotriazol-1-yl)-N,N,N',N'-tetramethyluronium tetrafluoroborate, and it is stirred for 1 hour at 23° C. It is poured into a saturated sodium bicarbonate solution, extracted with dichloromethane, and the combined organic after filtration and removal of the solvent is purified by chromatography on two analytical silica gel plates. A mixture of n-hexane and ethyl acetate is used as a mobile solvent; a mixture of dichloromethane and methanol is used as an eluant. 19 mg (19 μmol, 46%) of the title compound as well as 14 mg (16 μmol, 39%) of a monodesilylated compound are isolated, in each case as a colorless foam.

EXAMPLE 40b

[1R-[1α,2β(2R*,3S*),4α,4aβ,10aβ] -3-Amino-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester The solution of 55 mg (79 μmol) of the compound, presented according to Example 40c, in 0.8 ml of anhydrous tetrahydrofuran is mixed under an atmosphere of dry argon with 16 μl of n-butylamine, 9.2 mg of tetrakis-triphenylphosphine-palladium (O), 4.2 mg of triphenylphosphine, and it is stirred for 2 hours at 23° C. It is poured into a saturated sodium bicarbonate solution, extracted with ethyl acetate, and the combined organic extracts are dried on sodium sulfate. The residue that is obtained after filtration and removal of the solvent is purified by chromatography on three analytical silica gel plates. A mixture of n-hexane and ethyl acetate is used as a mobile solvent; a mixture of dichloromethane and methanol is used as an eluant. 30 mg (49 μmol, 62%) of the title compound is isolated as a colorless foam.

EXAMPLE 40c

[1R-[1α,2β(2R*,3S*),4α,4aβ,10aβ] -3-(Allyloxycarbonyl)amino-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 30 mg (106 μmol) of [1R-(1α,2β,4α,4aβ,10aβ)]-methylene-1,2,3,4,4a,9,10,10a- octahydro-1,12,12-trimethyl-4a,10a-epoxy-1,4-methanophenanthren-2-ol is reacted using (3R,4S)-1-allyloxycarbonyl-3-triisopropylsilyloxy-4-(3-thienyl)-2-azetidinone, which has been produced analogously to the process that is described in Tetrahedron 1992 on page 6985 ff. After working-up and purification, 61 mg (88 µmol, 83%) of the title compound is isolated as a colorless oil.

EXAMPLE 40d (2R,3R)-2-Triisopropylsilyloxy-3-(ethoxycarbonyl) amino-3-(3-thienyl)-propanoic acid The solution of 160 mg (372 µmol) of the compound, presented according to Example 40e, in 6 ml of methanol, is mixed with 2 ml of a 5% aqueous lithium hydroxide solution, and it is stirred for 20 hours at 23° C. It is diluted with water, set at pH 6–7 by adding a 4N hydrochloric acid and extracted with dichloromethane. The combined organic extracts are dried on sodium sulfate, and the residue that is obtained after filtration and removal of the solvent is purified by chromatography on fine silica gel with a gradient system of n-hexane, ethyl acetate and methanol. 66 mg (159 µmol), 43%) of the title compound is isolated as a colorless foam.

EXAMPLE 40e (2R,3R)-2-Triisopropylsilyloxy-3-(ethoxycarbonyl) amino-3-(3-thienyl)-propanoic acid methyl ester The solution of 160 mg (402 µmol) of (3R,4S)-1-ethoxycarbonyl-3-triisopropylsilyloxy-4-(3-thienyl)-2-azetidinone, which has bee produced analogously to the process that is described in Tetrahedron 1992 on page 6985 ff, in 4 ml of methanol is mixed with 26 mg of sodium methanolate, and it is stirred for 3 hours under an atmosphere of dry argon at 23° C. It is poured into a saturated ammonium chloride solution, extracted with dichloromethane, and the combined organic extracts are dried on sodium sulfate. After filtration and removal of the solvent, 170 mg (396 µmol, 98%) of the title compound is isolated as a colorless foam, which is further reacted without purification.

EXAMPLE 41

[1R-[1α,2β[2R*,3S*(2R*,3S*)],4α,4aβ,10aβ]]-3-[[3-(Ethoxycarbonyl)amino]-2-hydroxy-3-phenyl-1-oxopropyl]amino]-2-hydroxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 6.0 (6.0 µmol) of the compound that is presented according to Example 41a is reacted analogously to Example 1. After working up and purification, 4.0 mg (5.8 µmol, 97%) of the title compound is isolated as a colorless oil.

$^1$H-NMR (CDCl$_3$): δ=0.83 (3H), 0.91 (3H), 1.03 (3H), 1.21 (3H), 1.51 (1H), 2.20 (1H), 2.72 (1H), 2.79 (1H), 3.15 (1H), 3.19 (1H), 4.05 (2H), 4.31 (2H), 5.02 (1H), 5.08 (1H), 5.10 (1H), 5.43 (1H), 5.58 (1H), 5.72 (1H), 6.74 (1H), 6.87–7.03 (5H), 7.12 (1H), 7.18 (1H), 7.40 (2H), 7.58 (2H), 7.82 (1H) ppm.

EXAMPLE 41a

[1R-[1α,2β[2R*,3S*(2R*,3S*)],4α,4aβ,10aβ]]-3-[[3-(Ethoxycarbonyl)amino]-2-triisopropylsilyloxy-3-phenyl-1-oxopropyl]amino]-2triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester By analogy with Example 40a, 10.0 mg (16.4 µmol) of the compound that is presented according to Example 40b is reacted using the acid that is presented according to Example 41b. After working-up and purification, 4.0 mg (4.0 µmol, 24%) of the title compound is isolated as a colorless oil.

EXAMPLE 41b (2R,3S)-2-Triisopropylsilyloxy-3-(ethoxycarbonyl) amino-3-phenyl-propanoic acid 560 mg (1.3 mmol of the compound that is presented according to Example 41d is reacted analogously to Example 40d. After working-up and purification, 470 mg (1.15 mmol, 88%) of the title compound is isolated as a colorless oil.

EXAMPLE 41c (2R,3S)-2-Triisopropylsilyloxy-3-(ethoxycarbonyl) amino-3-phenyl-propanoic acid methyl ester By analogy with Example 40e, 1.1 g (2.8 mmol) of (3R,4S)-1-ethoxycarbonyl-3-triisopropylsilyloxy-4-phenyl-2-azetidinone, which has been produced analogously to the process that is described in Tetrahedron 1992 on page 6985 ff, is reacted. After working-up and purification, 1.16 g (2.74 mmol, 98%) of the title compound is isolated as a colorless oil.

EXAMPLE 42

[1R-[1α,2β[2R*,3S*(2R*,3S*)],4α,4aβ,10aβ]]-3-[[3-(Ethoxycarbonyl)amino]-2-hydroxy-3-(4-pyridyl)-1-oxopropyl]amino-2-hydroxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 3.4 mg (3.4 µmol) of the compound that is presented according to Example 42a is reacted analogously to Example 1. After working-up and purification, 0.8 mg (1.2 µmol, 35%) of the title compound is isolated as a colorless oil.

$^1$H-NMR (CDCl$_3$): δ=0.79 (3H), 0.93 (3H), 1.00 (3H), 1.17 (3H), 1.31 (3H), 2.00–2.15 (3H), 2.40 (1H), 2.77 (1H), 3.11 (1H), 3.55 (broad, 2H), 3.94–4.18 (2H), 4.49 (1H), 4.58 (1H), 5.20 (1H), 5.28 (1H), 5.51 (1H), 5.60 (1H), 6.98 (2H), 7.15–7.40 (5H), 7.46 (1H), 8.00–8.13 (3H), 8.53 (2H) ppm.

EXAMPLE 42a

[1R-[1α,2β[2R*,3S*(2R*,3S*)],4α,4aβ,9β,10aβ]]-3-[[3-(Ethoxycarbonyl)amino]-2-triisopropylsilyloxy-3-(4-pyridyl)-1-oxopropyl] amino]-2-triisopropylsilyoxy-3-(4-pyridyl)-propanoic acid-9-methyl-1,2,3,4,4a,9,10,10a-octahydro-1,12,12trimethyl-4a,10a-epoxy-1,4-methanophenanthren-2-ylester By analogy with Example 40a, 8.0 mg (13.2 µmol) of the compound that is presented according to Example 42b is reacted using the acid that is presented according to Example 42D. After working-up and purification, 3.4 mg (3.4 µmol, 26%) of the title compound is isolated as a colorless oil.

EXAMPLE 42b

[1R-[1α,2β[2R*,3S*(2R*,3S*)],4α,4aβ,9β,10aβ]]-2-Triisopropylsilyloxy-3-amino-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 31 mg (45 µmol) of the compound that is presented according to Example 42c is reacted analogously to

EXAMPLE 42c

[1R-[1α,2β(2R*,3S*),4α,4aβ,9β,10aβ]]-3-
(Allyloxycarbonyl)amino-2-triisopropylsilyloxy-3-
(4-pyridyl)-propanoic acid-9-methyl-1,2,3,4,4a,9,10,
10a-octahydro-1,12,12-trimethyl-4a,10a-epoxy-1,4-
methanophenanthren-2-ylester By analogy with Example 1a, 20 mg (70 μmol) of the compound that is presented according to Example 33a is reacted using (3R,4S)-1-allyloxycarbonyl-3-triisopropylsilyl-oxy-4-(4-pyridyl)-2-azetidinone, which has been produced analogously to the process that is described in Tetrahedron 1992 on page 6985 ff. After working-up and purification, 31 mg (45 μmol, 65%) of the title compound is isolated as a colorless oil.

EXAMPLE 42d (2R,3S)-2-Triisopropylsilyloxy-3-(ethoxycarbonyl)
amino-3-(4-pyridyl)-propanoic acid 220 mg (520 μmol) of the compound that is presented according to Example 42e is reacted analogously to Example 40d. After working-up and purification, 52 mg (127 μmol, 25%) of the title compound is isolated as a colorless oil.

EXAMPLE 42e (2R,3S)-2-Triisopropylsilyloxy-3-(ethoxycarbonyl)
amino-3-(4-pyridyl)-propanoic acid methyl ester 340 mg (0.87 mmol) of (3R,4S)-1-ethoxycarbonyl-3-triisopropylsilyloxy-4-(4-pyridyl)-2-azetidinone, which has been produced analogously to the process that is described in Tetrahedron 1992 on page 6985 ff, is reacted analogously to Example 40e. After working-up and purification, 350 mg (0.82 mmol, 95%) of the title compound is isolated as a colorless oil.

EXAMPLE 43

[1R-[1α,2β(2R*,3S*),4α,4aβ,9α,10aβ]]-3-
(Ethoxycarbonyl)amino-2-hydroxy-3-(4-pyridyl)-
propanoic acid 9-methyl-1,2,3,4,4a,9,10,10a-
octahydro-1,12,12-trimethyl-4a,10a-epoxy,1,4-
methanophenanthren-2-ylester 21 mg (31 μmol) of the compound that is presented according to Example 43a is reacted analogously to Example 1. After working-up and purification, 9.6 mg (18 μmol, 60%) of the title compound is isolated as a colorless oil.

$^1$H-NMR (CDCl$_3$): δ=0.76 (3H), 0.89 (3H), 1.06 (3H), 1.22 (3H), 1.43 (3H), 1.48–1.66 (2H), 2.27 (1H), 2.46 (1H), 2.75 (1H), 3.14 (1H), 4.12 (2H), 4.56 (1H), 4.85 (1H), 5.31 (1H), 6.91 (1H), 7.22–7.61 (6H), 8.51 (2H) ppm.

EXAMPLE 43a

[1R-[1α,2β(2R*,3S*),4α,4aβ,9α,10aβ]]-3-
(Ethoxycarbonyl)amino-2-triisopropylsilyloxy-b 3-
(4-pyridyl)-propanoic acid 9-methyl-1,2,3,4,4a,9,10,
10a-octahydro-1,12,12-trimethyl-4a,10a-epoxy,1,4-
methanophenanthren-2-ylester By analogy with Example 1a, 20 mg (70 μmol) of compound B, presented according to Example 33b, is reacted using (3R,4S)-1-(ethoxycarbonyl)-3-triisopropylsilyloxy-4-(4-pyridyl)-2-azetidinone, which has been produced analogously to the process that is described in Tetrahedron 1992 on page 6985 ff. After working-up and purification, 34 mg (50 μmol, 72% of the title compound is isolated as a colorless oil.

EXAMPLE 44

[1R-[1α,2β(2R*,3S*),4α,4aβ,9α,10aβ]]-3-
(Ethoxycarbonyl)amino-2-hydroxy-3-(3-thienyl)-
propanoic acid 9-methyl-1,2,3,4,4a,9,10,10a-
octahydro-1,12,12-trimethyl-4a,10a-epoxy,1,4-
methanophenanthren-2-ylester 8.2 mg (12 μmol) of the compound that is presented according to Example 44a is reacted analogously to Example 1. After working-up and purification, 2.8 mg (5.3 μmol, 44%) of the title compound is isolated as a colorless oil.

$^1$H-NMR (CDCl$_3$): δ=0.75 (3H), 0.87 (3H), 1.05 (1H), 1.23 (3H), 1.42 (3H), 1.45 (1H), 1.55 (1H), 2.24 (1H), 2.46 (1H), 2.71 (1H), 3.07–3.24 (2H), 4.13 (2H), 4.48 (1H), 4.82 (1H), 5.37 (1H), 6.89 (1H), 7.15–7.42 (6H), 7.50 (1H) ppm.

EXAMPLE 44a

[1R-[1α,2β(2R*,3S*),4α,4aβ,9α,10aβ]]-3-
(Ethoxycarbonyl)amino-2triisopropylsilyloxy-3-(3-
thienyl)-propanoic acid 9-methyl-1,2,3,4,4a,9,10,
10a-octahydro-1,12,12-trimethyl-4a,10a-epoxy,1,4-
methanophenanthren-2-ylester By analogy with Example 1a, 6.4 mg (22 μmol) of compound A, presented according to Example 43b, is reacted using (3R,4S)-1-(ethoxycarbonyl)-3-triisopropylsilyloxy-4-(3-thienyl)-2-azetidinone, which has been produced analogously to the process that is described in Tetrahedron 1992 on page 6985 ff. After working-up and purification, 8.2 mg (12 μmol, 54%) of the title compound is isolated as a colorless oil.

EXAMPLE 45

[1R-[1α,2β(2R*,3S*),4α,4aβ,9β,10aβ]]-3-
(Ethoxycarbonyl)amino-2-hydroxy-3-(1-methyl-4-
pyridino)-propanoic acid 9-methyl-1,2,3,4,4a,9,10,
10a-octahydro-1,12,12-trimethyl-4a,10a-epoxy,1,4-
methanophenanthren-2-ylester iodide The solution of 3.7 mg (7.1 μmol) of the compound, presented according to Example 33, in 0.1 ml of dichloromethane is mixed under an atmosphere of dry argon with 4.4 μl of iodomethane, and it is stirred for 5 hours at 23° C. After the solvent is removed, 4.1 mg (6.2 μmol, 87%) of the title compound is obtained as a colorless foam.

$^1$H-NMR (CDCl$_3$): δ=0.77 (3H), 0.90 (0.90 (3H), 1.05 (3H), 1.12 (3H), 1.36 (3H), 1.56 (1H), 2.09 (1H), 2.22 (1H), 2.39 (1H), 2.72 (1H), 3.08 (1H), 4.02 (2H), 4.53 (4H), 4.79 (1H), 4.93 (1H), 5.48 (1H), 6.61 (1H), 7.10–7.35 (3H), 7.52 (1H), 8.11 (2H), 8.99 (2H) ppm.

EXAMPLE 46

[1R-[1α,2β(2R*,3S*),4α,4aβ,9β,10aβ]]-3-
(Ethoxycarbonyl)amino-2(1-oxo-2-(dimethylamino)
ethoxy)-3-(4-pyridyl)-propanoic acid-9-methyl-1,2,
3,4,4a,9,10,10a-octahydro-1,12,12-trimethyl-4a,10a-
epoxy-1,4-methanophenanthren-2-ylester The solution of 7.9 mg (15 μmol) of the compound, presented according to Example 33, in 0.8 ml of dichloromethane is mixed under an atmosphere of dry argon with 4.7 mg of N,N-dimethylglycine, 6.3 mg of 1,3-dicylclohexylcarbodiimide, 1.5 mg of 4-dimethylaminopyridine, and it is stirred for 16 hours at 23° C. It is poured into a saturated sodium chloride solution, extracted several times with dichloromethane, the combined organic extracts are washed with saturated sodium chloride solution and dried on sodium sulfate. The residue that is obtained after filtration and removal of the solvent is purified by chromatography on about 10 ml of fine silica gel. A mixture of n-hexane, ethyl acetate and triethylamine is used as a mobile solvent. 2.9 mg (4.8 μmol, 32%) of the title compound is isolated as a colorless oil.

$^1$H-NMR (CDCl$_3$): δ=0.75 (3H), 0.86 (3H), 1.23 (3H), 1.33 (1H), 1.40 (3H), 2.07 (1H), 2.15 (2H), 2.36 (6H), 2.59 (1H), 2.98–3.47 (3H), 4.13 (2H), 4.95 (1H), 5.43 (1H), 5.48 (1H), 6.50 (1H), 7.12–7.50 (6H), 8.54 (2H) ppm.

EXAMPLE 47

[1R-[1α,2β(2R*,3S*),4α,4aβ,9β,10aβ]]-3-(Ethoxycarbonyl)amino-2-(1-oxo-2-(dimethylamino) ethoxy)-3-(4-pyridyl)-propanoic acid-9-methyl-1,2,3,4,4a,9,10,10a-octahydro-1,12,12-trimethyl-4a,10a-epoxy-1,4-methanophenanthren-2-ylester bis-hydrogen-methanesulfonate The solution of 3.2 mg (5.3 μmol) of the compound, presented according to Example 46, in 50 μl of dichloromethane is mixed under an atmosphere of dry argon with 0.69 μl of methanesulfonic acid, and it is stirred at 23° C. After the solvent is removed, 3.9 mg (4.9 μmol, 92%) of the title compound is obtained as a colorless foam.

EXAMPLE 48

[1R-[1α,2β(2R*,3S*),4α,4aβ,9β,10aβ]]-3-(Ethoxycarbonyl)amino-2-(1-oxo-2-(dimethylamino) ethoxy)-3-(2-thienyl)-propanoic acid-9-methyl-1,2,3,4,4a,9,10,10a-octahydro-1,12,12-trimethyl-4a,10a-epoxy-1,4-methanophenanthren-2-ylester 15 mg (29 μmol) of the compound that is presented according to Example 29 is reacted analogously to Example 46. After working-up and purification, 11.6 mg (19 μmol, 65%) of the title compound is isolated as a colorless oil.

$^1$H-NMR (CDCl$_3$): δ=0.73 (3H), 0.86 (3H), 0.99 (3H), 1.23 (4H), 1.39 (3H), 1.42 (1H), 2.04 (1H), 2.18 (1H), 2.39 (6H), 2.58 (1H), 3.05 (1H), 3.41 (2H), 4.13 (2H), 4.98 (1H), 5.48 (1H), 5.62 (1H), 6.49 (1H), 6.92 (1H), 7.09–7.31 (5H), 7.43 (1H) ppm.

EXAMPLE 49

[1R-[1α,2β(2R*,3S*),4α,4aβ,9β,10aβ]]-3-(Ethoxycarbonyl)amino-2-(1-oxo-2-(dimethylamino) ethoxy)-3-(2-thienyl)-propanoic acid-9-methyl-1,2,3,4,4a,9,10,10a-octahydro-1,12,12-trimethyl-4a,10a-epoxy-1,4-methanophenanthren-2-ylester hydrogen methanesulfonate 9.9 mg (16 μmol) of the compound that is presented according to Example 48 is reacted analogously to Example 47. After working-up and purification, 11.4 mg (16 μmol, 99%) of the title compound is isolated as a colorless foam.

EXAMPLE 50

[1R-[1α,2β(2R*,3S*),4α,4aβ,9β,10aβ]]-3-(Ethoxycarbonyl)amino-2-hydroxy-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester-β-cyclodextrin-adduct The solution of 5.4 mg (10 μmol) of the compound, presented according to Example 9, in 57 μl of ethanol is mixed with the solution of 114 mg of β-cyclodextrin in 0.8 ml of water and heated for 2 hours to 50–70° C. It is allowed to cool to 23° C. and stirred for another 5 days. The precipitate is suctioned off, washed with 0.1 ml of a water/ethanol mixture and dried at 50° C. 78 mg of adduct with an active ingredient content of about 4–6% is isolated.

EXAMPLE 51

[1R-[1α,2β(2R*,3S*),4α,4aβ,10aβ]]-3-(Ethoxycarbonyl)amino-2-hydroxy-3-(1-oxido-4-pyridyl)-propanoic acid-9-methylene-1,2,3,4,4a,9,10,10a-octahydro-1,12,12-trimethyl-4a,10a-epoxy-1,4-methanophenanthren-2-ylester The solution of 3 mg (5.8 μmol) of the compound, presented according to Example 32, in a 1:1 mixture of tetrahydrofuran and toluene is mixed at 0° C. after 30 minutes in each case with 3×1 mg of a 50% meta-chlorperbenzoic acid, and it then is stirred for 1 more hour at 0° C. It is poured into a saturated sodium bicarbonate solution, extracted several times with dichloromethane, the combined organic extracts are washed with saturated sodium chloride solution and dried on sodium sulfate. The residue that is obtained after filtration and removal of the solvent is purified by chromatography on an analytical thin-layer plate. A mixture of ethyl acetate and ethanol is used as a mobile solvent; a mixture of dichloromethane and methanol is used as an eluant. 1.4 mg (2.6 μmol, 44% of the title compound is isolated as a colorless oil.

$^1$H-NMR (CDCl$_3$): δ=0.85 (3HH), 0.92 (3H), 1.09 (3H), 1.23 (3H), 1.39 (1H), 2.29 (1H), 2.71 (1H), 2.81 (1H), 3.14 (1H), 4.13 (2H), 4.53 (1H), 4.90 (1H), 5.05 (1H), 5.30 (1H), 5.54 (1H), 6.44 (1H), 7.20–7.62 (6H), 8.15 (2H) ppm.

EXAMPLE 52

[1R-[1α,2β(2R*,3S*(2S)*),4α,4aβ,9β,10aβ]]-3-(Ethoxycarbonyl)amino-2-hydroxy-3-[4-[2-[[(1,1-dimethylethoxy)carbonyl]amino]-3-benzyloxy-1-oxopropoxy]phenyl]-propanoic acid-9-methyl-1,2,3,4,4a,9,10,10a-octahydro-1,12,12-trimethyl-4a,10a-epoxy-1,4-methanophenanthren-2-ylester 18 mg (19 μmol) of the compound that is presented according to Example 52a is reacted analogously to Example 1. After working-up and purification, 5 mg (6 μmol, 32%) of the title compound is isolated as a colorless oil.

$^1$H-NMR (CDCl$_3$): δ=0.78 (3H), 0.89 (3H), 1.00 (3H), 1.20 (3H), 1.40 (3H), 1.44 (9H), 1.68 (1H), 2.07 (1H), 2.20 (1H), 2.29 (1H), 2.67 (1H), 3.08 (1H), 3.21 (1H), 3.79 (1H), 3.95–4.18 (3H), 4.44–4.73 (4H), 4.92 (1H), 5.29 (1H), 5.49 (1H), 6.27 (1H), 6.98 (2H), 7.13–7.38 (8H), 7.43–7.57 (3H), ppm.

EXAMPLE 52a

[1R-[1α,2β(2R*,3S*(2S)*),4α,4aβ,9β,10aβ]]-3-(Ethoxycarbonyl)amino-2-2-triisopropylsilyloxy-3-[4-[2-[[(1,1-dimethylethoxy)carbonyl]amino]-3-benzyloxy-1-oxopropoxy]phenyl]propanoic acid-9-methyl-1,2,3,4,4a,9,10a-octahydro-1,12,12-trimethyl-4a,10a-epoxy-1,4-methanophenanthren-2-ylester By analogy with Example 46, 15 mg (22 μmol) of the compound that is presented according to Example 20b is reacted using N-Boc-O-benzyl-L-serine. After working-up and purification, 18 mg (19 μmol, 86%) of the title compound is isolated as a colorless oil.

EXAMPLE 53

[1R-[1α,2β(2R*,3S*(2S)*),4α,4aβ,9β,10aβ]]-3-(Ethoxycarbonyl)amino-2-hydroxy-3-[4-[2-[[(1,1-dimethylethoxy)carbonyl]amino]-3-hydroxy-1-oxopropoxy]phenyl]-propanoic acid-9-methyl-1,2,3,4,4a,9,10,10a-octahydro-1,12,12-trimethyl-4a,10a-epoxy-1,4-methanophenanthren-2-ylester 5.1 mg (6.3 μmol) of the compound that is presented according to Example 52 is hydrogenated analogously to Example 9a. After working-up and purification, 0.8 mg (1.1 μmol, 18%) of the title compound is isolated as a colorless oil.

$^1$H-NMR (CDCl$_3$): δ=0.79 (3H), 0.89 (3H), 1.02 (3H), 1.20 (3H), 1.40 (3H), 1.48 (9H), 1.68 (1H), 2.08 (1H), 2.21 (1H), 2.29 (1H), 2.68 (1H), 3.07 (1H), 3.20 (1H), 3.98–4.21 (4H), 4.52 (1H), 4.60 (1H), 4.91 (1H), 5.28 (1H), 5.48 (1H), 6.28 (1H), 7.05 (2H), 7.14–7.36 (4H), 7.45–7.60 (3H) ppm.

EXAMPLE 54

[1R-[1α,2β(2R*,3S(E,E,2RS)*), 4α,4aβ,9β,10aβ]]-3-(Ethoxycarbonyl)amino-2-hydroxy-3-[4-[[2-[[methoxy(3,7,11-trimethyl-2,6,10-dodecatrienyl)phosphinyl]oxy]acetyl]oxy]phenyl]propanoic acid-9-methyl-1,2,3,4,4a,9,10,10a-octahydro-1,12,12-trimethyl-4a,10a-epoxy-1,4-methanophenanthren-2-ylester 6.0 mg (5.8 μmol) of the compound that is presented according to Example 54a is reacted analogously to Example 1. After working-up and purification, 1.4 mg (1.6 μmol, 28%) of the title compound is isolated as a colorless oil.

$^1$H-NMR (CDCl$_3$): δ=0.79 (3H), 0.89 (3H), 1.01 (3H), 1.19 (3H), 1,39 (3H), 1.46–1.73 (13H), 1.90–2.20 (9H), 2.28 (1H), 2.66 (2H), 2.74 (1H), 3.07 (1H), 3.21 (1H), 3.78 (3H), 4.09 (2H), 4.52 (1H), 4.80 (2H), 4.91 (1H), 5.09 (2H), 5.15–5.32 (2H), 6.26 (1H), 7.07 (2H), 7.14–7.32 (4H), 7.44–7.60 (3H) ppm.

EXAMPLE 54a

[1R-[1α,2β(2R*,3S(E,E,2RS)*),4α,4aβ,9β,10aβ]]-3-(Ethoxycarbonyl)amino-2-triisopropylsilyloxy-3-[4-[[2-[[methoxy(3,7,11-trimethyl-2,6,10-dodecatrienyl)phosphinyl]oxy]acetyl]oxy]phenyl]-propanoic acid-9-methyl-1,2,3,4,4a,9,10,10a-octahydro-1,12,12-trimethyl-4a,10a-epoxy-1,4-methanophenanthren-2-ylester By analogy with Example 46, 10 mg (15 μmol) of the compound, presented analogously to Example 20b, is reacted using 2-[[methoxy(3,7,11-trimethyl-2,6,10-dodecatrienyl)phosphinyl]oxy]acetic acid, which has been produced according to the process that is described in J. Med. Chem. 1995, 38, 439. After working-up and purification, 6 mg (5.8 μmol, 40%) of the title compound is isolated as a colorless oil.

EXAMPLE 55

[1R-[1α,2β(2R*,3S(4R)*), 4α,4aβ,9β,10aβ]]-3-(Ethoxycarbonyl)amino-2-hydroxy-3-[4-[4-[[4-(1-methylethylene)cyclohex-1-ene]carbonyloxy]-1-oxobutoxy]phenyl]-propanoic acid-9-methyl-1,2,3,4,4a,9,10,10a-octahydro-1,12,12-trimethyl-4a,10a-epoxy-1,4-methanophenanthren-2-ylester 10 mg (11 μmol) of the compound that is presented according to Example 55a is reacted analogously to Example 1. After working-up and purification, 4.2 mg (5.5 μmol, 51%) of the title compound is isolated as a colorless oil.

$^1$H-NMR (CDCl$_3$): δ=0.78 (3H), 0.89 (3H), 1.01 (3H), 1.19 (3H), 1.40 (3H), 1.48 (1H), 1.69 (1H), 1.74 (3H), 1.89 (1H), 2.00–2.39 (8H), 2.48 (1H), 2.58–2.72 (3H), 3.07 (1H), 3.20 (1H), 2.09 (2H), 2.23 (2H), 4.51 (1H), 4.72 (1H), 4.76 (1H), 4.91 (1H), 5.28 (1H), 6.27 (1H), 6.93–7.07 (3H), 7.12–7.32 (3H), 7.41–7.58 (3H) ppm.

EXAMPLE 55a

[1R-[1α,2β(2R*,3S(4R)*), 4α,4aβ,9β,10aβ]]-3-(Ethoxycarbonyl)amino-2-triisopropylsilyloxy-3-[4-[4-[[4-(1-methylethylene)cyclohex-1-ene]carbonyloxy]-1-oxobutoxy]phenyl]-propanoic acid-9-methyl-1,2,3,4,4a,9,10,10a-octahydro-1,12,12-trimethyl-4a,10a-epoxy-1,4-methanophenanthren-2-ylester By analogy with Example 14, 15 mg (22 μmol) of the compound that is presented according to Example 20b is reacted using the acid chloride solution that is presented according to Example 55b. After working-up and purification, 10 mg (11 μmol, 50% of the title compound is isolated as a colorless oil.

EXAMPLE 55b

4-[[4-(1-Methylethylene)cyclohex-1-ene]carbonyloxy]-butanoic acid chloride

The solution of 35 mg (139 μmol) of the acid, presented according to Example 55c, in 1 ml of anhydrous toluene is mixed at 10° C. under an atmosphere of dry argon with 55 μl of thionyl chloride and allowed to stir for 30 minutes before further reaction.

EXAMPLE 55c

4-[[4-(1-Methylethylene)cyclohex-1-ene]carbonyloxy]-butanoic acid

The solution of 35 mg (147 μmol) of the alcohol, presented according to Example 55d, in 2 ml of acetone is cooled to −30° C., mixed with 112 μl of a standardized 8N chromosulfuric acid solution, and it is stirred for 1.5 hours. It is mixed with 5 ml of water, extracted several times with diethyl ether, the combined organic extracts are washed with a saturated sodium chloride solution and dried on magnesium sulfate. The residue that is obtained after filtration and removal of the solvent is further reacted without purification. 35 mg (138 μmol, 94%) of the title compound is isolated as a pale yellow oil.

EXAMPLE 55d

4-[[4-(1-Methylethylene)cyclohex-1-ene]carbonyloxy]-butan-1-ol

The solution of 747 mg (2.3 mmol) of the ether that is presented according to Example 55e in a mixture of 20 ml of tetrahydrofuran and 3 ml of water is mixed with 666 mg of p-toluenesulfonic acid and heated for 16 hours to 50° C. It is poured into a saturated sodium bicarbonate solution, extracted several times with ethyl acetate, the combined organic extracts are washed with a saturated sodium chloride solution and dried on magnesium sulfate. The residue that is obtained after filtration and removal of the solvent is purified by chromatography on about 150 ml of fine silica gel with a mixture of n-hexane and ethyl acetate. 463 mg (1.94 mmol, 84%) of the title compound is isolated as a colorless oil.

EXAMPLE 55e

4-[[4-(1-Methylethylene)cyclohex-1-ene]carbonyloxy]-butane-1-tetrahydropyran-2-yloxy The solution of 670 mg (4.0 mmol) of (S)-perillic acid in 40 ml of anhydrous toluene is mixed under an atmosphere of dry argon at 0° C. with 1.5 ml of thionyl chloride, allowed to heat to 23° C., mixed with the solution of 697 mg of 4 hydroxy-butane-1-tetrahydropyran-2-yloxy in 20 ml of anhydrous dichlormethane, with 1.44 ml of triethylamine, and it is stirred for 1 hour at 23° C. It is poured into a saturated sodium bicarbonate solution, extracted several times with ethyl acetate, the combined organic extracts are washed with a saturated sodium chloride solution and dried on magnesium sulfate. The residue that is obtained after filtration and removal of the solvent is purified by chromatography on about 150 ml of fine silica gel with a mixture of n-hexane an ethyl acetate. 747 mg (2.3 mmol, 58%) of the title compound is isolated as a colorless oil.

EXAMPLE 56

[1R-[1α,2β(2R*,3S(E,E,2R or 2S)*),4α,4aβ,10aβ]]-3-[2-[[Methoxy(3,7,11-trimethyl-2,6,10-dodecatrienyl)phosphinyl]oxy]acetyl]amino-2-hydroxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 2.3 mg (2.4 μmol) of the compound that is presented according to Example 56a is reacted analogously to Example 1. After working-up and purification, 1.3 mg (1.6 μmol, 68%) of the title compound is isolated as a colorless oil.

$^1$H-NMR (CDCl$_3$): δ=0.83 (3H), 0.92 (3H), 1.04 (3H), 1.48–1.74 (13H), 1.91–2.13 (8H), 2.29 (1H), 2.69 (2H), 2.78 (1H), 3.10 (1H), 3.32 (1H), 3.68 (3H), 4.38–4.59 (3H), 4.98–5.21 (5H), 5.53 (1H), 5.64 (1H), 7.13 (1H), 7.21–7.36 (4H), 7.47–7.62 (3H), ppm.

EXAMPLE 56a

[1R-[1α,2β(2R*,3S(E,E,2R or 2S)*),4α,4aβ,10aβ]]-3-[2-[[Methoxy(3,7,11-trimethyl-2,6,10-dodecatrienyl)phosphinyl]oxy]acetyl]amino-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester (A) and [1R-[1α,2β(2R*,3S(E,E,2S or 2R)*),4α,4aβ,10aβ]]-3-[2-[[methoxy(3,7,11-trimethyl-2,6,10dodecatrienyl)phosphinyl]oxy]acetyl]amino-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthrene-2-ylester (B)

By analogy with Example 46, 10 mg (16 μmol) of the compound that is presented according to Example 56b is reacted using 2-[[methoxy(3,7,11-trimethyl-2,6,10-dodecatrienyl)-phosphinyl]oxy]acetic acid, which has been produced according to the process that is described in J. Med. Chem. 1995, 38, 439. After working-up and purification, 2.3 mg (2.4 μmol, 15%) of title compound A as well as 1.9 mg (2.0 μmol, 13%) of title compound B are isolated, in each case as a colorless oil.

EXAMPLE 56b

[1R-[1α,2β(2R*,3S*),4α,4aβ,10aβ]]-3-Amino-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 119 mg (172 μmol) of the compound that is presented according to Example 56c is reacted analogously to Example 40b. After working-up and purification, 49 mg (81 μmol, 47%) of the title compound is isolated as a colorless oil.

EXAMPLE 56c

[1R-[1α,2β(2R*,3S*),4α,4aβ,10aβ]]-3-(Allyloxycarbonyl)amino-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester By analogy with Example 1a, 65 mg (0.23 mmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol is reacted using (3R,4S)-1-(allyloxycarbonyl)-3-triisopropylsilyloxy-4-(3-thienyl)-2-azetidinone, which has been produced analogously to the process that is described in Tetrahedron 1992 on page 6985 ff. After working-up and purification, 119 mg (172 μmol, 75%) of the title compound is isolated as a colorless oil.

EXAMPLE 57

[1R-[1α,2β(2R*,3S)(E,E,2S or 2R)*),4α,4aβ,10aβ]]-3-[2-[[Methoxy(3,7,11-trimethyl-2,6,10-dodecatrienyl)-phosphinyl]oxy]acetyl]amino-2-hydroxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester 1.9 mg (2.1 μmol) of the compound that is presented according to Example 56a is reacted analogously to Example 1. After working-up and purification, 1.4 mg (1.8 μmol, 88%) of the title compound is isolated as a colorless oil.

$^1$H-NMR (CDCl$_3$): δ=0.83 (3H), 0.91 (3H), 1.03 (3H), 1.46–1.74 (13H), 1.90–2.13 (8H), 2.29 (1H), 2.55 (1H), 2.62 (1H), 2.70 (1H), 2.77 (1H), 3.09 (1H), 3.41 (1H), 3.70 (3H), 4.38–4.58 (3H), 5.00–5.19 (5H), 5.52 (1H), 5.14 (1H), 7.14 (1H), 7.20–7.36 (4H), 7.41–7.59 (3H) ppm.

EXAMPLE 58

[1R-[1α,2β(2R*,3S*),4α,4aβ,9β,10aβ]]-3-(Ethoxycarbonyl)amino-2-hydroxy-3-[4-(1-oxohexadecyloxy)phenyl]-propanoic acid-9-methyl-1,2,3,4,4a,9,10,10a-octahydro-1,12,12-trimethyl-4a,10a-epoxy-1,4-methanophenanthren-2-ylester 9.9 mg (11 μmol) of the compound that is presented according to Example 58a is reacted analogously to Example 1. After working-up and purification, 2.2 mg (2.8 μmol, 26%) of the title compound is isolated as a colorless oil.

$^1$H-NMR (CDCl$_3$): δ=0.79 (3H), 0.88 (3H), 0.90 (3H), 1.02 (3H), 1.13–1.46 (24H), 1.19 (3H), 1.40 (3H), 1.60–1.80 (3H), 2.07 (1H), 2.20 (1H), 2.29 (1H), 2.51 (2H), 2.67 (1H), 3.07 (1H), 3.21 (1H), 4.09 (2H), 4.52 (1H), 4.92 (1H), 5.27 (1H), 6.25 (1H), 7.01 (2H), 7.12–7.32 (3H), 7.43–7.57 (3H) ppm.

EXAMPLE 58a

[1R-[1α,2β(2R*,3S*),4α,4aβ,9β,10aβ]]-3-(Ethoxycarbonyl)amino-2-triisopropylsilyloxy-3-[4-(1- oxohexadecyloxy)phenyl]-propanoic acid-9-methyl-1,2,3,4,4a,9,10,10a-octahydro-1,12,12-trimethyl-4a,10a-epoxy-1,4-methanophenanthren-2-ylester The solution of 10 mg (14.5 μmol) of the compound, presented according to Example 20b, in 0.3 ml of anhydrous dichloromethane is mixed under an atmosphere of dry argon at 0° C. with 5.7 μl of palmitic acid chloride, 3.0 μl of triethylamine, and it is allowed to react for 30 minutes at 0° C. It is poured into a saturated sodium bicarbonate solution, extracted several times with ethyl acetate, the combined organic extracts are washed with a saturated sodium chloride solution and dried on magnesium sulfate. The residue that is obtained after filtration and removal of the solvent is purified by chromatography on an analytical thin-layer plate. A mixture of n-hexane and ethyl acetate is used as a mobile solvent; a mixture of dichloromethane and methanol is used as an eluant. 9.9 mg (10.6 μmol, 73%) of the title compound is isolated as a colorless oil.

EXAMPLE 59

[1R-[1α,2β(2R*,3S(2S)*),4α,4aβ,9β, 10aβ]]-3-(Ethoxycarbonyl)amino-2-hydroxy-3-[4-[4-[3-[4-[[bis(phenylmethoxy)phosphinyl]oxy]phenyl]-2-[[(1,1-dimethylethoxy)carbonyl]amino]-1-oxopropoxy]phenyl]-propanoic acid-9-methyl-1,2,3,4,4a,9,10,10a-octahydro-1,12,12-trimethyl-4a,10a-epoxy-1,4-methanophenanthren-2-ylester 33 mg (29 μmol) of the compound that is presented according to Example 59a is reacted analogously to Example 1. After working-up and purification, 18 mg (17 μmol, 59%) of the title compound is isolated as a colorless oil.

$^1$H-NMR (CDCl$_3$): δ=0.78 (3H), 0.89 (3H), 1.02 (3H), 1.20 (3H), 1.39 (3H), 1.44 (9H), 2.09 (1H), 2.16 (1H), 2.28 (1H), 2.68 (1H), 2.99–3.31 (4H), 4.09 (2H), 4.52 (1H), 4.73 (1H), 4.92 (1H), 4.99–5.18 (4H), 5.28 (1H), 6.27 (1H), 6.75 (2H), 6.89–7.56 (22H) ppm.

EXAMPLE 59a

[1R-[1α,2β(2R*,3S(2S)*),4α,4aβ,9β, 10aβ]]-3-(Ethoxycarbonyl)amino-2-triisopropylsilyloxy-3-[4-[4-[3-[4-[[bis(phenylmethoxy)phosphinyl]oxy]phenyl]-2-[[(1,1-dimethylethoxy)carbonyl]amino]-1-oxopropoxy]phenyl]-propanoic acid-9-methyl-1,2,3,4,4a,9,10,10a-octahydro-1,12,12-trimethyl-4a,10a-epoxy-1,4-methanophenanthren-2-ylester By analogy with Example 46, 20 mg (29 μmol) of the compound that is presented according to Example 20b is reacted using N-boc-L-serine-O-dibenzylphosphate. After working-up and purification, 33 mg (27 μmol, 94%) of the title compound is isolated as a colorless oil.

EXAMPLE 60

[1R-[1α,2β(2R*,3S*),4α,4aβ,9β, 10aβ]]-3-(Methoxycarbonyl)amino-2-hydroxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 11 mg (16.6 μmol) of the compound that is presented according to Example 60a is reacted analogously to Example 1. After working-up and purification, 7.5 mg (14.8 μmol, 89%) of the title compound is isolated as a colorless oil.

$^1$H-NMR (CDCl$_3$): δ=0.78 (3H), 0.89 (3H), 1.02 (3H), 1.40 (3H), 1.56 (1H), 2.10 (1H), 2.18 (1H), 2.24 (1H), 2.68 (1H), 3.09 (1H), 3.63 (3H), 4.56 (1H), 4.92 (1H), 5.30 (1H), 6.49 (1H), 7.13–7.56 (6H), 8.52 (2H) ppm.

EXAMPLE 60a

[1R-[1α,2β(2R*,3S*),4α,4aβ,9β, 10aβ]]-3-(Methoxycarbonyl)amino-2-triisopropylsilyloxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 11.4 mg (40 μmol) of compound A, presented according to Example 33b, is reacted using (3R,4S)-1-(methoxycarbonyl)-3-triisopropylsilyloxy-4-(4-pyridyl)-2-azetidinone, which has been produced analogously to the process that is described in Tetrahedron 1992 on page 6985 ff. After working-up and purification, 11 mg (16.6 μmol, 42%) of the title compound is isolated as a colorless oil.

EXAMPLE 61

[1R-[1α,2β(1R*,2R(2R,3S)* or 1S*,2S(2R,3S)*),4α,4aβ, 9β,10aβ]]-2-[[3-(Ethoxycarbonyl)amino-2-hydroxy-3-(4-pyridyl)-1-oxopropyl]amino]cyclohexane-carboxylic acid-9-methyl-1,2,3,4,4a,9,10,10a-octahydro-1,12,12-trimethyl-4a,10a-epoxy-1,4-methanophenanthren-2-ylester 4.4 mg (5.5 μmol) of the compound is presented according to Example 61a is reacted analogously to Example 1. After working-up and purification, 1.6 mg (2.5 μmol, 46%) of the title compound is isolated as a colorless oil.

$^1$H-NMR (CDCl$_3$): δ=0.74 (3H), 0.89 (3H), 1.02 (3H), 1.21 (3H), 1.28 (3H), 1.37 (2H), 1.50–1.81 (6H), 1.88 (1H), 2.14 (2H), 2.24 (1H), 2.43 (1H), 2.61 (1H), 3.10 (1H), 3.86–4.13 (3H), 4.20 (1H), 4.69 (1H), 4.79 (1H), 4.98 (1H), 6.33 (1H), 6.61 (1H), 6.99–7.42 (6H), 8.38 (2H) ppm.

EXAMPLE 61a

[1R-[1α,2β(1R*,2R(2R,3S)* or 1S*,2S(2R,3S)*),4α,4aβ, 9β,10aβ]]-2-[[3-(Ethoxycarbonyl)amino-2-triisopropylsilyloxy-3-(4-pyridyl)-1-oxopropyl]aminocyclohexanecarboxylic acid-9-methyl-1,2,3,4,4a,9,10,10a-octahydro-1,12,12-trimethyl-4a,10a-epoxy-1,4-methanophenanthren-2-ylester By analogy with Example 40a, 13 mg (32 μmol) of the compound that is presented according to Example 61b is reacted using the acid that is presented according to Example 42d. After working-up and purification, 4.4 mg (5.5 μmol, 17%) of the title compound is isolated as a colorless oil.

EXAMPLE 61b

[1R-[1α,2β(1R*,2R(2R,3S)* or 1S*,2S(2R,3S)*),4α,4aβ, 9β,10aβ]]-2-Aminocyclohexanecarboxylic acid-9-methyl-1,2,3,4,4a,9,10,10a-octahydro-1,12,12-trimethyl-4a,10a-epoxy-1,4-methanophenanthren-2-ylester 18.5 mg (38 μmol) of compound B, presented according to Example 61c, is reacted analogously to Example 40b. After working-up and purification, 13 mg (32 μmol, 85%) of the title compound is isolated as a colorless oil.

EXAMPLE 61c

[1R-[1α,2β(1R*,2R(2R,3S)*), 4α,4aβ,9β,10aβ]]-2-(Allyloxycarbonyl)aminocyclohexanecarboxylic acid-9-methyl-1,2,3,4,4a,9,10,10a-octahydro-1,12,12-trimethyl-4a,10a-epoxy-1,4-methanophenanthren-2-ylester (A) and
[1R-[1α,2β(1S*,2S(2R,3S)*), 4α,4aβ,9β,10aβ]]-2-(allyloxycarbonyl)aminocyclohexanecarboxylic acid-9-methyl-1,2,3,4,4a,9,10,10a-octahydro-1,12,12-trimethyl-4a,10a-epoxy-1,4-methanophenanthren-2-ylester (B)

By analogy with Example 46, 39.6 mg (139 μmol) of compound A, presented according to Example 33b, is reacted using the acid that is presented according to Example 61d. After working-up and purification, 23 mg (47 μmol, 34%) of title compound B as well as 33 mg (67 μmol, 48%) of title compound A are isolated, in each case as a colorless oil.

EXAMPLE 61d (1RS,2RS)-2-(Allyloxycarbonyl) aminocyclohexanecarboxylic acid 180 mg (0.71 mmol) of the compound that is presented according to Example 61e is reacted analogously to Example 40d. After working-up and purification, 95 mg (418 μmol, 59%) of the title compound is isolated as a colorless oil.

EXAMPLE 61e (1RS,2RS)-2-(Allyloxycarbonyl) aminocyclohexanecarboxylic acid ethyl ester The solution of 166 mg (0.8 mmol) (±)-trans-2-amino-1-carboxylic acid ethyl ester hydrochloride in 8 ml of anhydrous dichloromethane is mixed at 0° C. under an atmosphere of dry argon with 586 mg of 4-dimethylaminopyridine, 0.26 ml of allyl chloroformate, and it is stirred for 18 hours at 23° C. It is poured into a saturated sodium bicarbonate solution, extracted several times with ethyl acetate, the combined organic extracts are washed with saturated sodium chloride solution and dried on magnesium sulfate. The residue that is obtained after filtration and removal of the solvent is further reacted without purification. 190 mg (744 μmol, 93%) of the title compound is isolated as a colorless oil.

EXAMPLE 62

[1R-[1α,2β(1S*,2S(2R,3S)* or 1R*,2R(2R,3S)*),4α,4aβ, 9β,10aβ]]-2-[[3-(Ethoxycarbonyl)amino-2-hydroxy-3-(4-pyridyl)-1-oxopropyl]amino]cyclohexanecarboxylic acid-9-methyl-1,2,3,4,4a,9,10,10a-octahydro-1,12,12-trimethyl-4a,10a-epoxy-1,4-methanophenanthren-2-ylester 11 mg (13.7 μmol) of the compound that is presented according to Example 62a is reacted analogously to Example 1. After working-up and purification, 4.9 mg (7.6 μmol, 55%) of the title compound is isolated as a colorless oil.

$^1$H-NMR (CDCl$_3$): δ=0.77 (3H), 0.91 (3H), 1.03 (3H), 1.15–2.17 (12H), 1.23 (3H), 1.32 (3H), 2.32 (1H), 2.60 (1H), 2.68 (1H), 3.03 (1H), 3.82 (1H), 4.08 (2H), 4.30 (1H), 4.80 (1H), 5.11 (1H), 5.94 (1H), 7.07–7.34 (6H), 7.39 (1H), 8.23 (2H) ppm.

EXAMPLE 62a

[1R-[1α,2β(1S*,2S(2R,3S)* or 1R*,2R(2R,3S)*),4α,4aβ, 9β,10aβ]]-2-[[3-(Ethoxycarbonyl)amino-2-triisopropylsilyloxy-3-(4-pyridyl)-1-oxopropyl]amino] cyclohexanecarboxylic acid-9-methyl-1,2,3,4,4a,9,10,10a-octahydro-1,12,12-trimethyl-4a,10a-epoxy-1,4-methanophenanthren-2-ylester By analogy with Example 40a, 18 mg (44 μmol) of compound, presented according to Example 62b, is reacted using the acid that is presented according to Example 42d. After working-up and purification, 11 mg (13.7 μmol, 31%) of the title compound is isolated as a colorless oil.

EXAMPLE 62b

[1R-[1α,2β(1S*,2S(2R,3S)* or 1R*,2R(2R,3S)*),4α,4aβ, 9β,10aβ]]-2-Aminocyclohexanecarboxylic acid-9-methyl-1,2,3,4,4a,9,10,10a-octahydro-1,12,12-trimethyl-4a,10a-epoxy-1,4-methanophenanthren-2-ylester 28 mg (57 μmol) of compound A, presented according to Example 61c, is reacted analogously to Example 40b. After working-up and purification, 18 mg (44 μmol, 77%) of the title compound is isolated as a colorless oil.

EXAMPLE 63

[1R-[1α,2β(2R*,3S*),4α,4aβ,9α,10aβ]]-3-(Ethoxycarbonyl)amino-2-hydroxy-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester 24 mg (35 μmol) of the compound that is presented according to Example 63a is reacted analogously to Example 1. After working-up and purification, 11.7 mg (22 μmol, 62%) of the title compound is isolated as a colorless oil.

$^1$H-NMR (CDCl$_3$): δ=0.77 (3H), 0.90 (3H), 1.06 (3H), 1.21 (3H), 1.43 (3H), 1.58 (1H), 1.71 (1H), 2.30 (1H), 2.46 (1H), 2.74 (1H), 3.03 (1H), 3.13 (1H), 4.09 (2H), 4.48 (1H), 4.83 (1H), 5.19 (1H), 5.26 (1H), 6.67 (2H), 6.85 (1H), 7.13–7.40 (5 H), 7.51 (1H) ppm.

EXAMPLE 63a

[1R-[1α,2β(2R*,3S*),4α,4aβ,9α,10aβ]]-3-(Ethoxycarbonyl)amino-2-triisopropylsilyloxy-3-(4-hydroxyphenyl)-propanoic acid-9-methyl-1,2,3,4,4a,9, 10,10a-octahydro-1,12,12-trimethyl-4a,10a-epoxy-1,4-methanophenanthren-2-ylester By analogy with Example 1a, 14.9 mg (52 μmol) of compound A, presented according to Example 43b, is reacted using (3R,4S)-1-ethoxycarbonyl-3-triisopropylsilyloxy-4-(4-hydroxyphenyl)-2-azetidinone, which has been produced analogously to the process that is described in Tetrahedron 1992 on page 6985 ff. After working-up and purification, 24 mg 35 μmol, 67%) of the title compound is isolated as a colorless oil.

EXAMPLE 64

[1R-[1α,2β(2R*,3S*),4α,4aβ,9β,10aβ]]-3-[[[(1-Methyl) ethylamino]carbonyl]amino]-2-hydroxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 13.4 mg (19 μmol) of the compound that is presented according to Example 64a is reacted analogously to Example 1. After working-up and purification, 8.9 mg (16.7 μmol, 88%) of the title compound is isolated as a colorless oil.

$^1$H-NMR (CDCl$_3$): δ=0.63 (3H), 0.74 (3H), 0.84 (3H), 0.94 (3H), 1.05 (3H), 1.39 (3H), 1.76 (1H), 2.18 (2H), 2.45 (1H), 2.77 (1H), 3.14 (1H), 3.66 (1H), 4.62 (1H), 4.80 (1H), 5.11 (2H), 6.43 (1H), 7.15–7.37 (5H), 7.52 (1H), 8.53 (2H) ppm.

EXAMPLE 64a

[1R-[1α,2β(2R*,3S*),4α,4aβ,9β,10aβ]]-3-[[[(1-Methyl) ethylamino]carbonyl]amino]-2-triisopropylsilyloxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 14.2 mg (23 μmol) of the compound that is presented according to Example 42b is reacted using (3R,4S)-1-[[(1-methyl)ethylamino]carbonyl]-3-triisopropylsilyloxy-4-(4-pyridyl)-2-azetidinone, which has been produced analogously to the process that is described in Tetrahedron 1992 on page 6985 ff. After working-up and purification, 13.4 mg (19 μmol, 84%) of the title compound is isolated as a colorless oil.

EXAMPLE 65

[1R-[1α,2β(2R*,3S*),4α,4aβ,9β,10aβ]]-3-(Butoxycarbonyl)amino-2-hydroxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 14.8 mg (21 μmol) of the compound that is presented according to Example 65a is reacted analogously in Example 1. After working-up and purification, 10.4 mg (19 μmol, 90%) of the title compound is isolated as a colorless oil.

$^1$H-NMR (CDCl$_3$): δ=0.54–0.95 (11H), 1.02 (3H), 1.20–1.47 (4H), 1.50–1.63 (2H), 2.09 (1H), 2.16 (1H), 2.27 (1H), 2.68 (1H), 3.08 (1H), 3.39 (broad, 1H), 3.82 (1H), 4.05 (1H), 4.56 (1H), 4.93 (1H), 5.28 (1H), 6.30 (1H), 7.12–7.33 (3H), 7.36–7.53 (3H), 8.52 (2H) ppm.

EXAMPLE 65a

[1R-[1α,2β(2R*,3S*),4α,4aβ,9β,10aβ]]-3-(Butoxycarbonyl)amino-2-triisopropylsilyloxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 11.4 mg (40 μmol) of compound A, presented according to Example 33b, is reacted using (3R,4S)-1-butoxycarbonyl-3-triisopropylsilyloxy-4-(4-pyridyl)-2-azetidinone, which has been produced analogously to the process that is described in Tetrahedron 1992 on page 6985 ff. After working-up and purification, 14.8 mg (21 μmol, 53%) of the title compound is isolated as a colorless oil.

EXAMPLE 66

[1R-[1α,2β(2R*,3S*),4α,4aβ,9β,10aβ]]-3-[(1-Oxopropyl)amino]-2-hydroxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 10.9 mg (16 μmol) of the compound that is presented according to Example 66a is reacted analogously to Example 1. After working-up and purification, 6.7 mg (13 μmol, 81%) of the title compound is isolated as a colorless oil.

$^1$H-NMR (CDCl$_3$): δ=0.76 (3H), 0.90 (3H), 0.98 (3H), 1.10 (3H), 1.33 (3H), 1.68 (1H), 2.09 (2H), 2.30 (3H), 2.69 (1H), 3.08 (1H), 3.72 (1H, broad), 4.57 (1H), 5.05 (1H), 5.49 (1H), 7.10 (1H), 7.16 (1H), 7.21–7.40 (4H), 7.48 (1H), 8.52 (2H) ppm.

EXAMPLE 66a

[1R-[1α,2β(2R*,3S*),4α,4aβ,9β,10aβ]]-3-[(1-Oxopropyl)amino]-2-triisopropylsilyloxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 11.4 mg (40 μmol) of compound A, presented according to Example 33b, is reacted using (3R,4S)-1-(1-oxopropyl)-3-triisopropylsilyloxy-4-(4-pyridyl)-2-azetidinone, which has been produced analogously to the process that is described in Tetrahedron 1992 on page 6985 ff. After working-up and purification, 10.9 mg (16 μmol, 41%) of the title compound is isolated as a colorless oil.

EXAMPLE 67

[1R-[1α,2β(2R*,3S*),4α,4aβ,9β,10aβ]]-3-[(1-Oxobutyl)amino]-2-hydroxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 10.4 mg (15 μmol) of the compound that is presented according to Example 67a is reacted analogously to Example 1. After working-up and purification, 6.3 mg (12 μmol, 81%) of the title compound is isolated as a colorless oil.

$^1$H-NMR (CDCl$_3$): δ=0.78 (3H), 0.82 (3H), 0.90 (3H), 0.99 (3H), 1.35 (3H), 1.62 (2H), 1.70 (1H), 2.09 (2H), 2.25 (2H), 2.32 (1H), 2.70 (1H), 3.09 (1H), 3.60 (1H, broad), 4.57 (1H), 5.07 (1H), 5.48 (1H), 7.12 (1H), 7.18 (1H), 7.21–7.40 (4H), 7.48 (1H), 8.52 (2 H) ppm.

EXAMPLE 67a

[1R-[1α,2β(2R*,3S*),4α,4aβ,9β,10aβ]]-3-[(1-Oxobutyl)amino]-2-triisopropylsilyloxy-3-(4-pyridyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 11.4 mg (40 μmol) of compound A, presented according to Example 33b, is reacted using (3R,4S)-1-(1-oxobutyl)-3-triisopropylsilyloxy-4-(4-pyridyl)-2-azetidinone, which has been produced analogously to the process that is described in Tetrahedron 1992 on page 6985 ff. After working-up and purification, 10.4 mg (15 μmol, 38%) of the title compound is isolated as a colorless oil.

EXAMPLE 68

[1R-[1α,2β(2R*,3S*),4α,4aβ,9β,10aβ]]-3-[(Methoxycarbonyl)amino]-2-hydroxy-3-(3-thienyl)-propanoic acid-9-methyl-1,2,3,4,4a,9,10,10a-octahydro-1,12,12-trimethyl-4a,10a-epoxy-1,4-methanophenanthren-2-ylester 32 mg (48 μmol) of the compound that is presented according to Example 68a is reacted analogously to Example 1. After working-up and purification, 15 mg (29 μmol, 61%) of the title compound is isolated as a colorless oil.

$^1$H-NMR (CDCl$_3$): δ=0.77 (3H), 0.88 (3H), 1.03 (3H), 1.41 (3H), 1.51 (1H), 2.10 (1H), 2.21 (1H), 2.25 (1H), 2.65 (1H), 3.09 (1H), 3.28 (1H), 3.67 (3H), 4.51 (1H), 4.88 (1H), 5.36 (1H), 6.43 (1H), 7.13–7.33 (5H), 7.40 (1H), 7.50 (1H) ppm.

EXAMPLE 68a

[1R-[1α,2β(2R*,3S*),4α,4aβ,9β,10aβ]]-3-[(Methoxycarbonyl)amino]-2-triisopropylsilyloxy-3-(3-thienyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 17 mg (60 μmol) of compound A, presented according to Example 33b, is reacted using (3R,4S)-1-(methoxycarbonyl)-3-triisopropylsilyloxy-4-3-thienyl)-2-azetidinone, which has been produced analogously to the process that is described in Tetrahedron 1992 on page 6985 ff. After working-up and purification, 32 mg (48 μmol, 80%) of the title compound is isolated as a colorless oil.

EXAMPLE 69

[1R-[1α,2β(2R*,3S*),4α,4aβ,9β,10aβ]]-3-(Ethoxycarbonyl)amino-2-hydroxy-3-(4-thienyl)- propanoic acid-9-methyl-1,2,3,4,4a,9,10,10a-octahydro-1,12,12-trimethyl-10a-hydroxy-1,4-methanophenanthren-2-ylester 7.0 mg (13 μmol) of the compound that is presented according to Example 33 is reacted analogously to Example 9a. After working-up and purification, 1.0 mg (2 μmol, 14%) of the title compound is isolated as a colorless oil.

$^1$H-NMR (CDCl$_3$): δ=0.55 (3H), 0.93 (3H), 1.02 (3H), 1.25 (3H), 1.41 (3H), 1.47 (1H), 1.80 (1H), 2.18 (1H), 2.47 (1H), 2.75 (1H), 3.02 (1H), 3.10 (2H), 3.38 (1H, broad), 4.12 (2H), 4.66 (1H), 5.22 (1H), 5.33 (1H), 6.22 (1H), 7.10–7.25 (4H), 7.36 (2H), 8.58 (2H) ppm.

EXAMPLE 70

[1R-[1α,2β(2R*,3S*),4α,4aβ,9α,10aβ]]-3-(Ethoxycarbonyl)amino-2-hydroxy-3-(4-pyridyl)-propanoic acid-9-methyl-1,2,3,4,4a,9,10,10a-octahydro-1,12,12-trimethyl-10a-hydroxy-1,4-methanophenanthren-2-ylester 5.4 mg (8 μmol) of the compound that is presented according to Example 70a is reacted analogously to Example 1. After working-up and purification, 1.0 mg (1.9 μmol, 24%) of the title compound is isolated as a colorless oil.

$^1$H-NMR (CDCl$_3$): δ=0.56 (3H), 0.96 (3H), 1.01 (3H), 1.20–1.33 (3H), 1.42 (3H), 1.53–1.84 (4H), 2.53 (1H), 2.82 (1H), 2.92 (1H), 3.11 (1H), 3.45 (1H), 4.10 (2H), 4.69 (1H), 5.22 (1H), 5.45 (1H), 5.95 (1H), 7.12–7.43 (6H), 8.59 (2H) ppm.

EXAMPLE 70a

[1R-[1α,2β(2R*,3S*),4α,4aβ,9α,10aβ]]-3-(Ethoxycarbonyl)amino-2-triisopropylsilyloxy-3-(4-pyridyl)-propanoic acid-9-methyl-1,2,3,4,4a,9,10,10a-octahydro-1,12,12-trimethyl-10a-hydroxy-1,4-methanophenanthren-2-ylester By analogy with Example 1a, 14.3 mg (50 μmol) of the compound that is presented according to Example 70b is reacted using (3R,4S)-1-(ethoxycarbonyl)-3-triisopropylsilyloxy-4-(4-pyridyl)-2-azetidinone, which has been produced analogously to the process that is described in Tetrahedron 1992 on page 6985 ff. After working-up and purification, 15.7 mg (23 μmol, 46%) of the title compound is isolated as a colorless oil.

EXAMPLE 70b

[1R-(1α,2β,4α,4aβ,9α,10aβ)]-9-Methyl-1,2,3,4,4a,9,10,10a-octahydro-1,12,12-trimethyl-10a-hydroxy-1,4-methanophenanthren-2-ol The solution of 100 mg (354 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol, which has been produced analogously to the process that is described in J. Am. Chem. Soc. 1992, on page 5879 ff, in 3.5 ml of anhydrous tetrahydrofuran is mixed with 40 mg of tris-triphenylphosphinerhodium(I)-chloride and hydrogenated under an atmosphere of hydrogen while being stirred vigorously. After hydrogen absorption is completed, it is concentrated by evaporation and chromatographed on about 70 ml of fine silica gel with a mixture of n-hexane and ethyl acetate. 14.3 mg (50 μmol, 14%) of the title compound is isolated as a colorless solid in addition to the products that are mentioned in Example 33b under Variant B.

EXAMPLE 71

[1R-[1α,2β(2R*,3S*),4α,4aβ,9β,10aβ]]-3-(Methoxycarbonyl)amino-2-hydroxy-3-(4-pyridyl)-propanoic acid-9-methyl-1,2,3,4,4a,9,10,10a-octahydro-1,12,12-trimethyl-10a-hydroxy-1,4-methanophenanthren-2-ylester 7.7 mg (15 μmol) of the compound that is presented according to Example 60 is reacted analogously to Example 9a. After working-up and purification, 1.3 mg (2.6 μmol, 17%) of the title compound is isolated as a colorless oil.

$^1$H-NMR (CDCl$_3$): δ=0.54 (3H), 0.93 (3H), 1.01 (4H), 1.41 (3H), 1.46 (1H), 1.80 (1H), 2.18 (1H), 2.48 (1H), 2.75 (1H), 3.02 (1H), 3.09 (1H), 3.12 (1H), 3.67 (3H), 4.66 (1H), 5.20 (1H), 5.32 (1H), 6.42 (1H), 7.09–7.31 (4H), 7.36 (2H), 8.57 (2H) ppm.

EXAMPLE 72

[1R-[1α,2β(2R*,3S*),4α,4aβ,9β,10aβ]]-3-(Ethoxycarbonyl)amino-2-hydroxy-3-(3-pyridyl)-propanoic acid-9-methyl-1,2,3,4,4a,9,10,10a-octahydro-1,12,12-trimethyl-4a,10a-hydroxy-1,4-methanophenanthren-2-ylester 60 mg (88 μmol) of the compound that is presented according to Example 72a is reacted analogously to Example 1. After working-up and purification, 32 mg (61 μmol, 70%) of the title compound is isolated as a colorless oil.

$^1$H-NMR (CDCl$_3$): δ=0.78 (3H), 0.88 (3H), 1.02 (3H), 1.18 (3H), 1.39 (3H), 1.66 (1H), 2.09 (1H), 2.22 (1H), 2.29 (1H), 2.68 (1H), 3.07 (1H), 3.41 (broad, 1H), 4.10 (2H), 4.56 (1H), 4.91 (1H), 5.31 (1H), 6.38 (1H), 7.10–7.37 (4H), 7.49 (1H), 7.88 (1H), 8.50 (1H), 8.25 (1H) ppm.

EXAMPLE 72a

[1R-[1α,2β(2R*,3S*),4α,4aβ,9β,10aβ]]-3-(Ethoxycarbonyl)amino-2-triisopropylsilyloxy-3-(3-pyridyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 25 mg (88 μmol) of compound A, presented according to Example 33b, is reacted using (3R,4S)-1-(ethoxycarbonyl)-3-triisopropylsilyloxy-4-(3-pyridyl)-2-azetidinone, which has been produced analogously to the process that is described in Tetrahedron 1992 on page 6985 ff. After working-up, 60 mg (88 μmol, 100%) of the title compound is isolated as a colorless oil, which is further reacted without purification.

EXAMPLE 73

[1R-[1α,2β(2R*,3S*),4α,4aβ,9β,10aβ]]-3-(Methoxycarbonyl)amino-2-hydroxy-3-(3-thienyl)-propanoic acid-9-methyl-1,2,3,4,4a,9,10,10a-octahydro-1,12,12-trimethyl-10a-hydroxy-1,4-methanophenanthren-2-ylester 8 mg (16 μmol) of the compound that is presented according to Example 68 is reacted analogously to Example 9a. After working-up and purification, 1.5 mg (2.9 μmol, 18%) of the title compound is isolated as a colorless oil.

$^1$H-NMR (CDCl$_3$): δ=0.55 (3H), 0.98 (3H), 1.00 (3H), 1.40 (3H), 1.94 (1H), 2.22 (2H), 2.43 (1H), 2.69 (1H), 3.04 (2H), 3.33 (1H), 3.68 (3H), 4.00 (1H), 4.62 (1H), 5.14 (1H), 5.38 (1H), 5.99 (1H), 7.12 (2H), 7.18–7.35 (4H), 7.42 (1H) ppm.

EXAMPLE 74

[1R-[1α,2β(2R*,3S*),4α,4aβ,9α,10aβ]]-3-(Ethoxycarbonyl)amino-2-hydroxy-3-(4-pyridyl)-propanoic acid-9-hydroxy-9-hydroxymethyl-1,2,3,4,4a,9,10,10a-octahydro-1,12,12-trimethyl-4a,10a-epoxy-1,4-methanophenanthren-2-ylester 28 mg (40 μmol) of the compound that is presented according to Example 74a is reacted analogously to Example 1. After working-up and purification, 5.5 mg (10 μmol, 25%) of the title compound is isolated as a colorless oil.

$^1$H-NMR (CDCl$_3$): δ=0.77 (3H), 0.87 (3H), 1.14 (3H), 1.30 (3H), 1.55 (1H), 2.06 (1H), 2.39 (1H), 2.68 (1H), 3.06 (1H), 3.30 (broad, 2H), 3.97 (1H), 4.10–4.26 (3H), 4.40 (1H), 4.42 (1H), 4.72 (1H), 5.56 (1H), 5.68 (1H), 7.31–7.48 (4H), 7.53 (1H), 7.79 (1H), 8.56 (broad, 2H) ppm.

EXAMPLE 74a

[1R-[1α,2β(2R*,3S*),4α,4aβ,9α,10aβ]]-3-(Ethoxycarbonyl)amino-2-triisopropylsilyloxy-3-(4-pyridyl)-propanoic acid-9-hydroxy-9-hydroxymethyl-1,2,3,4,4a,9,10,10a-octahydro-1,12,12-trimethyl-4a,10a-epoxy-1,4-methanophenanthren-2-ylester Analogously to Example 1a, 12.7 mg (40 μmol) of the compound that is presented according to Example 74b is reacted using (3R,4S)-1-(ethoxycarbonyl)-3-triisopropylsilyloxy-4-(4-pyridyl)-2-azetidinone, which has been produced analogously to the process that is described in Tetrahedron 1992 on page 6985 ff. After working-up, 28 mg (39 μmol, 99%) of the title compound is isolated as a colorless oil, which is further reacted without purification.

EXAMPLE 74b [1R-(1α,2β,4α,4aβ,9α,10aβ)]-9-Hydroxy-9-hydroxymethyl-1,2,3,4,4a,9,10,10a-octahydro-1,12,12-trimethyl-4a,10a-epoxy-1,4-methanophenanthren-2-ol The solution of 77 mg (273 μmol) of [1R-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol, which has been produced analogously to the process that is described in J. Am. Chem. Soc. 1992, on page 5879 ff, in 5.4 ml of acetone is mixed with 273 mg of N-methylmorpholine-N-oxide, 0.55 ml of a 2.5% solution of osmium tetroxide in tert-butanol, 10.8 ml of water, and it is stirred for 1 hour at 40° C. It is cooled to 0° C., mixed with sodium thiosulfate solution and extracted several times with dichloromethane. The combined organic extracts are washed with water and saturated sodium chloride solution and dried on sodium sulfate. The residue that is obtained after filtration and removal of the solvent is purified by chromatography on 2 analytical thin-layer plates. A mixture of n-hexane and ethyl acetate is used as a mobile solvent; a mixture of dichloromethane and methanol is used as an eluant. 37 mg (117 μmol, 43%) of the title compound is isolated as a colorless oil.

EXAMPLE 75

[1R-(1α,2β(2R*,3S*),4α,4aβ,9β,10aβ]]-3-(Methoxycarbonyl)amino-2-hydroxy-3-(4-pyridyl)-propanoic acid-9-methyl-1,2,3,4,4a,9,10,10a-octahydro-1,12,12-trimethyl-4a,10a-dihydroxy-1,4-methanophenanthren-2-ylester The solution of 7.6 mg (15 μmol) of the compound, presented according to Example 60, in 0.4 ml of tetrahydrofuran is mixed with 0.4 ml of water, 40 μl of a 4N hydrochloric acid, and it is stirred under an atmosphere of argon for 18 hours at 23° C. It is neutralized by adding a saturated sodium bicarbonate solution and extracted several times with dichloromethane. The combined organic extracts are washed with saturated sodium chloride solution and dried on sodium sulfate. The residue that is obtained after filtration and removal of the solvent is purified by chromatography on an analytical thin-layer plate. Ethyl acetate is used as a mobile solvent; a mixture of dichloromethane and methanol is used as an eluant. 6.4 mg (12 μmol, 81%) of the title compound is used as a colorless oil.

$^1$H-NMR (CDCl$_3$): δ=0.53 (3H), 0.98 (3H), 0.98 (3H), 1.00 (3H), 1.38 (3H), 1.94 (1H), 2.19 (2H), 2.41 (1H), 2.69 (1H), 3.03 (1H), 3.38 (1H), 3.67 (3H), 4.16 (1H), 4.16 (1H), 4.58 (1H), 5.15 (1H), 5.30 (1H), 6.39 (1H), 7.11 (1H), 7.22 (2H), 7.33 (2H), 7.33 (2H), 7.39 (1H), 8.47 (2H) ppm.

EXAMPLE 76

[1R-(1α,2β(2R*,3S*),4α,4aβ,9α,10aβ]]-3-(Methoxycarbonyl)amino-2-hydroxy-3-(4-pyridyl)-propanoic acid-9-ylidene-9-oxymethylene-1,2,3,4,4a,9,10,10a-octahydro-1,12,12-trimethyl-4a,10a-epoxy-1,4-methanophenanthren-2-ylester 61 mg (90 μmol) of the compound that is presented according to Example 76a is reacted analogously to Example 1. After working-up and purification, 41 mg (79 μmol, 88%) of the title compound is isolated as a colorless oil.

$^1$H-NMR (CDCl$_3$): δ=0.85 (3H), 0.92 (3H), 1.04 (3H), 1.52 (1H), 2.23 (1H), 2.28 (1H), 2.52 (1H), 2.73 (2H), 3.02 (1H), 3.35 (1H), 3.68 (3H), 4.55 (1H), 4.92 (1H), 5.32 (1H), 6.53 (1H), 7.26–7.41 (3H), 7.45 (2H), 7.45 (2H), 7.54 (1H), 8.51 (2H) ppm.

EXAMPLE 76a

[1R-(1α,2β(2R*,3S*),4α,4aβ,9α,10aβ]]-3-(Methoxycarbonyl)amino-2-trimethylsilyloxy-3-(4-pyridyl)-propanoic acid-9-ylidene-9-oxymethylene-1,2,3,4,4a,9,10,10a-octahydro-1,12,12-trimethyl-4a,10a-epoxy-1,4-methanophenanthren-2-ylester By analogy with Example 1a, 55 mg (180 μmol) of the compound that is presented according to Example 76b is reacted using (3R,4S)-1-(methoxycarbonyl)-3-triisopropylsilyloxy-4-(4-pyridyl)-2-azetidinone, which has been produced analogously to the process that is described in Tetrahedron 1992 on page 6985 ff. After working-up and purification, 61 mg (90 μmol, 50%) of the title compound is isolated as a colorless oil.

EXAMPLE 76b [1R-(1α,2β,4α,4aβ,9α,10aβ)]-1,2,3,4,4a,9,10,10a-Octahydro-1,12,12-trimethyl-4a,10a-epoxy-9-ylidene-9-oxymethylene-1,4-methanophenanthren-2-ol The solution of 134 mg (420 μmol) of the diol that is presented according to Example 74b is dissolved in 4 ml of anhydrous toluene, cooled under an atmosphere of dry argon to 3° C., mixed with 190 μl of 1.8-diazabicyclo[5.4.0]undec-7-ene, 83 μl of perfluorobutane-1-sulfonic acid fluoride, and it is stirred for 1 hour. It is poured into a saturated sodium bicarbonate solution, extracted several times with dichloromethane, the combined organic extracts are washed with saturated sodium chloride solution and dried on sodium sulfate. The residue that is obtained after filtration and removal of the solvent is purified by chromatogrphy on about 10 ml of fine silica gel with a mobile solvent mixture of n-hexane and ethyl acetate. 93 mg (311 μmol, 74%) of the title compound is isolated as a colorless oil.

EXAMPLE 77

[1R-[1α,2β(2R*,3S*),4α,4aβ,9α,10aβ]]-3-(Ethoxycarbonyl)amino-2-hydroxy-3-(3-thienyl)-propanoic acid-9-hydroxy-9-acetoxymethyl-1,2,3,4,4a,9,10,10a-octahydro-1,12,12-trimethyl-4a,10a-epoxy-1,4-methanophenenanthren-2-ylester 2.8 mg (3.7 μmol) of the compound that is presented according to Example 77a is reacted analogously to Example 1. After working-up and purification, 1.2 mg (2.0 µmol, 54%) of the title compound is isolated as a colorless oil.

$^1$H-NMR (CDCl$_3$): δ=0.79 (3H), 0.92 (3H), 1.03 (3H), 1.19 (3H), 1.65 (1H), 2.02 (1H), 2.15 (3H), 2.30 (1H), 2.70 (1H), 2.75 (1H), 3.43 (2H), 4.11 (2H), 4.20 (1H), 4.56 (1H), 4.60 (1H), 5.02 (1H), 5.35 (1H), 6.19 (1H), 7.19 (1H), 7.22–7.38 (3H), 7.42 (1H), 7.52 (1H), 7.69 (1H) ppm.

EXAMPLE 77a

[1R-[1α,2β(2R*,3S*),4α,4aβ,9α,10aβ]]-3-(Ethoxycarbonyl)amino-2-triisopropylsilyloxy-3-(3-thienyl)-propanoic acid-9-hydroxy-9-acetoxymethyl-1,2,3,4,4a,9,10,10a-octahydro-1,12,12-trimethyl-4a,10a-epoxy-1,4-methanophenanthren-2-ylester By analogy with Example 1a, 10.7 mg (30 µmol) of the compound that is presented according to Example 77b is reacted using (3R,4S)-1-(ethoxycarbonyl)-3-triisopropylsilyloxy-4-(3-thienyl)-2-azetidinone, which has been produced analogously to the process that is described in Tetrahedron 1992 on page 6985 ff. After working-up and purification, 2.8 mg (3.7 µmol, 12%) of the title compound is isolated as a colorless oil.

EXAMPLE 77b

[1R-(1α,2β,4α,4aβ,9α,10aβ)]-1,2,3,4,4a,9,10,10a-Octahydro-1,12,12-trimethyl-4a,10a-epoxy-9-hydroxy-9-acetoxymethyl-1,4-methanophenanthren-2-ol The solution of 51 mg (161 µmol) of the diol, presented according to Example 74b, in 1.6 ml of anhydrous pyridine is mixed at 3° C. under an atmosphere of dry argon with 18 µl of acetic anhydride, a microspatula tip rull of 4-dimethylaminopyridine, and it is stirred for 1 hour. It is poured into water, extracted several times with dichloromethane, the combined organic extracts are washed with saturated sodium chloride solution and dried on sodium sulfate. The residue that is obtained after filtration and removal of the solvent is purified by chromatography on 3 analytical thin-layer plates. A mixture of n-hexane and ethyl acetate is used as a mobile solvent; a mixture of dichloromethane and methanol is used as an eluant. 36 mg (100 µmol, 62%) of the title compound is isolated as a colorless oil.

EXAMPLE 78

[1R-[1α,2β(2R*,3S*),4α,4aβ,9β,10aβ]]-3-(Methoxycarbonyl)amino-2-hydroxy-3-(4-pyridyl)-propanoic acid-9-methyl-1,2,3,4,4a,9,10,10a-octahydro-1,12,12-trimethyl-4a-methoxy-10a-hydroxy-1,4-methanophenanthren-2-ylester 24 mg (35 µmol) of the compound that is presented according to Example 78a is reacted analogously to Example 1. After working-up and purification, 16.7 mg (31 µmol, 89%) of the title compound is isolated as a colorless oil.

$^1$H-NMR (CDCl$_3$): δ=0.44 (3H), 0.94 (3H), 0.99 (3H), 1.40 (3H), 1.66 (1H), 1.96 (1H), 2.06 (1H), 2.37 (1H), 2.79 (1H), 3.00 (3H), 3.02 (1H), 3.63 (1H), 3.70 (3H), 4.09 (1H), 4.61 (1H), 5.07 (1H), 5.30 (1H), 6.92 (1H), 7.14–7.33 (4H), 7.49 (2H), 8.56 (2H) ppm.

EXAMPLE 78a

[1R-[1α,2β(2R*,3S*),4α,4aβ,9β, 10aβ]]-3-(Methoxycarbonyl)amino-2-triisopropylsilyloxy-3-(4-pyridyl)-propanoic acid-9-methyl-1,2,3,4,4a,9,10,10a-octahydro-1,12,12-trimethyl-4a-methoxy-10a-hydroxy-1,4-methanophenanthren-2-ylester By analogy with Example 1a, 22 mg (70 µmol) of the compound that is presented according to Example 78b is reacted using (3R,4S)-1-(methoxycarbonyl)-3-triisopropylsilyloxy-4-(4-pyridyl)-2-azetidinone, which has been produced analogously to the process that is described in Tetrahedron 1992 on page 6985 ff. After working-up and purification, 24 mg (35 µmol, 50%) of the title compound is isolated as a colorless oil.

EXAMPLE 78b

[1R-(1α,2β,4α,4aβ,9β,10aβ)]-1,2,3,4,4a,9,10,10a-Octahydro-1,12,12-trimethyl-4a-methoxy-10a-hydroxy-9-methyl-1,4-methanophenanthren-2-ol The solution of 20 mg (70 µmol) of compound A, presented according to Example 33b, in 1 ml of anhydrous methanol is mixed at 23° C. under an atmosphere of dry argon with 200 mg of Dovex®, and it is stirred for 1 hour. It is filtered, concentrated by evaporation, and the residue is purified by chromatography on 1 analytical thin-layer plate. A mixture of n-hexane and ethyl acetate is used as a mobile solvent; a mixture of dichloromethane and methanol is used as an eluant. 22 mg (70 µmol, 100%) of the title compound is isolated as a colorless oil.

EXAMPLE 79

[1R-[1α,2β(2R*,3S*),4α,4aβ,9α,10aβ]]-3-(Methoxycarbonyl)amino-2-hydroxy-3-(4-pyridyl)-propanoic acid-9-hydroxy-9-acetoxymethyl-1,2,3,4,4a,9,10,10a-octahydro-1,12,12-trimethyl-4a,10a-epoxy-1,4-methanophenanthren-2-ylester 9.4 mg (13 µmol) of the compound that is presented according to Example 79a is reacted analogously to Example 1. After working-up and purification, 4.8 mg (8.3 µmol, 64%) of the title compound is isolated as a colorless oil.

$^1$H-NMR (CDCl$_3$): β=0.79 (3H), 0.96 (3H), 1.09 (3H), 1.72 (1H), 2.06 (1H), 2.13 (3H), 2.39 (1H), 2.68 (1H), 2.98 (1H), 3.56 (3H), 4.10 (1H), 4.30 (1H), 4.39 (1H), 4.69 (1H), 4.92 (1H), 5.52 (1H), 5.75 (1H), 7.23–7.58 (5H), 7.78 (1H), 8.65 (2H) ppm.

EXAMPLE 79a

[1R-[1α,2β(2R*,3S*),4α,4aβ,9α,10aβ]]-3-(Methoxycarbonyl)amino-2-triisopropylsilyloxy-3-(4-pyridyl)-propanoic acid-9-hydroxy-9-acetoxymethyl-1,2,3,4,4a,9,10,10a-octahydro-1,12,12-trimethyl-4a,10a-epoxy-1,4-methanophenanthren-2-ylester 13 mg (19 µmol) of the compound that is presented according to Example 78b is reacted analogously to Example 77b. After working-up and purification, 9.4 mg (13 µmol, 67%) of the title compound is isolated as a colorless oil.

EXAMPLE 78b

By analogy with Example 1a, 19 mg (60 µmol) of the compound that is presented according to Example 74b is reacted using (3R,4S)-1-(methoxycarbonyl)-3-triisopropylsilyloxy-4-(4-pyridyl)-2-azetidinone, which has been produced analogously to the process that is described in Tetrahedron 1992 on page 6985 ff. After working-up and purification, 13 mg (19 µmol, 31%) of the title compound is isolated as a colorless oil.

EXAMPLE 80

[1R-[1α,2β(2R*,3S*),4α,4aβ,9β,10aβ]]-3-[[[(Methyl)ethylamino]carbonyl]amino]-2-hydroxy-3-(3-thienyl)-propanoic acid-9-methyl-1,2,3,4,4a,9,10,10a-octahydro-1,12,12-trimethyl-4a,10a-epoxy-1,4methanophenanthren-2-ylester 3 mg (4.3 µmol) of the compound that is presented according to Example 80a is reacted analogously to Example 1. After working-up and purification, 1.6 mg (3.0 μmol, 70%) of the title compound is isolated as a colorless oil.

$^1$H-NMR (CDCl$_3$): δ=0.72 (3H), 0.79 (3H), 0.82 (3H), 0.92 (3H), 1.04 (3H), 1.39 (3H), 1.69 (1H), 2.17 (2H), 2.39 (1H), 2.72 (1H), 3.13 (1H), 3.21 (1H), 3.73 (1H), 4.56 (1H), 4.72 (1H), 5.08 (1H), 5.25 (1H), 6.15 (1H), 7.08 (1H), 7.14–7.35 (5H), 7.49 (1H) ppm.

EXAMPLE 80a

[1R-[1α,2β(2R*,3S*),4α,4aβ,9β,10aβ]]-3-[[[(1-Methyl)ethylamino]carbonyl]amino]-2-triisopropylsilyloxy-3-(3-thienyl)-propanoic acid-9-methyl-1,2,3,4,4a,9,10,10a-octahydro-1,12,12-trimethyl-4a,10a-epoxy-1,4-methanophenanthren-2-ylester 18 mg (26 μmol) of the compound that is presented according to Example 80b is hydrogenated analogously to Example 9a. After working-up and purification, 3 mg (4.3 μmol, 17%) of the title compound is isolated as a colorless oil.

EXAMPLE 80b

[1R-[1α,2β(2R*,3S*),4α,4aβ,10aβ]]-3-Amino-2-triisopropylsilyloxy-3-(3-thienyl)-propanoic acid-9-methylene-1,2,3,4,4a,9,10,10a-octahydro-1,12,12-trimethyl-4a,10a-epoxy-1,4-methanophenanthren-2-ylester The solution of 20 mg (33 μmol) of the amine, presented according to Example 40b, in 0.3 ml of anhydrous dichloromethane is mixed under an atmosphere of dry argon at 0° C. with 14 μl of triethylamine, 12 mg of 4-dimethylaminopyridine, 9.7 μl of isopropylisocyanate, and it is stirred for 1 hour. It is poured into water, extracted several times with dichloromethane, the combined organic extracts are washed with saturated sodium chloride solution and dried on sodium sulfate. The residue that is obtained after filtration and removal of the solvent is purified by chromatography on 2 analytical thin-layer plates. A mixture of n-hexane and ethyl acetate is used as a mobile solvent; a mixture of dichloromethane and methanol is used as an eluant. 18 mg (26 μmol, 79%) of the title compound is isolated as a colorless oil.

EXAMPLE 81

[1R-[1α,2β(2R*,3S*),4α,4aβ,9β,10aβ]]-3-(Butoxycarbonyl)amino-2-hydroxy-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester 7 mg (9.7 μmol) of the compound that is presented according to Example 81a is reacted analogously to Example 1. After working-up and purification, 3.2 mg (5.7 μmol, 59%) of the title compound is isolated as a colorless oil.

$^1$H-NMR (CDCl$_3$): δ=0.66–1.02 (12H), 1.21–1.47 (5H), 1.48–1.88 (3H), 2.09 (1H), 2.20 (1H), 2.32 (1H), 2.67 (1H), 3.07 (1H), 3.20 (1H), 3.81 (1H), 4.03 (1H), 4.50 (1H), 4.93 (1H), 5.12 (1H), 5.18 (1H), 6.26 (1H), 6.71 (2H), 7.10–7.40 (5H, 7.48 (1H) ppm.

EXAMPLE 81a

[1R-[1α,2β(2R*,3S*),4α,4aβ,9β,10aβ]]-3-(Butoxycarbonyl)amino-2-triisopropylsilyloxy-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester 13 mg (16 μmol) of the compound that is presented according to Example 81b is hydrogenated analogously to Example 9a. After working-up and purification, 7 mg (9.7 μmol, 61%) of the title compound is isolated as a colorless oil.

EXAMPLE 81b

[1R-[1α,2β(2R*,3S*),4α,4aβ,9β,10aβ]]-3-(Butoxycarbonyl)amino-2-triisopropylsilyloxy-3-(4-benzyloxyphenyl)-propanoic acid-9-methyl-1,2,3,4,4a,9,10,10a-octahydro-1,12,12-trimethyl-4a,10a-epoxy-1,4-methanophenanthren-2-ylester By analogy with Example 1a, 10 mg (35 μmol) of compound A, presented according to Example 33b, is reacted using (3R,4S)-1-butoxycarbonyl-3-triisopropylsilyloxy-4-(4-pyridyl)-2-azetidinone, which has been produced analogously to the process that is described in Tetrahedron 1992 on page 6985 ff. After working-up and purification, 13 mg (16 μmol, 46%) of the title compound is isolated as a colorless oil.

EXAMPLE 82

[1R-[1α,2β(2R*,3S*),4α,4aβ,9β,10aβ]]-3-(Methoxycarbonyl)amino-2-hydroxy-3-cyclohexyl-propanoic acid-9-methyl-1,2,3,4,4a,9,10,10a-octahydro-1,12,12-trimethyl-4a,10a-epoxy-1,4-methanophenanthren-2-ylester 10 mg (15 μmol) of the compound that is presented according to Example 82a is reacted analogously to Example 1. After working-up and purification, 4.9 mg (9.6 μmol, 64%) of the title compound is isolated as a colorless oil.

$^1$H-NMR (CDCl$_3$): δ=0.78 (3H), 0.94 (3H), 1.02 (3H), 1.32 (3H), 0.85–1.38 (6H), 1.52–1.96 (6H), 2.04 (1H), 2.12 (1H), 2.37 (1H), 2.66 (1H), 3.05 (1H), 3.63 (4H), 3.90 (1H), 4.43 (1H), 4.93 (1H), 5.61 (1H), 7.12–7.33 (3H), 7.48 (1H) ppm.

EXAMPLE 82a

[1R-[1α,2β(2R*,3S*),4α,4aβ,9β,10aβ]]-3-(Methoxycarbonyl)amino-2-triisopropylsilyloxy-3-cyclohexyl-propanoic acid-9-methyl-1,2,3,4,4a,9,10,10a-octahydro-1,12,12-trimethyl-4a,10a-epoxy-1,4-methanophenanthren-2-ylester By analogy with Example 1a, 8.5 mg (30 μmol) of compound A, presented according to Example 33b, is reacted using the β-lactam that is presented according to Example 82b. After working-up and purification, 10 mg (15 μmol, 50%) of the title compound is isolated as a colorless oil

EXAMPLE 82b (3R,4S)-1-Methoxycarbonyl-3-triisopropylsilyloxy-4-cyclohexyl-2-azetidinone By analogy with Example 61e, 326 mg (1.0 mmol) of the compound that is presented according to Example 82c is reacted using methylchloroformate. After working-up and purification, 75 mg (204 μmol, 20%) of the title compound is isolated as a colorless oil.

EXAMPLE 82c (3R,4S)-3-Triisopropylsilyloxy-4-cyclohexyl-2-azetidinone

The solution of 1.0 g (3.13 mmol) of (3R,4S)-3-triisopropylsilyloxy-4-phenyl-2-azetidinone, which has been produced analogously to the process that is described in Tetrahedron 1992 on page 6985 ff, in 114 ml of ethyl acetate is mixed with 0.57 g of platinum on carbon (35) and hydrogenated at about 4 bar. After filtration, the residue that is obtained is purified chromatographically on about 70 ml of fine silica gel with a mobile solvent mixture of n-hexane and ethyl acetate. 735 mg (2.26 mmol, 72%) of the title compound is isolated as a colorless solid.

EXAMPLE 83

[1R-[1α,2β(2R*,3S*),4α,4aβ,9β,10aβ]]-3-(Methoxycarbonyl)amino-2-hydroxy-3-(4-hydroxyphenyl)-propanoic acid-9-methyl-1,2,3,4,4a,9,10,10a-octahydro-1,12,12-trimethyl-4a,10a-epoxy-1,4-methanophenanthren-2-ylester 11 mg (16 μmol) of the compound that is presented according to Example 83a is reacted analogously to Example 1. After working-up and purification, 6.2 mg (12 μmol, 75%) of the title compound is isolated as a colorless oil.

$^1$H-NMR (CDCl$_3$): δ=0.79 (3H), 0.89 (3H), 1.02 (3H), 1.40 (3H), 1.72 (1H), 2.09 (1H), 2.20 (1H), 2.29 (1H), 2.68 (1H), 3.07 (1H), 3.14 (1H), 3.60 (3H), 4.50 (1H), 4.91 (1H), 5.18 (1H), 5.21 (1H), 6.43 (1H), 6.69 (2H), 7.10–7.40 (5H), 7.49 (1H) ppm.

EXAMPLE 83a

[1R-[1α,2β(2R*,3S*),4α,4aβ,9β,10aβ]]-3-(Methoxycarbonyl)amino-2-triisopropylsilyloxy-3-(4-hydroxyphenyl)-propanoic acid-9-methyl-1,2,3,4,4a,9,10,10a-octahydro-1,12,12-trimethyl-4a,10a-etpoxy-1,4-methanophenanthren-2-ylester By analogy with Example 1a, 15 mg (53 μmol) of compound A, presented according to Example 33b, is reacted using (3R,4S)-1-methoxycarbonyl-3-triisopropylsilyloxy-4-(4-hydroxyphenyl)-2-azetidinone, which has been produced analogously to the process that is described in Tetrahedron 1992 on page 6985 ff. After working-up and purification, 20 mg (30 μmol, 56%) of the title compound is isolated as a colorless oil.

EXAMPLE 84

[1R-[1α,2β(2R*,3S*),4α,4aβ,9β,10aβ]]-3-(Methoxycarbonyl)amino-2-hydroxy-3-(4-hydroxyphenyl)-propanoic acid-9-methyl-1,2,3,4,4a,9,10,10a-octahydro-1,12,12-trimethyl-10a-hydroxy-1,4-methanophenanthren-2-ylester 25 mg (37 μmol) of the compound that is presented according to Example 84a is reacted analogously to Example 1. After working-up and purification, 8.5 mg (16.2 μmol, 44%) of the title compound is isolated as a colorless oil.

$^1$H-NMR (CDCl$_3$): δ=0.55 (3H), 0.94 (3H), 1.08 (3H), 1.42 (3H), 1.52 (1H), 1.90 (1H), 2.11 (1H), 2.51 (1H), 2.83 (1H), 3.10 (2H), 3.20 (1H), 3.67 (3H), 4.56 (1H), 4.81 (1H), 5.13 (1H), 5.17 (1H), 5.56 (1H), 6.56 (2H), 6.87 (2H), 7.08–7.32 (4H), 8.39 (1H) ppm.

EXAMPLE 84a

[1R-[1α,2β(2R*,3S*),4α,4aβ,9β,10aβ]]-3-(Methoxycarbonyl)amino-2-triisopropyloxy-3-(4-hydroxyphenyl)-propanoic acid-9-methyl-1,2,3,4,4a,9,10,10a-octahydro-1,12,12-trimethyl-10a-hydroxy-1,4-methanophenanthren-2-ylester 15 mg (53 μmol) of the compound that is presented according to Example 84b is reacted analogously to Example 83a. After working-up and purification, 25 mg (37 μmol, 69%) of the title compound is isolated as a colorless oil.

EXAMPLE 84b

[1R-(1α,2β,4α,4aβ,9β,10aβ)]-9-Methyl-1,2,3,4,4a,9,10,10a-octahydro-1,12,12-trimethyl-10a-hydroxy-1,4-methanophenanthren-2-ol (A) and [1R-(1α,2β,4α,9β)]-9-methyl-1,2,3,4,9,10-hexahydro-1,12,12-trimethyl-1,4-methanophenanthren-2-ol (B)

20 mg (70 μmol) of the compound that is presented according to Example 33b/A is reacted analogously to Example 9a. After working-up and purification, 5 mg (17 μmol, 25%) of title compound A as well as 7 mg (26 μmol, 37%) of title compound B are isolated, in each case as a colorless oil.

EXAMPLE 85

[1R-[1α,2β[2R*,3S*(2R*,3S*)],4α,4aβ,9β,10aβ]]-2-Hydroxy-3-amino-3-(4-pyridyl)-propanoic acid-9-methyl-1,2,3,4,4a,9,10,10a-octahydro-1,12,12-trimethyl-4a,10a-epoxy-1,4-methanophenanthren-2-ylester 11 mg (18 μmol) of the compound that is presented according to Example 42b is reacted analogously to Example 1. After working-up and purification, 6.3 mg (14 μmol, 78%) of the title compound is isolated as a colorless oil.

$^1$H-NMR (CDCl$_3$): δ=0.80 (3H), 0.92 (3H), 1.07 (3H), 1.33 (3H), 1.77 (1H), 1.89 (broad, 3H), 2.07 (1H), 2.16 (1H), 2.40 (1H), 2.69 (1H), 3.06 (1H), 4.45 (1H), 4.50 (1H), 4.85 (1H), 7.10–7.32 (3H), 7.41 (2H), 7.48 (1H), 8.54 (2H) ppm.

We claim:

1. A compound of formula I

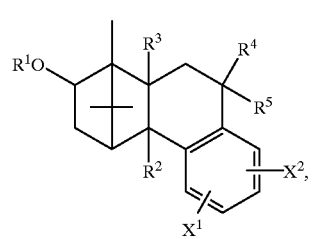

I wherein $R^1$ means T—C(O)—CH(OR$^6$)—CH(NHR$^{7a}$R$^{7b}$)—R$^8$, or C(O)—(OR$^{6a}$)—CH[NR$^7$(C(O)—CH(OR$^{6b}$)—CH(NR$^{7a}$R$^{7b}$)—R$^{8a}$)]—R$^{8b}$, $R^2$ means hydrogen, —OH, $C_1$–$C_{10}$ alkyl, $C_1$–$C_{10}$ alkoxy, —OC(O)R$^{9a}$, —OSO$_2$R$^{9a}$, NHR$^{9a}$, or NR$^{9a}$R$^{9b}$, $R^3$ means hydrogen, —OH, $C_1$–$C_{10}$ alkoxy, —OC(O)R$^{9b}$, or —OSO$_2$R$^{9b}$, or $R^2$, $R^3$ together mean an oxygen atom, $R^4$ means hydrogen, $C_1$–$C_{10}$ alkyl, or —(CH$_2$)$_n$—OR$^{11a}$, $R^5$ means hydrogen, $C_1$–$C_{10}$ alkyl, or —(CH$_2$)$_p$—OR$^{11b}$, or $R^4$, $R^5$ together mean an oxygen atom, a =CHR$^{10}$ group, a —CH$_2$—CH$_2$ group, or a CH$_2$—O group, $R^{6a}$, $R^{6b}$ are the same or different and each is an $R^6$ group, $R^6$ means hydrogen, $C_1$–$C_{10}$ alkyl, aryl, $C_1$–$C_{20}$ acyl, $C_7$–$C_{20}$ aralky, —SO$_2$R$^{9c}$, or R$^{15}$, $R^{7a}, R^{7b}$ are the same or different and each is an $R^7$ group,
$R^7$ means hydrogen, A, —C(O)R$^{12}$, —C(O)OR$^{12}$, —C(O)SR$^{12}$, —C(O)NHR$^{9d}$, —C(O)NR$^{9d}$R$^{9e}$, —SO$_2$R$^{12}$, or C$_1$–C$_{10}$ alkyl,
$R^{8a}, R^{8b}$ are the same or different and each is an $R^8$ group,
$R^8$ means

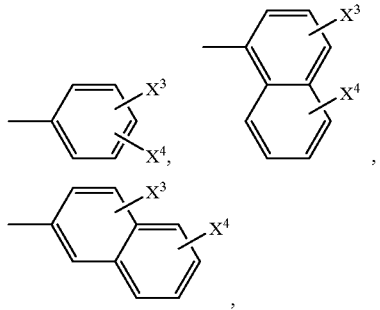

heteroaryl substituted by X$^3$, C$_7$–C$_{16}$ aralkyl, or C$_1$–C$_{10}$ alkyl,
$R^{9a-g}$, $R^{12}$ are the same or different and mean C$_1$–C$_{20}$ alkyl, C$_4$–C$_8$ cycloalkyl, aryl, or C$_7$–C$_{20}$ aralkyl,
$R^{10}$ means hydrogen, C$_1$–C$_{10}$ alkyl, or —(CH$_2$)$_s$—OR$^{13}$,
$R^{11a,b}$, $R^{13}$ are the same or different and mean hydrogen, C$_1$–C$_{10}$ alkyl, aryl, C$_1$–C$_{20}$ acyl, C$_7$–C$_{20}$ aralkyl, or —SO$_2$R$^{9c}$,
$R^{14a,b}$ are the same or different and mean hydrogen, A, C$_1$–C$_{10}$ alkyl, aryl, or C$_7$–C$_{16}$ aralkyl,
$R^{15}$ means (Y$^i_1$—Y$^i_2$—Y$^i_3$—. . .—Y$^i_r$)—H,
A means B—[O—(CH$_2$)$_t$—C(O)]$_{0-1}$, or farnesyl—P(O)(OR$^{9d}$)—O—(CH$_2$)$_t$—C(O)—,
B means an inhibitor of a protein kinase or an inhibitor of farnesyl protein transferase, linked to the molecule,
T means a bond, Z$^i$, or a group

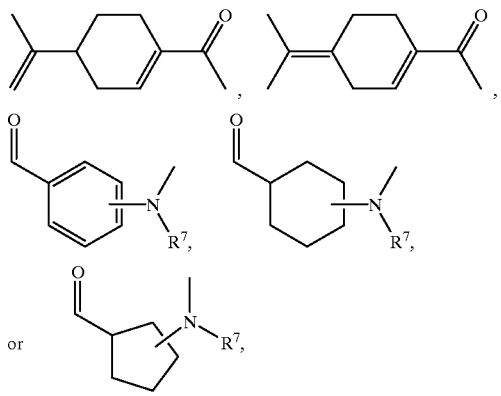

X$^1$ to X$^4$ are the same or different and mean X, provided that X$^3$ and X$^4$ in the case of R$^8$ and R$^{8b}$ are not present at the same time, in the meaning of hydrogen,
X can be hydrogen, halogen, —NO$_2$, —N$_3$, —CN, —NR$^{14a}$R$^{14b}$,
—NHSO$_2$R$^{9g}$, C$_1$–C$_{10}$ alkyl, C$_1$–C$_{20}$ acyl, C$_1$–C$_{20}$ acyloxy, OR$^6$,
—OP(O)R$^{9g}$(OR$^{12}$)—CO$_2$R$^{14}$, or —O—A,
Y$^i_{1-r}$ are the same or different and mean —[C(O)—W$^i$—NH]— =Z$^i$, wherein Z$^i$ as HO—Z$^i$—H represents an α-, β- or γ-amino acid "i" that is linked on its terminal end, n means 0 to 8
p means 1 to 8
r means 1 to 5
s means 1 to 8
t means 1 to 6,
and free hydroxyl groups in R$^1$, R$^2$, R$^3$, R$^4$, R$^5$, R$^{10}$, Z and X can be further modified functionally by etherification or esterification and free amino groups in R$^1$, R$^{15}$ or X or free acid groups in X are converted into their salts with physiologically compatible acids or bases, as well as their α-, β- or γ-cyclodextrin clathrates, as well as compounds of formula I that are encapsulated with liposomes.

2. A compound of formula I

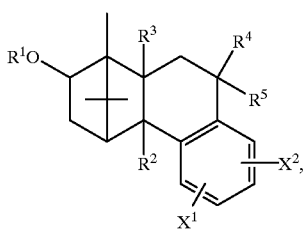

wherein
$R^1$ means T—C(O)—CH(OR$^6$)—CH(NHR$^{7a}$R$^{7b}$)—R$^8$, or C(O)—CH(OR$^{6a}$)—CH[NR$^7$(C(O)—CH(OR$^{6b}$)—CH(NR$^{7a}$R$^{7b}$)—R$^{8a}$)]—R$^{8b}$,
$R^2$ means hydrogen, —OH, C$_1$–C$_{10}$ alkyl, C$_1$–C$_{10}$ alkoxy, —OC(O)R$^{9a}$, —OSO$_2$R$^{9a}$, NHR$^{9a}$, or NR$^{9a}$R$^{9b}$,
$R^3$ means hydrogen, —OH, C$_1$–C$_{10}$ alkoxy, —OC(O)R$^{9b}$, or —OSO$_2$R$^{9b}$, or R$^2$, R$^3$ together mean an oxygen atom,
$R^4$ means hydrogen, C$_1$–C$_{10}$ alkyl, or —(CH$_2$)$_p$—OR$^{11a}$,
$R^5$ means hydrogen, C$_1$–C$_{10}$ alkyl, or —(CH$_2$)$_p$—OR$^{11b}$, or
$R^4$, $R^5$ together mean an oxygen atom, a =CHR$^{10}$ group, a —CH$_2$—CH$_2$ group, or a CH$_2$—O group,
$R^{6a}$, $R^{6b}$ are the same or different and each is an $R^6$ group,
$R^6$ means hydrogen, C$_{1-C10}$ alkyl, C$_6$–C$_{10}$ aryl, C$_1$–C$_{20}$ acyl, C$_7$–C$_{20}$ aralkyl, —SO$_2$R$^{9c}$, or R$^{15}$,
$R^{7a}$, $R^{7b}$ are the same or different and each is an $R^7$ group,
$R^7$ means hydrogen, A, —C(O)R$^{12}$, —C(O)OR$^{12}$, —C(O)SR$^{12}$, —C(O)NHR$^{9d}$, —C(O)NR$^{9d}$R$^{9e}$, —SO$_2$R$^{12}$, or C$_1$–C$_{10}$ alkyl,
$R^{8a}$, $R^{8b}$ are the same or different and each is an $R^8$ group,
$R^8$ means

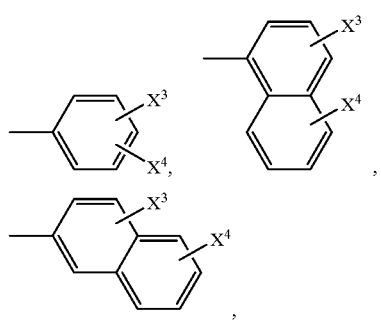

heteroaryl substituted by X$^3$, C$_7$–C$_{16}$ aralkyl, or C$_1$–C$_{10}$ alkyl, wherein heteroaryl is furyl, thienyl, pyridyl, pyrazolyl, pyrimidinyl, oxazolyl, pyridazinyl, pyrazinyl or quinolyl, $R^{9a-e,g}$, $R^{12}$ are the same or different and mean $C_1$–$C_{20}$ alkyl, $C_4$–$C_8$ cycloalkyl, $C_6$–$C_{10}$ aryl, or $C_7$–$C_{20}$ aralkyl, $R^{10}$ means hydrogen, $C_1$–$C_{10}$ alkyl, or —$(CH_2)_s$—$OR^{13}$, $R^{11a,b}$, $R^{13}$ are the same or different and mean hydrogen, $C_1$–$C_{10}$ alkyl, $C_6$–$C_{10}$ aryl, $C_1$–$C_{20}$ acyl, $C_7$–$C_{20}$ aralkyl, or —$SO_2R^{9c}$, $R^{14a,b}$ are the same or different and each is an $R^{14}$ group, wherein $R^{14}$ means hydrogen, A, $C_1$–$C_{10}$ alkyl, $C_6$–$C_{10}$ aryl, or $C_7$–$C_{16}$ aralkyl, $R^{15}$ means $(Y^i_1$—$Y^i_2$—$Y^i_3$— ... —$Y_{ir})$—H, A means B—[O—$(CH_2)_t$—C(O)]$_{0-1}$, or farnesyl—P(O)(OR$^{9d}$)0—O—$(CH_2)_t$—C(O)—, B means an inhibitor of a protein kinase or an inhibitor of farnesyl protein transferase, linked to the molecule, T means a bond, $Z^i$, or a group

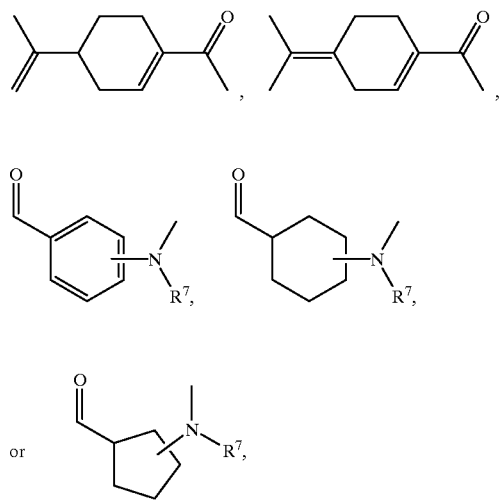

$X^1$–$X^4$ are the same or different and means X, provided that $X^3$ and $X^4$ in the case of $R^8$ and $R^{8b}$ are not present at the same time, in the meaning of hydrogen, X can be hydrogen, halogen, —$NO_2$, —$N_3$, —CN, —$NR^{14a}R^{14b}$, —$NHSO_2R^{9g}$, $C_1$–$C_{10}$ alkyl, $C_1$–$C_{20}$ acyl, $C_1$–$C_{20}$ acyloxy, $OR^6$, —OP(O)$R^{9g}(OR^{12})$—$CO_2R^{14}$, or —O—A, $Y^i_{1-r}$ are the same or different and mean —[C(O)—$W^i$—NH]—=$Z^i$, $Y^i_{1-r}$ are the same or different and mean —[C(O)—$W^i$—NH]—=$Z^i$, wherein $Z^i$ as HO—$Z^i$—H represents an α-, β- or γ-amino acid "i" that is linked to the molecule via the C(O)—OH end of the amino acid, n means 0 to 8 p means 1 to 8 r means 1 to 5 s means 1 to 8 t means 1 to 6, and/or free amino groups in $R^1$, $R^{15}$ or X, or free acid groups in X, are converted into their salts with physiologically compatible acids or bases.

3. A compound according to claim 2 wherein B is farnesyl.

4. A compound according to claim 2 wherein one or more free hydroxyl groups in $R^1$, $R^2$, $R^3$, $R^4$, $R^5$, $R^{10}$, Z or X are modified functionally by esterification with an amino acid, carboxylic acid, —O—P(O)(OH)$_2$, —O—P(O)(OR$^{9f}$)$_2$, —O—P(O)(OR$^{9f}$)(OH), —O—$SO_3H$, —O—$SO_3R^{9f}$, —O—C(O)—$CH_2$—O—PEG, —O—C(O)—$CH_2$—$CH_2$—C(O)—NH—PEG or —O—C(O)—$CH_2$—NH—C(O)—, or etherification with tetrahydropyranyl, tetrahydrofuranyl, tert-butyldimethylsilyl, tert-butyldiphenylsilyl or tribenzylsilyl.

5. An α-, β-, or γ- cyclodextrin clathrate of the compound according to claim 2.

6. A composition comprising a compound according to 2 which is encapsulated with a liposome.

7. A compound according to claim 2 wherein alkyl groups $R^2$, $R^4$, $R^5$, $R^6$, $R^7$, $R^8$, $R^9$, $R^{10}$, $R^{11}$, $R^{12}$, $R^{13}$, $R^{14}$ or X are substituted by 1–3 halogen atoms, $C_1$–$C_4$ alkoxy groups or $C_6$–$C_{12}$ aryl groups, which can in turn be substituted by 1–3 halogen atoms, di-($C_1$–$C_4$)-alkyamines or tri-($C_1$–$C_4$) alkylammonium.

8. A compound according to claim 2 wherein the alkoxy, acyl or acyloxy group contained in $R^2$, $R^3$, $R^6$, $R^{11}$, $R^{13}$, or X is methoxy, ethoxy, propoxy, isopropoxy, t-butyloxy, formyl, acetyl, proprionyl or isoproprionyl.

9. A compound according to claim 2 wherein the aralkyl group contained in $R^6$, $R^8$, $R^9$, $R^{10}$, $R^{11}$, $R^{12}$, $R^{13}$ or $R^{14}$ is benzyl, phenylethyl, naphthylmethyl, or naphthylethyl.

10. A compound according to claim 9 wherein said benzyl, phenylethyl, naphthylmethyl or naphthylethyl is substituted with a group as defined in X.

11. A compound according to claim 2 wherein said amino acid HO—Z—H is glycine, alanine, valine, leucine, isoleucine or proline.

12. A pharmaceutical composition comprising a compund according to claim 2 and a pharmaceutically acceptable carrier.

13. A process for the production of a compound of formula I according to claim 2, comprising reacting an alcohol of formula II

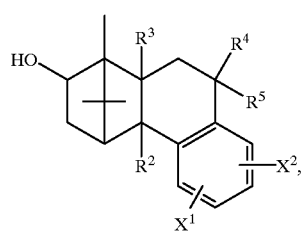

II in which $R^2$, $R^3$, $R^4$, $R^5$, $X^1$ and $X^2$ have the meanings as in claim 4 and are optionally protected in hydroxyl groups that are contained in $R^2$, $R^3$, $R^4$, $R^5$, $X^1$ or $X^2$, with a compound of formula IIIa, IIIb or IIIc,

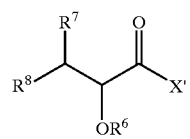

IIIa

-continued

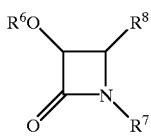
IIIb

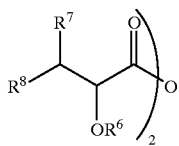
IIIc in which $R^6$, $R^7$ and $R^8$ in each case have the meanings as in claim 4 and X can be hydroxyl, $OR^9$, halogen and $NR^{14a}R^{14b}$, wherein free hydroxyl groups of said borneal derivative can be further modified functionally by etherification or esterification.

14. A method of treating a malignant tumor, comprising administering to a patient in need of treatment an effective amount of a compound according to claim 2.

15. A method of treating malaria, comprising administering to a patient in need of treatment an effective amount of a compound according to claim 2.

16. A method of treating a disease caused by gram-negative bacteria, comprising administering to a patient in need of treatment an effective amount of a compound according to claim 2.

17. A method of treating stroke, traumatic brain injury, chronic neurodegenerative disease, Alzheimer's disease or amyotropic lateral schlerosis, comprising administering to a patient in need of treatment an effective amount of a compound according to claim 2.

* * * * *